(12) United States Patent
Blaschuk et al.

(10) Patent No.: US 6,723,700 B1
(45) Date of Patent: Apr. 20, 2004

(54) COMPOUNDS AND METHODS FOR MODULATING CLAUDIN-MEDIATED FUNCTIONS

(75) Inventors: Orest W. Blaschuk, Westmount (CA); James Matthew Symonds, Ottawa (CA); Barbara J. Gour, Kemptville (CA)

(73) Assignee: Adherex Technologies, Inc., Ottawa (CA)

( * ) Notice: Subject to any disclaimer, the term of this patent is extended or adjusted under 35 U.S.C. 154(b) by 0 days.

(21) Appl. No.: 09/282,029

(22) Filed: Mar. 30, 1999

Related U.S. Application Data

(63) Continuation-in-part of application No. 09/185,908, filed on Nov. 3, 1998.

(51) Int. Cl.$^7$ .................. A61K 38/00; A61K 38/12; A61K 38/16
(52) U.S. Cl. ............... 514/12; 514/13; 514/14; 514/15; 530/324; 530/325; 530/326; 530/327; 530/328; 530/329; 530/330
(58) Field of Search ................. 530/300, 321, 530/324, 325, 326, 327, 328, 329, 330; 514/12, 13, 14, 15

(56) References Cited

FOREIGN PATENT DOCUMENTS

| WO | WO 95/06122 | 3/1995 |
|---|---|---|
| WO | WO 97/26001 | 7/1997 |

OTHER PUBLICATIONS

Chen et al. Lab. Invest. 78:353–363, Mar. 1998.*
USPTO Search—US–09–282–029–277. rag (pg 5) –US–09–282–029–rsp (pg 2) Compugen Sequence Search Nov. 3, 2000.*
Aberle et al., "β–catenin is a target for the ubiquitin–proteasome pathway," *The EMBO Journal* 16(13): 3797–3804, 1997.
Furuse et al., "A Single Gene Product, Claudin–1 or –2, Reconsitutes Tight Junction Strands and Recruits Occludin in Fibroblasts," *The Journal of Cell Biology* 143(2): 391–401, Oct. 19, 1998.
Hanna et al., "Localization of the Receptor–binding Region of *Clostridium perfringens* Enterotoxin Utilizing Cloned Toxin Fragments and Synthetic Peptides," *The Journal of Biological Chemistry* 266(17):11307–11043, Jun. 15, 1991.
Sonoda et al., "*Clostridium perfringens* Enterotoxin Fragment Removes Specific Claudins from Tight Junction Strands: Evidence for Direct Involvement of Claudins in Tight Junction Barrier," *The Journal of Cell Biology* 147(1): 195–204, Oct. 4, 1999.
Briehl and Miesfeld, "Isolation and Characterization of Transcripts Induced by Androgen Withdrawl and Apoptotic Cell Death in the Rat Ventral Prostate," *Molecular Endocrinology* 5: 1381–1388, 1991.
Furuse et al., "Claudin–1 and –2: Novel Integral Membrane Proteins Localizing at Tight Junctions with No Sequence Similarity to Occludin," *The Journal of Cell Biology* 141(7): 1539–1550, 1998.
Katahira et al., "Molecular Cloning and Functional Characterization of the Receptor for *Clostridium perfringens* Enterotoxin," *The Journal of Cell Biology* 136(6): 1239–1247, 1997.
Katahira et al., "*Clostridium perfringens* Enterotoxin Utilizes Two Structurally Related Membrane Proteins as Functional Receptors in Vivo," *The Journal of Biological Chemistry* 272(42): 26652–26658, 1997.

* cited by examiner

Primary Examiner—Christina Chan
Assistant Examiner—Maher Haddad
(74) Attorney, Agent, or Firm—Seed IP Law Group PLLC

(57) ABSTRACT

Method for using modulating agents to enhance or inhibit claudin-mediated cell adhesion in a variety of in vivo and in vitro contexts are provided. Within certain embodiments, the modulating agents may be used to increase blood/brain barrier permeability. The modulating agents comprise at least one claudin cell adhesion recognition sequence or an antibody or fragment thereof that specifically binds the claudin cell adhesion recognition sequence. Modulating agents may additionally comprise one or more cell adhesion recognition sequence recognized by other adhesion molecules. Such modulating agents may, but need not, be linked to a targeting agent, drug and/or support material.

5 Claims, 4 Drawing Sheets

| | |
|---|---|
| Mouse claudin-1 | PQWKIYSYAGDNIVTAQAIYEGLWMSCVSQ |
| Human claudin-1 | PQWRIYSYAGDNIVTAQAMYEGLWMSCVSQ |
| Mouse claudin-2 | PNWRTSSYVGASIVTAVGFSKGLWMECATH |
| Mouse claudin-3 | PMWRVSAFIGSSIITAQITWEGLWMNCVVQ |
| Human claudin-3 | PMWRVSAFIGSNIITSQNIWEGLWMNCVVQ |
| Rat claudin-3 | PMWRVSAFIGSSIITAQITWEGLWMNCVQS |
| Mouse claudin-4 | PMWRVTAFIGSNIVTAQTSWEGLWMNCVVQ |
| Human claudin-4 | PMWRVTAFIGSNIVTSQTIWEGLWMNCVVQ |
| Monkey claudin-4 | PMWRVTAFIGSNIVTSQTIWEGLWMNCVVQ |
| Mouse claudin-5 | PMWQVTAFLDHNIVTAQTTWKGLWMSCVVQ |
| Human claudin-5 | PMWQVTAFLDHNIVTAQTTWKGLWMSCVVQ |
| Mouse claudin-6 | PMWKVTAFIGNSIVVAQMVWEGLWMSCVVQ |
| Mouse claudin-7 | PQWQMSSYAGDNIITAQAMYKGLWMECVTQ |
| Mouse claudin-8 | PQWRVSAFIESNIVVFENRWEGLWMNCMRH |
| Mouse claudin-9 | PLWKVTAFIGNSIVVAQVVWEGLWMSCVVQ |
| Human claudin-9 | PLWKVTAFIGNSIVVAQVVWEGLWMSCVVQ |
| | : : :::: : |
| Consensus | PmWkxxafxgxnIitaqxxweGLWNxCvxq |
| | q q sy d s vvs yk |
| | r e |

*Fig. 1*

SEQUENCE LISTING

```
<160> NUMBER OF SEQ ID NOS: 480

<210> SEQ ID NO 1
<211> LENGTH: 8
<212> TYPE: PRT
<213> ORGANISM: Unknown
<220> FEATURE:
<221> NAME/KEY: MOD_RES
<222> LOCATION: (2)
<223> OTHER INFORMATION: Where Xaa is either Lysine or Arginine
<220> FEATURE:
<221> NAME/KEY: MOD_RES
<222> LOCATION: (3)
<223> OTHER INFORMATION: Where Xaa is an independently selected amino
      acid residue
<220> FEATURE:
<221> NAME/KEY: MOD_RES
<222> LOCATION: (4)
<223> OTHER INFORMATION: Where Xaa is an independently selected amino
      acid residue
<220> FEATURE:
<221> NAME/KEY: MOD_RES
<222> LOCATION: (5)
<223> OTHER INFORMATION: Where Xaa is either Serine or Alanine
<220> FEATURE:
```

```
<221> NAME/KEY: MOD_RES
<222> LOCATION: (6)
<223> OTHER INFORMATION: Where Xaa is either Tyrosine or Phenylalanine
<220> FEATURE:
<221> NAME/KEY: MOD_RES
<222> LOCATION: (7)
<223> OTHER INFORMATION: Where Xaa is an independently selected amino
      acid residue
<220> FEATURE:
<221> NAME/KEY: MOD_RES
<222> LOCATION: (8)
<223> OTHER INFORMATION: Where Xaa is either Glycine, Aspartic Acid or
      Glutamic Acid
<220> FEATURE:
<223> OTHER INFORMATION: Description of Unknown Organism:  Consensus
      Claudin Cell Adhesion Recognition Sequence

<400> SEQUENCE: 1

Trp Xaa Xaa Xaa Xaa Xaa Xaa Xaa
  1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Product of
      Synthesis based on Mouse Claudin-1 Cell Adhesion Recognition
      Sequence

<400> SEQUENCE: 2

Ile Tyr Ser Tyr
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:  Product of
      synthesis based on mouse claudin-2 cell adhesion
      recognition sequence

<400> SEQUENCE: 3

Thr Ser Ser Tyr
  1

<210> SEQ ID NO 4
<211> LENGTH: 4
<212> TYPE: PRT
<213> ORGANISM: Mus musculus
<220> FEATURE:
<223> OTHER INFORMATION: Description of Artificial Sequence:  Product of
      synthesis based on human,  mouse and Monkey CPE-R cell adhesion
      recognition sequence

<400> SEQUENCE: 4

Val Thr Ala Phe
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 cell adhesion recognition
      sequence

<400> SEQUENCE: 5
```

-continued

Val Ser Ala Phe
 1

<210> SEQ ID NO 6
<211> LENGTH: 42
<212> TYPE: PRT
<213> ORGANISM: Mus musculus

<400> SEQUENCE: 6

Pro Gln Trp Lys Ile Tyr Ser Tyr Ala Gly Asp Asn Ile Val Thr Ala
 1               5                  10                  15

Gln Ala Ile Tyr Glu Gly Leu Trp Met Ser Cys Val Ser Gln Ser Thr
            20                  25                  30

Gly Gln Ile Gln Cys Lys Val Phe Asp Ser
        35                  40

<210> SEQ ID NO 7
<211> LENGTH: 42
<212> TYPE: PRT
<213> ORGANISM: Mus musculus

<400> SEQUENCE: 7

Pro Asn Trp Arg Thr Ser Ser Tyr Val Gly Ala Ser Ile Val Thr Ala
 1               5                  10                  15

Val Gly Phe Ser Lys Gly Leu Trp Met Glu Cys Ala Thr His Ser Thr
            20                  25                  30

Gly Ile Thr Gln Cys Asp Ile Tyr Ser Thr
        35                  40

<210> SEQ ID NO 8
<211> LENGTH: 42
<212> TYPE: PRT
<213> ORGANISM: Homo sapiens

<400> SEQUENCE: 8

Pro Met Trp Arg Val Thr Ala Phe Ile Gly Ser Asn Ile Val Thr Ser
 1               5                  10                  15

Gln Thr Ile Trp Glu Gly Leu Trp Met Asn Cys Val Val Gln Ser Thr
            20                  25                  30

Gly Gln Met Gln Cys Lys Val Tyr Asp Ser
        35                  40

<210> SEQ ID NO 9
<211> LENGTH: 42
<212> TYPE: PRT
<213> ORGANISM: Mus musculus

<400> SEQUENCE: 9

Pro Met Trp Arg Val Thr Ala Phe Ile Gly Ser Asn Ile Val Thr Ala
 1               5                  10                  15

Gln Thr Ser Trp Glu Gly Leu Trp Met Asn Cys Val Val Gln Ser Thr
            20                  25                  30

Gly Gln Met Gln Cys Lys Met Tyr Asp Ser
        35                  40

<210> SEQ ID NO 10
<211> LENGTH: 42
<212> TYPE: PRT
<213> ORGANISM: Chlorocebus aethiops

<400> SEQUENCE: 10

Pro Met Trp Arg Val Thr Ala Phe Ile Gly Ser Asn Ile Val Thr Ser
1               5                   10                  15

Gln Thr Ile Trp Glu Gly Leu Trp Met Asn Cys Val Val Gln Ser Thr
            20                  25                  30

Gly Gln Met Gln Cys Lys Val Tyr Asp Ser
        35                  40

<210> SEQ ID NO 11
<211> LENGTH: 42
<212> TYPE: PRT
<213> ORGANISM: Homo sapiens

<400> SEQUENCE: 11

Pro Met Trp Arg Val Ser Ala Phe Ile Gly Ser Asn Ile Ile Thr Ser
1               5                   10                  15

Gln Asn Ile Trp Glu Gly Leu Trp Met Asn Cys Val Val Gln Ser Thr
            20                  25                  30

Gly Gln Met Gln Cys Lys Val Tyr Asp Ser
        35                  40

<210> SEQ ID NO 12
<211> LENGTH: 41
<212> TYPE: PRT
<213> ORGANISM: Rattus norvegicus

<400> SEQUENCE: 12

Pro Met Trp Arg Val Ser Ala Phe Ile Gly Ser Ser Ile Ile Thr Ala
1               5                   10                  15

Gln Ile Thr Trp Glu Gly Leu Trp Met Asn Cys Val Gln Ser Thr Gly
            20                  25                  30

Gln Met Gln Cys Lys Met Tyr Asp Ser
        35                  40

<210> SEQ ID NO 13
<211> LENGTH: 42
<212> TYPE: PRT
<213> ORGANISM: Unknown
<220> FEATURE:
<223> OTHER INFORMATION: Description of Unknown Organism: Consensus
      Claudin extracellular domain 1 sequence
<220> FEATURE:
<221> NAME/KEY: MOD_RES
<222> LOCATION: (2)
<223> OTHER INFORMATION: Where Xaa is an independently selected amino
      acid residue
<220> FEATURE:
<221> NAME/KEY: MOD_RES
<222> LOCATION: (4)
<223> OTHER INFORMATION: Where Xaa is either Arginine or Lysine
<220> FEATURE:
<221> NAME/KEY: MOD_RES
<222> LOCATION: (5)
<223> OTHER INFORMATION: Where Xaa is an independently selected amino
      acid
<220> FEATURE:
<221> NAME/KEY: MOD_RES
<222> LOCATION: (6)
<223> OTHER INFORMATION: Where Xaa is an independently selected amino
      acid residue
<220> FEATURE:
<221> NAME/KEY: MOD_RES
<222> LOCATION: (7)
<223> OTHER INFORMATION: Where Xaa is either Alanine or Serine
<220> FEATURE:
<221> NAME/KEY: MOD_RES
<222> LOCATION: (8)
<223> OTHER INFORMATION: Where Xaa is either Tyrosine or Phenylalanine
<220> FEATURE:

```
<221> NAME/KEY: MOD_RES
<222> LOCATION: (9)
<223> OTHER INFORMATION: Where Xaa is an independently selected amino
      acid residue
<220> FEATURE:
<221> NAME/KEY: MOD_RES
<222> LOCATION: (11)
<223> OTHER INFORMATION: Where Xaa is an independently selected amino
      acid residue
<220> FEATURE:
<221> NAME/KEY: MOD_RES
<222> LOCATION: (12)
<223> OTHER INFORMATION: Where Xaa is either Asparagine or Serine
<220> FEATURE:
<221> NAME/KEY: MOD_RES
<222> LOCATION: (14)
<223> OTHER INFORMATION: Where Xaa is either Valine or Isoleucine
<220> FEATURE:
<221> NAME/KEY: MOD_RES
<222> LOCATION: (16)
<223> OTHER INFORMATION: Where Xaa is either Alanine or Serine
<220> FEATURE:
<221> NAME/KEY: MOD_RES
<222> LOCATION: (17)
<223> OTHER INFORMATION: Where Xaa is either Glutamine or Valine
<220> FEATURE:
<221> NAME/KEY: MOD_RES
<222> LOCATION: (18)
<223> OTHER INFORMATION: Where Xaa is an independently selected amino
      acid residue
<220> FEATURE:
<221> NAME/KEY: MOD_RES
<222> LOCATION: (19)
<223> OTHER INFORMATION: Where Xaa is an independently selected amino
      acid residue
<220> FEATURE:
<221> NAME/KEY: MOD_RES
<222> LOCATION: (20)
<223> OTHER INFORMATION: Where Xaa is an independently selected amino
      acid residue
<220> FEATURE:
<221> NAME/KEY: MOD_RES
<222> LOCATION: (21)
<223> OTHER INFORMATION: Where Xaa is either Glutamic Acid or Lysine
<220> FEATURE:
<221> NAME/KEY: MOD_RES
<222> LOCATION: (26)
<223> OTHER INFORMATION: Where Xaa is an independently selected amino
      acid residue
<220> FEATURE:
<221> NAME/KEY: MOD_RES
<222> LOCATION: (28)
<223> OTHER INFORMATION: Where Xaa is either Valine or Alanine
<220> FEATURE:
<221> NAME/KEY: MOD_RES
<222> LOCATION: (29)
<223> OTHER INFORMATION: Where Xaa is an independently selected amino
      acid residue
<220> FEATURE:
<221> NAME/KEY: MOD_RES
<222> LOCATION: (30)
<223> OTHER INFORMATION: Where Xaa is an independently selected amino
      acid residue
<220> FEATURE:
<221> NAME/KEY: MOD_RES
<222> LOCATION: (31)
<223> OTHER INFORMATION: Where Xaa is either Serine or a gap
<220> FEATURE:
<221> NAME/KEY: MOD_RES
<222> LOCATION: (34)
<223> OTHER INFORMATION: Where Xaa is either Glutamine or Isoleucine
<220> FEATURE:
<221> NAME/KEY: MOD_RES
<222> LOCATION: (35)
<223> OTHER INFORMATION: Where Xaa is an independently selected amino
      acid residue
<220> FEATURE:
<221> NAME/KEY: MOD_RES
<222> LOCATION: (38)
```

```
<223> OTHER INFORMATION: Where Xaa is either Lysine or Aspartic Acid
<220> FEATURE:
<221> NAME/KEY: MOD_RES
<222> LOCATION: (39)
<223> OTHER INFORMATION: Where Xaa is Valine, Isoleucine or Methionine
<220> FEATURE:
<221> NAME/KEY: MOD_RES
<222> LOCATION: (40)
<223> OTHER INFORMATION: Where Xaa is either Phenylalanine or Tyrosine
<220> FEATURE:
<221> NAME/KEY: MOD_RES
<222> LOCATION: (41)
<223> OTHER INFORMATION: Where Xaa is either Aspartic Acid or Serine
<220> FEATURE:
<221> NAME/KEY: MOD_RES
<222> LOCATION: (42)
<223> OTHER INFORMATION: Where Xaa is either Serine or Threonine

<400> SEQUENCE: 13

Pro Xaa Trp Xaa Xaa Xaa Xaa Xaa Xaa Gly Xaa Xaa Ile Xaa Thr Xaa
 1               5                  10                  15

Xaa Xaa Xaa Xaa Xaa Gly Leu Trp Met Xaa Cys Xaa Xaa Xaa Xaa Thr
             20                  25                  30

Gly Xaa Xaa Gln Cys Xaa Xaa Xaa Xaa
         35                  40

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:  Product of
      Synthesis based on mousle claudin-1 sequence

<400> SEQUENCE: 14

Ile Tyr Ser Tyr Ile Tyr Ser Tyr
 1               5

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence

<400> SEQUENCE: 15

Gln Ile Tyr Ser Tyr Gln Ile Tyr Ser Tyr Gln Ile Tyr Ser Tyr
 1               5                  10                  15

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis.  N-CAM binding sequence

<400> SEQUENCE: 16

Lys Tyr Ser Phe Asn Tyr Asp Gly Ser Glu
 1               5                  10

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:  Product of
      Syntheis.  Occludin cell adhesion recognition sequence
```

```
<400> SEQUENCE: 17

Leu Tyr His Tyr
 1

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide
<220> FEATURE:
<221> NAME/KEY: MOD_RES
<222> LOCATION: ()
<223> OTHER INFORMATION: Where Xaa is dimethyl cysteine

<400> SEQUENCE: 18

Cys Ile Tyr Ser Tyr Xaa
 1               5

<210> SEQ ID NO 19
<211> LENGTH: 6
<212> TYPE: PRT
<213> ORGANISM: Artificial Sequence
<220> FEATURE:
<223> OTHER INFORMATION: Cyclic Peptide
<220> FEATURE:
<221> NAME/KEY: MOD_RES
<222> LOCATION: ()
<223> OTHER INFORMATION: Where Xaa is beta,beta-tetramethylene cysteine
<220> FEATURE:
<223> OTHER INFORMATION: Description of Artificial Sequence:  Product of
      synthesis based on mouse claudin-1 sequence

<400> SEQUENCE: 19

Xaa Ile Tyr Ser Tyr Cys
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis based on mouse claudin-1 sequence
<220> FEATURE:
<223> OTHER INFORMATION: Cyclic Peptide
<220> FEATURE:
<221> NAME/KEY: MOD_RES
<222> LOCATION: (1)
<223> OTHER INFORMATION: Where Xaa is beta,beta-pentamethylene cysteine

<400> SEQUENCE: 20

Xaa Ile Tyr Ser Tyr Cys
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide
<220> FEATURE:
<221> NAME/KEY: MOD_RES
<222> LOCATION: (1)
```

<223> OTHER INFORMATION: Where Xaa is beta-mercaptopropionic acid

<400> SEQUENCE: 21

Xaa Ile Tyr Ser Tyr Cys
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:  Product of
      Synthesis based on mouse claudin-1 sequence
<220> FEATURE:
<223> OTHER INFORMATION: Cyclic Peptide
<220> FEATURE:
<221> NAME/KEY: MOD_RES
<222> LOCATION: (1)
<223> OTHER INFORMATION: Where Xaa is
      beta,beta-pentamethylene-beta-mercaptopropionic
      acid

<400> SEQUENCE: 22

Xaa Ile Tyr Ser Tyr Cys
 1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide
<220> FEATURE:
<221> NAME/KEY: MOD_RES
<222> LOCATION: (1)
<223> OTHER INFORMATION: Where Xaa is  D-Tyrosine

<400> SEQUENCE: 23

Xaa Ile Tyr Ser Tyr
 1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:  Product of
      Synthesis
<220> FEATURE:
<223> OTHER INFORMATION: Cyclic Peptide

<400> SEQUENCE: 24

Trp Gly Gly Trp
 1

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:  Product of
      Synthesis based on N-cadherin cell adhesion recognition sequence

<400> SEQUENCE: 25

Phe His Leu Arg Ala His Ala Val Asp Ile Asn Gly Asn Gln Val
 1               5                  10                  15

```
<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on E-cadherin cell adhesion recognition sequence

<400> SEQUENCE: 26

Leu Phe Ser His Ala Val Ser Ser Asn Gly
 1               5                  10

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence

<400> SEQUENCE: 27

Ile Tyr Ser Tyr Ala
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence

<400> SEQUENCE: 28

Ile Tyr Ser Tyr Ala Gly
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence

<400> SEQUENCE: 29

Lys Ile Tyr Ser Tyr
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence

<400> SEQUENCE: 30

Lys Ile Tyr Ser Tyr Ala
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence
```

```
<400> SEQUENCE: 31

Lys Ile Tyr Ser Tyr Ala Gly
  1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence

<400> SEQUENCE: 32

Trp Lys Ile Tyr Ser Tyr
  1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence

<400> SEQUENCE: 33

Trp Lys Ile Tyr Ser Tyr Ala
  1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Product of
      Synthesis based on mouse claudin-1 sequence

<400> SEQUENCE: 34

Trp Lys Ile Tyr Ser Tyr Ala Gly
  1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence

<400> SEQUENCE: 35

Thr Ser Ser Tyr Val
  1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence

<400> SEQUENCE: 36

Thr Ser Ser Tyr Val Gly
  1               5

<210> SEQ ID NO 37
<211> LENGTH: 5
<212> TYPE: PRT
```

```
<213> ORGANISM: Artificial Sequence
<220> FEATURE:
<223> OTHER INFORMATION: Description of Artificial Sequence:  Product of
      synthesis based on mouse claudin-2 sequence

<400> SEQUENCE: 37

Arg Thr Ser Ser Tyr
  1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence

<400> SEQUENCE: 38

Arg Thr Ser Ser Tyr Val
  1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence

<400> SEQUENCE: 39

Arg Thr Ser Ser Tyr Val Gly
  1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence

<400> SEQUENCE: 40

Trp Arg Thr Ser Ser Tyr
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence

<400> SEQUENCE: 41

Trp Arg Thr Ser Ser Tyr Val
  1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence

<400> SEQUENCE: 42

Trp Arg Thr Ser Ser Tyr Val Gly
  1               5
```

```
<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences

<400> SEQUENCE: 43

Val Thr Ala Phe Ile
  1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences

<400> SEQUENCE: 44

Val Thr Ala Phe Ile Gly
  1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences

<400> SEQUENCE: 45

Arg Val Thr Ala Phe
  1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences

<400> SEQUENCE: 46

Arg Val Thr Ala Phe Ile
  1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences

<400> SEQUENCE: 47

Arg Val Thr Ala Phe Ile Gly
  1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences
```

```
<400> SEQUENCE: 48

Trp Arg Val Thr Ala Phe
 1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences

<400> SEQUENCE: 49

Trp Arg Val Thr Ala Phe Ile
 1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R sequences

<400> SEQUENCE: 50

Trp Arg Val Thr Ala Phe Ile Gly
 1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences

<400> SEQUENCE: 51

Val Ser Ala Phe Ile
 1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences

<400> SEQUENCE: 52

Val Ser Ala Phe Ile Gly
 1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences

<400> SEQUENCE: 53

Arg Val Ser Ala Phe
 1               5

<210> SEQ ID NO 54
<211> LENGTH: 6
```

```
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences

<400> SEQUENCE: 54

Arg Val Ser Ala Phe Ile
 1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences

<400> SEQUENCE: 55

Arg Val Ser Ala Phe Ile Gly
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences

<400> SEQUENCE: 56

Trp Arg Val Ser Ala Phe
 1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences

<400> SEQUENCE: 57

Trp Arg Val Ser Ala Phe Ile
 1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences

<400> SEQUENCE: 58

Trp Arg Val Ser Ala Phe Ile Gly
 1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 59
```

```
Cys Ile Tyr Ser Tyr Cys
 1               5
```

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 60

```
Cys Ile Tyr Ser Tyr Ala Cys
 1               5
```

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 61

```
Cys Ile Tyr Ser Tyr Ala Gly Cys
 1               5
```

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 62

```
Cys Lys Ile Tyr Ser Tyr Cys
 1               5
```

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 63

```
Cys Lys Ile Tyr Ser Tyr Ala Cys
 1               5
```

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

```
<400> SEQUENCE: 64

Cys Lys Ile Tyr Ser Tyr Ala Gly Cys
  1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 65

Cys Trp Lys Ile Tyr Ser Tyr Cys
  1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 66

Cys Trp Lys Ile Tyr Ser Tyr Ala Cys
  1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 67

Cys Trp Lys Ile Tyr Ser Tyr Ala Gly Cys
  1               5                  10

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 68

Lys Ile Tyr Ser Tyr Asp
  1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide
```

<400> SEQUENCE: 69

Lys Ile Tyr Ser Tyr Ala Asp
 1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 70

Lys Ile Tyr Ser Tyr Ala Gly Asp
 1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 71

Lys Lys Ile Tyr Ser Tyr Asp
 1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 72

Lys Lys Ile Tyr Ser Tyr Ala Asp
 1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 73

Lys Lys Ile Tyr Ser Tyr Ala Gly Asp
 1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:

<223> OTHER INFORMATION: Cyclic Peptide

<400> SEQUENCE: 74

Lys Trp Lys Ile Tyr Ser Tyr Asp
 1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 75

Lys Trp Lys Ile Tyr Ser Tyr Ala Asp
 1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 76

Lys Trp Lys Ile Tyr Ser Tyr Ala Gly Asp
 1               5                  10

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 77

Lys Ile Tyr Ser Tyr Glu
 1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 78

Lys Ile Tyr Ser Tyr Ala Glu
 1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence

```
<220> FEATURE:
<223> OTHER INFORMATION: Cyclic Peptide

<400> SEQUENCE: 79

Lys Ile Tyr Ser Tyr Ala Gly Glu
  1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 80

Lys Lys Ile Tyr Ser Tyr Glu
  1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 81

Lys Lys Ile Tyr Ser Tyr Ala Glu
  1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 82

Lys Lys Ile Tyr Ser Tyr Ala Gly Glu
  1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 83

Lys Trp Lys Ile Tyr Ser Tyr Glu
  1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence:  Product of
```

```
      synthesis based on mouse claudin-1 sequence
<220> FEATURE:
<223> OTHER INFORMATION: Cyclic Peptide

<400> SEQUENCE: 84

Lys Trp Lys Ile Tyr Ser Tyr Ala Glu
  1               5

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 85

Lys Trp Lys Ile Tyr Ser Tyr Ala Gly Glu
  1               5                  10

<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 86

Asp Ile Tyr Ser Tyr Lys
  1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 87

Asp Ile Tyr Ser Tyr Ala Lys
  1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 88

Asp Ile Tyr Ser Tyr Ala Gly Lys
  1               5

<210> SEQ ID NO 89
<211> LENGTH: 7
<212> TYPE: PRT
<213> ORGANISM: Artificial Sequence
<220> FEATURE:
```

```
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 89

Asp Lys Ile Tyr Ser Tyr Lys
  1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 90

Asp Lys Ile Tyr Ser Tyr Ala Lys
  1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 91

Asp Lys Ile Tyr Ser Tyr Ala Gly Lys
  1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 92

Asp Trp Lys Ile Tyr Ser Tyr Lys
  1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on mouse claudin-1 sequence
<220> FEATURE:
<223> OTHER INFORMATION: Cyclic Peptide

<400> SEQUENCE: 93

Asp Trp Lys Ile Tyr Ser Tyr Ala Lys
  1               5

<210> SEQ ID NO 94
<211> LENGTH: 10
<212> TYPE: PRT
<213> ORGANISM: Artificial Sequence
```

```
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 94

Asp Trp Lys Ile Tyr Ser Tyr Ala Gly Lys
 1               5                  10

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 95

Glu Ile Tyr Ser Tyr Lys
 1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 96

Glu Ile Tyr Ser Tyr Ala Lys
 1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 97

Glu Ile Tyr Ser Tyr Ala Gly Lys
 1               5

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 98

Glu Lys Ile Tyr Ser Tyr Lys
 1               5

<210> SEQ ID NO 99
<211> LENGTH: 8
<212> TYPE: PRT
```

```
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 99

Glu Lys Ile Tyr Ser Tyr Ala Lys
 1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 100

Glu Lys Ile Tyr Ser Tyr Ala Gly Lys
 1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 101

Glu Trp Lys Ile Tyr Ser Tyr Lys
 1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 102

Glu Trp Lys Ile Tyr Ser Tyr Ala Lys
 1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 103

Glu Trp Lys Ile Tyr Ser Tyr Ala Gly Lys
 1               5                  10

<210> SEQ ID NO 104
<211> LENGTH: 5
```

```
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 104

Ile Tyr Ser Tyr Ala
 1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 105

Ile Tyr Ser Tyr Ala Gly
 1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 106

Lys Ile Tyr Ser Tyr
 1               5

<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 107

Lys Ile Tyr Ser Tyr Ala Gly
 1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-1 sequence
<220> FEATURE:
<223> OTHER INFORMATION: Cyclic Peptide

<400> SEQUENCE: 108

Trp Lys Ile Tyr Ser Tyr
 1               5

<210> SEQ ID NO 109
```

```
<211> LENGTH: 7
<212> TYPE: PRT
<213> ORGANISM: Artificial Sequence
<220> FEATURE:
<223> OTHER INFORMATION: Description of Artificial Sequence:   Product of
      synthesis based on mouse claudin-1 sequence
<220> FEATURE:
<223> OTHER INFORMATION: Cyclic Peptide

<400> SEQUENCE: 109

Trp Lys Ile Tyr Ser Tyr Ala
 1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence:   Product of
      synthesis based on mouse claudin-1 sequence
<220> FEATURE:
<223> OTHER INFORMATION: Cyclic Peptide

<400> SEQUENCE: 110

Trp Lys Ile Tyr Ser Tyr Ala Gly
 1               5

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence:   Product of
      synthesis based on mouse claudin-2 sequence
<220> FEATURE:
<223> OTHER INFORMATION: Cyclic Peptide

<400> SEQUENCE: 111

Cys Thr Ser Ser Tyr Cys
 1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence:   Product of
      synthesis based on mouse claudin-2 sequence
<220> FEATURE:
<223> OTHER INFORMATION: Cyclic Peptide

<400> SEQUENCE: 112

Cys Thr Ser Ser Tyr Val Cys
 1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence:   Product of
      synthesis based on mouse claudin-2 sequence
<220> FEATURE:
<223> OTHER INFORMATION: Cyclic Peptide

<400> SEQUENCE: 113

Cys Thr Ser Ser Tyr Val Gly Cys
 1               5
```

```
<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 114

Cys Arg Thr Ser Ser Tyr Cys
 1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 115

Cys Arg Thr Ser Ser Tyr Val Cys
 1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 116

Cys Arg Thr Ser Ser Tyr Val Gly Cys
 1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 117

Cys Trp Arg Thr Ser Ser Tyr Cys
 1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 118

Cys Trp Arg Thr Ser Ser Tyr Val Cys
 1               5
```

```
<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 119

Cys Trp Arg Thr Ser Ser Tyr Val Gly Cys
 1               5                  10

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 120

Lys Thr Ser Ser Tyr Asp
 1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 121

Lys Thr Thr Ser Tyr Val Asp
 1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 122

Lys Thr Thr Ser Tyr Val Gly Asp
 1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 123

Lys Arg Thr Ser Ser Tyr Asp
 1               5
```

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 124

Lys Arg Thr Ser Ser Tyr Val Asp
 1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 125

Lys Arg Thr Ser Ser Tyr Val Gly Asp
 1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 126

Lys Trp Arg Thr Ser Ser Tyr Asp
 1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 127

Lys Trp Arg Thr Ser Ser Tyr Val Asp
 1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 128

Lys Trp Arg Thr Ser Ser Tyr Val Gly Asp

```
                1               5              10
```

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 129

```
Lys Thr Ser Ser Tyr Glu
 1               5
```

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 130

```
Lys Thr Ser Ser Tyr Val Glu
 1               5
```

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 131

```
Lys Thr Ser Ser Tyr Val Gly Glu
 1               5
```

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 132

```
Lys Arg Thr Ser Ser Tyr Glu
 1               5
```

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 133

```
Lys Arg Thr Ser Ser Tyr Val Glu
  1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 134

Lys Arg Thr Ser Ser Tyr Val Gly Glu
  1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 135

Lys Trp Arg Thr Ser Ser Tyr Glu
  1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 136

Lys Trp Arg Thr Ser Ser Tyr Val Glu
  1               5

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 137

Lys Trp Arg Thr Ser Ser Tyr Val Gly Glu
  1               5                  10

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 138
```

Asp Thr Ser Ser Tyr Lys
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 139

Asp Thr Ser Ser Tyr Val Lys
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 140

Asp Thr Ser Ser Tyr Val Gly Lys
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 141

Asp Arg Thr Ser Ser Tyr Lys
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 142

Asp Arg Thr Ser Ser Tyr Val Lys
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

```
<400> SEQUENCE: 143

Asp Arg Thr Ser Ser Tyr Val Gly Lys
 1               5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 144

Asp Trp Arg Thr Ser Ser Tyr Lys
 1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 145

Asp Trp Arg Thr Ser Ser Tyr Val Lys
 1               5

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 146

Asp Trp Arg Thr Ser Ser Tyr Val Gly Lys
 1               5                  10

<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 147

Glu Thr Ser Ser Tyr Lys
 1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide
```

```
<400> SEQUENCE: 148

Glu Thr Ser Ser Tyr Val Lys
 1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 149

Glu Thr Thr Ser Tyr Val Gly Lys
 1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 150

Glu Arg Thr Ser Ser Tyr Lys
 1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 151

Glu Arg Thr Ser Ser Tyr Val Lys
 1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 152

Glu Arg Thr Ser Ser Tyr Val Gly Lys
 1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
```

```
<223> OTHER INFORMATION: Cyclic Peptide

<400> SEQUENCE: 153

Glu Trp Arg Thr Ser Ser Tyr Lys
  1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 154

Glu Trp Arg Thr Ser Ser Tyr Val Lys
  1               5

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 155

Glu Trp Arg Thr Ser Ser Tyr Val Gly Lys
  1               5                  10

<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 156

Thr Ser Ser Tyr Val
  1               5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
<220> FEATURE:
<223> OTHER INFORMATION: Cyclic Peptide

<400> SEQUENCE: 157

Thr Ser Ser Tyr Val Gly
  1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Product of
      synthesis based on mouse claudin-2 sequence
```

```
<220> FEATURE:
<223> OTHER INFORMATION: Cyclic Peptide

<400> SEQUENCE: 158

Arg Thr Ser Ser Tyr
 1               5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 159

Arg Thr Ser Ser Tyr Val
 1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 160

Arg Thr Ser Ser Tyr Val Gly
 1               5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 161

Trp Arg Thr Ser Ser Tyr
 1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on mouse claudin-2 sequence
<220> FEATURE:
<223> OTHER INFORMATION: Cyclic Peptide

<400> SEQUENCE: 162

Trp Arg Thr Ser Ser Tyr Val
 1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence:  Product of
```

```
            synthesis based on mouse claudin-2 sequence
<220> FEATURE:
<223> OTHER INFORMATION: Cyclic Peptide

<400> SEQUENCE: 163 g Thr Ser Ser Tyr Val Gly
            5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 164

Cys Val Thr Ala Phe Cys
 1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 165

Cys Val Thr Ala Phe Ile Cys
 1               5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 166

Cys Val Thr Ala Phe Ile Gly Cys
 1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 167

Cys Arg Val Thr Ala Phe Cys
 1               5

<210> SEQ ID NO 168
```

-continued

```
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 168

Cys Arg Val Thr Ala Phe Ile Cys
  1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 169

Cys Arg Val Thr Ala Phe Ile Gly Cys
  1               5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 170

Cys Trp Arg Val Thr Ala Phe Cys
  1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 171

Cys Trp Arg Val Thr Ala Phe Ile Cys
  1               5

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 172
```

Cys Trp Arg Val Thr Ala Phe Ile Gly Cys
1               5                   10

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 173

Lys Val Thr Ala Phe Asp
1               5

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 174

Lys Val Thr Ala Phe Ile Asp
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 175

Lys Val Thr Ala Phe Ile Gly Asp
1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 176

Lys Arg Val Thr Ala Phe Asp
1               5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence:  Product of -continued

```
      synthesis based on human, mouse and monkey CPE-R
      sequences
<220> FEATURE:
<223> OTHER INFORMATION: Cyclic Peptide

<400> SEQUENCE: 177

Lys Arg Val Thr Ala Phe Ile Asp
  1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 178

Lys Arg Val Thr Ala Phe Ile Gly Asp
  1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 179

Lys Trp Arg Val Thr Ala Phe Asp
  1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 180

Lys Trp Arg Val Thr Ala Phe Ile Asp
  1               5

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 181

Lys Trp Arg Val Thr Ala Phe Ile Gly Asp
  1               5                  10
```

```
<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 182

Lys Val Thr Ala Phe Glu
 1               5

<210> SEQ ID NO 183
<211> LENGTH: 7
<212> TYPE: PRT
<213> ORGANISM: Artificial Sequence
<220> FEATURE:
OTHER INFORMATION: Description of Artificial Sequence: Product of
synthesis based on human, mouse and monkey CPE-R
      sequences
<220> FEATURE:
<223> OTHER INFORMATION: Cyclic Peptide

<400> SEQUENCE: 183

Lys Val Thr Ala Phe Ile Glu
 1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 184

Lys Val Thr Ala Phe Ile Gly Glu
 1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 185

Lys Arg Val Thr Ala Phe Glu
 1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide
```

```
<400> SEQUENCE: 186

Lys Arg Val Thr Ala Phe Ile Glu
  1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 187

Lys Arg Val Thr Ala Phe Ile Gly Glu
  1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 188

Lys Trp Arg Val Thr Ala Phe Glu
  1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 189

Lys Trp Arg Val Thr Ala Phe Ile Glu
  1               5

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 190

Lys Trp Arg Val Thr Ala Phe Ile Gly Glu
  1               5                  10

<210> SEQ ID NO 191
<211> LENGTH: 6
<212> TYPE: PRT
<213> ORGANISM: Artificial Sequence
<220> FEATURE:
```

-continued

```
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 191

Asp Val Ala Thr Phe Lys
  1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 192

Asp Val Thr Ala Phe Ile Lys
  1               5

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 193

Asp Val Thr Ala Phe Ile Gly Lys
  1               5

<210> SEQ ID NO 194
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 194

Asp Arg Val Thr Ala Phe Lys
  1               5

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 195

Asp Arg Val Thr Ala Phe Ile Lys
  1               5
```

```
<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 196

Asp Arg Val Thr Ala Phe Ile Gly Lys
 1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 197

Asp Trp Arg Val Thr Ala Phe Lys
 1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 198

Asp Trp Arg Val Thr Ala Phe Ile Lys
 1               5

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 199

Asp Trp Arg Val Thr Ala Phe Ile Gly Lys
 1               5                  10

<210> SEQ ID NO 200
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide
```

```
<400> SEQUENCE: 200

Glu Val Thr Ala Phe Lys
 1               5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 201

Glu Val Thr Ala Phe Ile Lys
 1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 202

Glu Val Thr Ala Phe Ile Gly Lys
 1               5

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 203

Glu Arg Val Thr Ala Phe Lys
 1               5

<210> SEQ ID NO 204
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 204

Glu Arg Val Thr Ala Phe Ile Lys
 1               5

<210> SEQ ID NO 205
<211> LENGTH: 9
<212> TYPE: PRT
<213> ORGANISM: Artificial Sequence
```

```
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 205

Glu Arg Val Thr Ala Phe Ile Gly Lys
 1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 206

Glu Trp Arg Val Thr Ala Phe Lys
 1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 207

Glu Trp Arg Val Thr Ala Phe Ile Lys
 1               5

<210> SEQ ID NO 208
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 208

Glu Trp Arg Val Thr Ala Phe Ile Gly Lys
 1               5                  10

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 209

Val Thr Ala Phe Ile
 1               5
```

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 210

Val Thr Ala Phe Ile Gly
 1               5

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 211

Arg Val Thr Ala Phe
 1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 212

Arg Val Thr Ala Phe Ile
 1               5

<210> SEQ ID NO 213
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:
<223> OTHER INFORMATION: Cyclic Peptide

<400> SEQUENCE: 213

Arg Val Thr Ala Phe Ile Gly
 1               5

<210> SEQ ID NO 214
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human, mouse and monkey CPE-R
      sequences
<220> FEATURE:

```
<223> OTHER INFORMATION: Cyclic Peptide

<400> SEQUENCE: 214

Trp Arg Val Thr Ala Phe
 1               5

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 215

Trp Arg Val Thr Ala Phe Ile
 1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human, mouse and monkey CPE-R
      sequences
<220> FEATURE:
<223> OTHER INFORMATION: Cyclic Peptide

<400> SEQUENCE: 216

Trp Arg Val Thr Ala Phe Ile Gly
 1               5

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 217

Cys Val Ser Ala Phe Cys
 1               5

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 218

Cys Val Ser Ala Phe Ile Cys
 1               5

<210> SEQ ID NO 219
<211> LENGTH: 8
<212> TYPE: PRT
<213> ORGANISM: Artificial Sequence
<220> FEATURE:
```

```
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 219

Cys Val Ser Ala Phe Ile Gly Cys
  1               5

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 220

Cys Arg Val Ser Ala Phe Cys
  1               5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 221

Cys Arg Val Ser Ala Phe Ile Cys
  1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 222

Cys Arg Val Ser Ala Phe Ile Gly Cys
  1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 223

Cys Trp Arg Val Ser Ala Phe Cys
  1               5

<210> SEQ ID NO 224
<211> LENGTH: 9
<212> TYPE: PRT
<213> ORGANISM: Artificial Sequence
```

<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 224

Cys Trp Arg Val Ser Ala Phe Ile Cys
 1               5

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 225

Cys Trp Arg Val Ser Ala Phe Ile Gly Cys
 1               5                   10

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 226

Lys Val Ser Ala Phe Asp
 1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 227

Lys Val Ser Ala Phe Ile Asp
 1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 228

Lys Val Ser Ala Phe Ile Gly Asp
 1               5

<210> SEQ ID NO 229
<211> LENGTH: 7
<212> TYPE: PRT

```
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 229

Lys Arg Val Ser Ala Phe Asp
  1               5

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 230

Lys Arg Val Ser Ala Phe Ile Asp
  1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 231

Lys Arg Val Ser Ala Phe Ile Gly Asp
  1               5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 232

Lys Trp Arg Val Ser Ala Phe Asp
  1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 233

Lys Trp Arg Val Ser Ala Phe Ile Asp
  1               5

<210> SEQ ID NO 234
<211> LENGTH: 10
```

```
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 234

Lys Trp Arg Val Ser Ala Phe Ile Gly Asp
 1               5                  10

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 235

Lys Val Ser Ala Phe Glu
 1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 236

Lys Val Ser Ala Phe Ile Glu
 1               5

<210> SEQ ID NO 237
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 237

Lys Val Ser Ala Phe Ile Gly Glu
 1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 238

Lys Arg Val Ser Ala Phe Glu
 1               5

<210> SEQ ID NO 239
```

```
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 239

Lys Arg Val Ser Ala Phe Ile Glu
  1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 240

Lys Arg Val Ser Ala Phe Ile Gly Glu
  1               5

<210> SEQ ID NO 241
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 241

Lys Trp Arg Val Ser Ala Phe Glu
  1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 242

Lys Trp Arg Val Ser Ala Phe Ile Glu
  1               5

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 243

Lys Trp Arg Val Ser Ala Phe Ile Gly Glu
  1               5                  10
```

-continued

```
<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 244

Asp Val Ser Ala Phe Lys
 1               5

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 245

Asp Val Ser Ala Phe Ile Lys
 1               5

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 246

Asp Val Ser Ala Phe Ile Gly Lys
 1               5

<210> SEQ ID NO 247
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 247

Asp Arg Val Ser Ala Phe Lys
 1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 248

Asp Arg Val Ser Ala Phe Ile Lys
 1               5
```

```
<210> SEQ ID NO 249
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 249

Asp Arg Val Ser Ala Phe Ile Gly Lys
  1               5

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 250

Asp Trp Arg Val Ser Ala Phe Lys
  1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 251

Asp Trp Arg Val Ser Ala Phe Ile Lys
  1               5

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 252

Asp Trp Arg Val Ser Ala Phe Ile Gly Lys
  1               5                  10

<210> SEQ ID NO 253
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 253

Glu Val Ser Ala Phe Lys
  1               5
```

```
<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 254

Glu Val Ser Ala Phe Ile Lys
 1               5

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 255

Glu Val Ser Ala Phe Ile Gly Lys
 1               5

<210> SEQ ID NO 256
<211> LENGTH: 7
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 256

Glu Arg Val Ser Ala Phe Lys
 1               5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 257

Glu Arg Val Ser Ala Phe Ile Lys
 1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 258

Glu Arg Val Ser Ala Phe Ile Gly Lys
```

```
        1               5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 259

Glu Trp Arg Val Ser Ala Phe Lys
  1               5

<210> SEQ ID NO 260
<211> LENGTH: 9
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 260

Glu Trp Arg Val Ser Ala Phe Ile Lys
  1               5

<210> SEQ ID NO 261
<211> LENGTH: 10
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 261

Glu Trp Arg Val Ser Ala Phe Ile Gly Lys
  1               5                  10

<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 262

Val Ser Ala Phe Ile
  1               5

<210> SEQ ID NO 263
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 263
```

```
Val Ser Ala Phe Ile Gly
 1               5

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 264

Arg Val Ser Ala Phe
 1               5

<210> SEQ ID NO 265
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 265

Arg Val Ser Ala Phe Ile
 1               5

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 266

Arg Val Ser Ala Phe Ile Gly
 1               5

<210> SEQ ID NO 267
<211> LENGTH: 6
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 267

Trp Arg Val Ser Ala Phe
 1               5

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence:  Product of
      synthesis based on human and rat RVP-1 sequences
<220> FEATURE:
<223> OTHER INFORMATION: Cyclic Peptide

<400> SEQUENCE: 268
```

```
Trp Arg Val Ser Ala Phe Ile
 1               5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Product of
      synthesis based on human and rat RVP-1 sequences
<220> FEATURE:
<223> OTHER INFORMATION: Cyclic Peptide

<400> SEQUENCE: 269

Trp Arg Val Ser Ala Phe Ile Gly
 1               5

<210> SEQ ID NO 270
<211> LENGTH: 5
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 270

Val Thr Ala Phe Leu
 1               5

<210> SEQ ID NO 271
<211> LENGTH: 6
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 271

Val Thr Ala Phe Leu Asp
 1               5

<210> SEQ ID NO 272
<211> LENGTH: 5
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 272

Gln Val Thr Ala Phe
 1               5

<210> SEQ ID NO 273
<211> LENGTH: 6
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 273

Gln Val Thr Ala Phe Leu
 1               5

<210> SEQ ID NO 274
<211> LENGTH: 7
```

```
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 274

Gln Val Thr Ala Phe Leu Asp
 1               5

<210> SEQ ID NO 275
<211> LENGTH: 6
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 275

Trp Gln Val Thr Ala Phe
 1               5

<210> SEQ ID NO 276
<211> LENGTH: 7
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 276

Trp Gln Val Thr Ala Phe Leu
 1               5

<210> SEQ ID NO 277
<211> LENGTH: 8
<212> TYPE: PRT
<213> ORGANISM: Artificial Sequence
<220> FEATURE:
<223> OTHER INFORMATION: Representative linear modulating agent based on
      claudin-5 cell adhesion recognition sequence

<400> SEQUENCE: 277

Trp Gln Val Thr Ala Phe Leu Asp
 1               5

<210> SEQ ID NO 278
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 278

Cys Val Thr Ala Phe Leu Cys
 1               5

<210> SEQ ID NO 279
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 279

Cys Val Thr Ala Phe Leu Asp Cys
```

```
1               5

<210> SEQ ID NO 280
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 280

Cys Gln Val Thr Ala Phe Cys
1               5

<210> SEQ ID NO 281
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 281

Cys Gln Val Thr Ala Phe Leu Cys
1               5

<210> SEQ ID NO 282
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 282

Cys Gln Val Thr Ala Phe Leu Asp Cys
1               5

<210> SEQ ID NO 283
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 283

Cys Trp Gln Val Thr Ala Phe Cys
1               5

<210> SEQ ID NO 284
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 284

Cys Trp Gln Val Thr Ala Phe Leu Cys
1               5

<210> SEQ ID NO 285
<211> LENGTH: 10
<212> TYPE: PRT
<213> ORGANISM: Artificial Sequence
<220> FEATURE:
<223> OTHER INFORMATION: Representative cyclic modulating agent based on
```

-continued claudin-5 cell adhesion recognition sequence

<400> SEQUENCE: 285

Cys Trp Gln Val Thr Ala Phe Leu Asp Cys
1 5 10

<210> SEQ ID NO 286
<211> LENGTH: 6
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 286

Lys Val Thr Ala Phe Asp
1 5

<210> SEQ ID NO 287
<211> LENGTH: 7
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 287

Lys Val Thr Ala Phe Leu Asp
1 5

<210> SEQ ID NO 288
<211> LENGTH: 8
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 288

Lys Val Thr Ala Phe Leu Asp Asp
1 5

<210> SEQ ID NO 289
<211> LENGTH: 7
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 289

Lys Gln Val Thr Ala Phe Asp
1 5

<210> SEQ ID NO 290
<211> LENGTH: 8
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 290

Lys Gln Val Thr Ala Phe Leu Asp
1 5

<210> SEQ ID NO 291

```
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 291

Lys Gln Val Thr Ala Phe Leu Asp Asp
 1               5

<210> SEQ ID NO 292
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 292

Lys Trp Gln Val Thr Ala Phe Asp
 1               5

<210> SEQ ID NO 293
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 293

Lys Trp Gln Val Thr Ala Phe Leu Asp
 1               5

<210> SEQ ID NO 294
<211> LENGTH: 10
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 294

Lys Trp Gln Val Thr Ala Phe Leu Asp Asp
 1               5                  10

<210> SEQ ID NO 295
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 295

Lys Val Thr Ala Phe Leu Glu
 1               5

<210> SEQ ID NO 296
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 296
```

-continued

```
Lys Val Thr Ala Phe Leu Asp Glu
 1               5

<210> SEQ ID NO 297
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 297

Lys Gln Val Thr Ala Phe Glu
 1               5

<210> SEQ ID NO 298
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 298

Lys Gln Val Thr Ala Phe Leu Glu
 1               5

<210> SEQ ID NO 299
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 299

Lys Gln Val Thr Ala Phe Leu Asp Glu
 1               5

<210> SEQ ID NO 300
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 300

Lys Trp Gln Val Thr Ala Phe Glu
 1               5

<210> SEQ ID NO 301
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 301

Lys Trp Gln Val Thr Ala Phe Leu Glu
 1               5

<210> SEQ ID NO 302
<211> LENGTH: 10
<212> TYPE: PRT
<213> ORGANISM: Artificial Sequence
<220> FEATURE:
```

```
<223> OTHER INFORMATION: Representative cyclic modulating agent based on
      claudin-5 cell adhesion recognition sequence

<400> SEQUENCE: 302

Lys Trp Gln Val Thr Ala Phe Leu Asp Glu
1               5                   10

<210> SEQ ID NO 303
<211> LENGTH: 6
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 303

Asp Val Ala Thr Phe Lys
1               5

<210> SEQ ID NO 304
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 304

Asp Val Thr Ala Phe Leu Lys
1               5

<210> SEQ ID NO 305
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 305

Asp Val Thr Ala Phe Leu Asp Lys
1               5

<210> SEQ ID NO 306
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 306

Asp Gln Val Thr Ala Phe Lys
1               5

<210> SEQ ID NO 307
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 307

Asp Gln Val Thr Ala Phe Leu Lys
1               5
```

-continued

<210> SEQ ID NO 308
<211> LENGTH: 9
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 308

Asp Gln Val Thr Ala Phe Leu Asp Lys
1 5

<210> SEQ ID NO 309
<211> LENGTH: 8
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 309

Asp Trp Gln Val Thr Ala Phe Lys
1 5

<210> SEQ ID NO 310
<211> LENGTH: 9
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 310

Asp Trp Gln Val Thr Ala Phe Leu Lys
1 5

<210> SEQ ID NO 311
<211> LENGTH: 10
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 311

Asp Trp Gln Val Thr Ala Phe Leu Asp Lys
1 5 10

<210> SEQ ID NO 312
<211> LENGTH: 7
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 312

Glu Val Thr Ala Phe Leu Lys
1 5

<210> SEQ ID NO 313
<211> LENGTH: 8
<212> TYPE: PRT
<213> ORGANISM: Artificial Sequence
<220> FEATURE:
<223> OTHER INFORMATION: Representative cyclic modulating agent based on claudin-5 cell adhesion recognition sequence

<400> SEQUENCE: 313

-continued

Glu Val Thr Ala Phe Leu Asp Lys
 1               5

<210> SEQ ID NO 314
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 314

Glu Gln Val Thr Ala Phe Lys
 1               5

<210> SEQ ID NO 315
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 315

Glu Gln Val Thr Ala Phe Leu Lys
 1               5

<210> SEQ ID NO 316
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 316

Glu Gln Val Thr Ala Phe Leu Asp Lys
 1               5

<210> SEQ ID NO 317
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 317

Glu Trp Gln Val Thr Ala Phe Lys
 1               5

<210> SEQ ID NO 318
<211> LENGTH: 9
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 318

Glu Trp Gln Val Thr Ala Phe Leu Lys
 1               5

<210> SEQ ID NO 319
<211> LENGTH: 10
<212> TYPE: PRT
<213> ORGANISM: Artificial Sequence -continued

```
<220> FEATURE:
<223> OTHER INFORMATION: Representative cyclic modulating agent based on
      claudin-5 cell adhesion recognition sequence

<400> SEQUENCE: 319

Glu Trp Gln Val Thr Ala Phe Leu Asp Lys
 1               5                   10

<210> SEQ ID NO 320
<211> LENGTH: 5
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 320

Val Thr Ala Phe Leu
 1               5

<210> SEQ ID NO 321
<211> LENGTH: 6
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 321

Val Thr Ala Phe Leu Asp
 1               5

<210> SEQ ID NO 322
<211> LENGTH: 5
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 322

Gln Val Thr Ala Phe
 1               5

<210> SEQ ID NO 323
<211> LENGTH: 6
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 323

Gln Val Thr Ala Phe Leu
 1               5

<210> SEQ ID NO 324
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 324

Gln Val Thr Ala Phe Leu Asp
 1               5
```

```
<210> SEQ ID NO 325
<211> LENGTH: 6
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 325

Trp Gln Val Thr Ala Phe
 1               5

<210> SEQ ID NO 326
<211> LENGTH: 7
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 326

Trp Gln Val Thr Ala Phe Leu
 1               5

<210> SEQ ID NO 327
<211> LENGTH: 8
<212> TYPE: PRT
<213> ORGANISM: Artificial Sequence
<220> FEATURE:
<223> OTHER INFORMATION: Representative cyclic modulating agent based on
      claudin-5 cell adhesion recognition sequence

<400> SEQUENCE: 327

Trp Gln Val Thr Ala Phe Leu Asp
 1               5

<210> SEQ ID NO 328
<211> LENGTH: 5
<212> TYPE: PRT
<213> ORGANISM: Artificial Sequence
<220> FEATURE:
<223> OTHER INFORMATION: Representative linear modulating agent based on
      claudin-6 cell adhesion recognition sequence

<400> SEQUENCE: 328

Val Thr Ala Phe Ile
 1               5

<210> SEQ ID NO 329
<211> LENGTH: 6
<212> TYPE: PRT
<213> ORGANISM: Artificial Sequence
<220> FEATURE:
<223> OTHER INFORMATION: Representative linear modulating agent based on
      claudin-6 cell adhesion recognition sequence

<400> SEQUENCE: 329

Val Thr Ala Phe Ile Gly
 1               5

<210> SEQ ID NO 330
<211> LENGTH: 5
<212> TYPE: PRT
<213> ORGANISM: Artificial Sequence
<220> FEATURE:
<223> OTHER INFORMATION: Representative linear modulating agent based on
      claudin-6 cell adhesion recognition sequence
```

-continued

```
<400> SEQUENCE: 330

Lys Val Thr Ala Phe
1               5

<210> SEQ ID NO 331
<211> LENGTH: 6
<212> TYPE: PRT
<213> ORGANISM: Artificial Sequence
<220> FEATURE:
<223> OTHER INFORMATION: Representative linear modulating agent based on
      claudin-6 cell adhesion recognition sequence

<400> SEQUENCE: 331

Lys Val Thr Ala Phe Ile
1               5

<210> SEQ ID NO 332
<211> LENGTH: 7
<212> TYPE: PRT
<213> ORGANISM: Artificial Sequence
<220> FEATURE:
<223> OTHER INFORMATION: Representative linear modulating agent based on
      claudin-6 cell adhesion recognition sequence

<400> SEQUENCE: 332

Lys Val Thr Ala Phe Ile Gly
1               5

<210> SEQ ID NO 333
<211> LENGTH: 6
<212> TYPE: PRT
<213> ORGANISM: Artificial Sequence
<220> FEATURE:
<223> OTHER INFORMATION: Representative linear modulating agent based on
      claudin-6 cell adhesion recognition sequence

<400> SEQUENCE: 333

Trp Lys Val Thr Ala Phe
1               5

<210> SEQ ID NO 334
<211> LENGTH: 7
<212> TYPE: PRT
<213> ORGANISM: Artificial Sequence
<220> FEATURE:
<223> OTHER INFORMATION: Representative linear modulating agent based on
      claudin-6 cell adhesion recognition sequence

<400> SEQUENCE: 334

Trp Lys Val Thr Ala Phe Ile
1               5

<210> SEQ ID NO 335
<211> LENGTH: 8
<212> TYPE: PRT
<213> ORGANISM: Artificial Sequence
<220> FEATURE:
<223> OTHER INFORMATION: Representative linear modulating agent based on
      claudin-6 cell adhesion recognition sequence

<400> SEQUENCE: 335

Trp Lys Val Thr Ala Phe Ile Gly
1               5

<210> SEQ ID NO 336
<211> LENGTH: 7
<212> TYPE: PRT
```

```
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 336

Cys Val Thr Ala Phe Ile Cys
 1               5

<210> SEQ ID NO 337
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 337

Cys Val Thr Ala Phe Ile Gly Cys
 1               5

<210> SEQ ID NO 338
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 338

Cys Lys Val Thr Ala Phe Cys
 1               5

<210> SEQ ID NO 339
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 339

Cys Lys Val Thr Ala Phe Ile Cys
 1               5

<210> SEQ ID NO 340
<211> LENGTH: 9
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 340

Cys Lys Val Thr Ala Phe Ile Gly Cys
 1               5

<210> SEQ ID NO 341
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 341

Cys Trp Lys Val Thr Ala Phe Cys
 1               5
```

```
<210> SEQ ID NO 342
<211> LENGTH: 9
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 342

Cys Trp Lys Val Thr Ala Phe Ile Cys
 1               5

<210> SEQ ID NO 343
<211> LENGTH: 10
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 343

Cys Trp Lys Val Thr Ala Phe Ile Gly Cys
 1               5                  10

<210> SEQ ID NO 344
<211> LENGTH: 6
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 344

Lys Val Thr Ala Phe Asp
 1               5

<210> SEQ ID NO 345
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 345

Lys Val Thr Ala Phe Ile Asp
 1               5

<210> SEQ ID NO 346
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 346

Lys Val Thr Ala Phe Ile Gly Asp
 1               5

<210> SEQ ID NO 347
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence
```

```
<400> SEQUENCE: 347

Lys Lys Val Thr Ala Phe Asp
  1               5

<210> SEQ ID NO 348
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 348

Lys

```
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 353

Lys Val Thr Ala Phe Ile Glu
        1               5

<210> S

-continued

```
 1               5

<210> SEQ ID NO 359
<211> LENGTH: 9
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 359

Lys Trp Lys Val Thr Ala Phe Ile Glu
 1               5

<210> SEQ ID NO 360
<211> LENGTH: 10
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 360

Lys Trp Lys Val Thr Ala Phe Ile Gly Glu
 1               5                  10

<210> SEQ ID NO 361
<211> LENGTH: 6
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 361

Asp Val Ala Thr Phe Lys
 1               5

<210> SEQ ID NO 362
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 362

Asp Val Thr Ala Phe Ile Lys
 1               5

<210> SEQ ID NO 363
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 363

Asp Val Thr Ala Phe Ile Gly Lys
 1               5

<210> SEQ ID NO 364
<211> LENGTH: 7
<212> TYPE: PRT
<213> ORGANISM: Artificial Sequence
<220> FEATURE:
<223> OTHER INFORMATION: Representative cyclic modulating agent based on
```

```
      claudin-6 cell adhesion recognition sequence

<400> SEQUENCE: 364

Asp Lys Val Thr Ala Phe Lys
 1               5

<210> SEQ ID NO 365
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 365

Asp Lys Val Thr Ala Phe Ile Lys
 1               5

<210> SEQ ID NO 366
<211> LENGTH: 9
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 366

Asp Lys Val Thr Ala Phe Ile Gly Lys
 1               5

<210> SEQ ID NO 367
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 367

Asp Trp Lys Val Thr Ala Phe Lys
 1               5

<210> SEQ ID NO 368
<211> LENGTH: 9
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 368

Asp Trp Lys Val Thr Ala Phe Ile Lys
 1               5

<210> SEQ ID NO 369
<211> LENGTH: 10
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 369

Asp Trp Lys Val Thr Ala Phe Ile Gly Lys
 1               5                  10

<210> SEQ ID NO 370
```

-continued

```
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 370

Glu Val Thr Ala Phe Ile Lys
 1               5

<210> SEQ ID NO 371
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 371

Glu Val Thr Ala Phe Ile Gly Lys
 1               5

<210> SEQ ID NO 372
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 372

Glu Lys Val Thr Ala Phe Lys
 1               5

<210> SEQ ID NO 373
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 373

Glu Lys Val Thr Ala Phe Ile Lys
 1               5

<210> SEQ ID NO 374
<211> LENGTH: 9
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 374

Glu Lys Val Thr Ala Phe Ile Gly Lys
 1               5

<210> SEQ ID NO 375
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 375
```

-continued

```
Glu Trp Lys Val Thr Ala Phe Lys
 1               5

<210> SEQ ID NO 376
<211> LENGTH: 9
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 376

Glu Trp Lys Val Thr Ala Phe Ile Lys
 1               5

<210> SEQ ID NO 377
<211> LENGTH: 10
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 377

Glu Trp Lys Val Thr Ala Phe Ile Gly Lys
 1               5                   10

<210> SEQ ID NO 378
<211> LENGTH: 5
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 378

Val Thr Ala Phe Ile
 1               5

<210> SEQ ID NO 379
<211> LENGTH: 6
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 379

Val Thr Ala Phe Ile Gly
 1               5

<210> SEQ ID NO 380
<211> LENGTH: 5
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 380

Lys Val Thr Ala Phe
 1               5

<210> SEQ ID NO 381
<211> LENGTH: 6
<212> TYPE: PRT
<213> ORGANISM: Artificial Sequence
<220> FEATURE:
```

```
<223> OTHER INFORMATION: Representative cyclic modulating agent based on
      claudin-6 cell adhesion recognition sequence

<400> SEQUENCE: 381

Lys Val Thr Ala Phe Ile
 1               5

<210> SEQ ID NO 382
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 382

Lys Val Thr Ala Phe Ile Gly
 1               5

<210> SEQ ID NO 383
<211> LENGTH: 6
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 383

Trp Lys Val Thr Ala Phe
 1               5

<210> SEQ ID NO 384
<211> LENGTH: 7
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 384

Trp Lys Val Thr Ala Phe Ile
 1               5

<210> SEQ ID NO 385
<211> LENGTH: 8
<212> TYPE: PRT
<213> ORGANISM: Artificial Sequence
<220> FEATURE:
<223> OTHER INFORMATION: Representative cyclic modulating agent based on
      claudin-6 cell adhesion recognition sequence

<400> SEQUENCE: 385

Trp Lys Val Thr Ala Phe Ile Gly
 1               5

<210> SEQ ID NO 386
<211> LENGTH: 4
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 386

Met Ser Ser Tyr
 1
```

-continued

```
<210> SEQ ID NO 387
<211> LENGTH: 5
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 387

Met Ser Ser Tyr Ala
1               5

<210> SEQ ID NO 388
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 388

Met Ser Ser Tyr Ala Gly
1               5

<210> SEQ ID NO 389
<211> LENGTH: 5
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 389

Gln Met Ser Ser Tyr
1               5

<210> SEQ ID NO 390
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 390

Gln Met Ser Ser Tyr Ala
1               5

<210> SEQ ID NO 391
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 391

Gln Met Ser Ser Tyr Ala Gly
1               5

<210> SEQ ID NO 392
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 392
```

```
Trp Gln Met Ser Ser Tyr
1               5

<210> SEQ ID NO 393
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 393

Trp Gln Met Ser Ser Tyr Ala
1               5

<210> SEQ ID NO 394
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 394

Trp Gln Met Ser Ser Tyr Ala Gly
1               5

<210> SEQ ID NO 395
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 395

Cys Met Ser Ser Tyr Cys
1               5

<210> SEQ ID NO 396
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 396

Cys Met Ser Ser Tyr Ala Cys
1               5

<210> SEQ ID NO 397
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 397

Cys Met Ser Ser Tyr Ala Gly Cys
1               5

<210> SEQ ID NO 398
<211> LENGTH: 7
<212> TYPE: PRT
<213> ORGANISM: Artificial Sequence
```

```
<220> FEATURE:
<223> OTHER INFORMATION: Representative linear modulating agent based on
      claudin-7 cell adhesion recognition sequence

<400> SEQUENCE: 398

Cys Gln Met Ser Ser Tyr Cys
1               5

<210> SEQ ID NO 399
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 399

Cys Gln Met Ser Ser Tyr Ala Cys
1               5

<210> SEQ ID NO 400
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 400

Cys Gln Met Ser Ser Tyr Ala Gly Cys
1               5

<210> SEQ ID NO 401
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 401

Cys Trp Gln Met Ser Ser Tyr Cys
1               5

<210> SEQ ID NO 402
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 402

Cys Trp Gln Met Ser Ser Tyr Ala Cys
1               5

<210> SEQ ID NO 403
<211> LENGTH: 10
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 403

Cys Trp Gln Met Ser Ser Tyr Ala Gly Cys
1               5                   10
```

-continued

```
<210> SEQ ID NO 404
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 404

Lys Met Ser Ser Tyr Asp
 1               5

<210> SEQ ID NO 405
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 405

Lys Met Ser Ser Tyr Ala Asp
 1               5

<210> SEQ ID NO 406
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 406

Lys Met Ser Ser Tyr Ala Gly Asp
 1               5

<210> SEQ ID NO 407
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 407

Lys Gln Met Ser Ser Tyr Asp
 1               5

<210> SEQ ID NO 408
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 408

Lys Gln Met Ser Ser Tyr Ala Asp
 1               5

<210> SEQ ID NO 409
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence
```

-continued

<400> SEQUENCE: 409

Lys Gln Met Ser Ser Tyr Ala Gly Asp
 1               5

<210> SEQ ID NO 410
<211> LENGTH: 8
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 410

Lys Trp Gln Met Ser Ser Tyr Asp
 1               5

<210> SEQ ID NO 411
<211> LENGTH: 9
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 411

Lys Trp Gln Met Ser Ser Tyr Ala Asp
 1               5

<210> SEQ ID NO 412
<211> LENGTH: 10
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 412

Lys Trp Gln Met Ser Ser Tyr Ala Gly Asp
 1               5                   10

<210> SEQ ID NO 413
<211> LENGTH: 6
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 413

Lys Met Ser Ser Tyr Glu
 1               5

<210> SEQ ID NO 414
<211> LENGTH: 7
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 414

Lys Met Ser Ser Tyr Ala Glu
 1               5

<210> SEQ ID NO 415
<211> LENGTH: 8
<212> TYPE: PRT

```
<213> ORGANISM: Artificial Sequence
<220> FEATURE:
<223> OTHER INFORMATION: Representative linear modulating agent based on
      claudin-7 cell adhesion recognition sequence

<400> SEQUENCE: 415

Lys Met Ser Ser Tyr Ala Gly Glu
1               5

<210> SEQ ID NO 416
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 416

Lys Gln Met Ser Ser Tyr Glu
1               5

<210> SEQ ID NO 417
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 417

Lys Gln Met Ser Ser Tyr Ala Glu
1               5

<210> SEQ ID NO 418
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 418

Lys Gln Met Ser Ser Tyr Ala Gly Glu
1               5

<210> SEQ ID NO 419
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 419

Lys Trp Gln Met Ser Ser Tyr Glu
1               5

<210> SEQ ID NO 420
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 420

Lys Trp Gln Met Ser Ser Tyr Ala Glu
1               5
```

<210> SEQ ID NO 421
<211> LENGTH: 10
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 421

Lys Trp Gln Met Ser Ser Tyr Ala Gly Glu
 1               5                  10

<210> SEQ ID NO 422
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 422

Asp Met Ser Ser Tyr Lys
 1               5

<210> SEQ ID NO 423
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 423

Asp Met Ser Ser Tyr Ala Lys
 1               5

<210> SEQ ID NO 424
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 424

Asp Met Ser Ser Tyr Ala Gly Lys
 1               5

<210> SEQ ID NO 425
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 425

Asp Gln Met Ser Ser Tyr Lys
 1               5

<210> SEQ ID NO 426
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

```
<400> SEQUENCE: 426

Asp Gln Met Ser Ser Tyr Ala Lys
 1               5

<210> SEQ ID NO 427
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 427

Asp Gln Met Ser Ser Tyr Ala Gly Lys
 1               5

<210> SEQ ID NO 428
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 428

Asp Trp Gln Met Ser Ser Tyr Lys
 1               5

<210> SEQ ID NO 429
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 429

Asp Trp Gln Met Ser Ser Tyr Ala Lys
 1               5

<210> SEQ ID NO 430
<211> LENGTH: 10
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 430

Asp Trp Gln Met Ser Ser Tyr Ala Gly Lys
 1               5                  10

<210> SEQ ID NO 431
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 431

Glu Met Ser Ser Tyr Lys
 1               5

<210> SEQ ID NO 432
<211> LENGTH: 7
```

```
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 432

Glu Met Ser Ser Tyr Ala Lys
 1               5

<210> SEQ ID NO 433
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 433

Glu Met Ser Ser Tyr Ala Gly Lys
 1               5

<210> SEQ ID NO 434
<211> LENGTH: 7
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 434

Glu Gln Met Ser Ser Tyr Lys
 1               5

<210> SEQ ID NO 435
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 435

Glu Gln Met Ser Ser Tyr Ala Lys
 1               5

<210> SEQ ID NO 436
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 436

Glu Gln Met Ser Ser Tyr Ala Gly Lys
 1               5

<210> SEQ ID NO 437
<211> LENGTH: 8
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 437

Glu Trp Gln Met Ser Ser Tyr Lys
```

```
<210> SEQ ID NO 438
<211> LENGTH: 9
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 438

Glu Trp Gln Met Ser Ser Tyr Ala Lys
1               5

<210> SEQ ID NO 439
<211> LENGTH: 10
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 439

Glu Trp Gln Met Ser Ser Tyr Ala Gly Lys
1               5                   10

<210> SEQ ID NO 440
<211> LENGTH: 5
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 440

Met Ser Ser Tyr Ala
1               5

<210> SEQ ID NO 441
<211> LENGTH: 6
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 441

Met Ser Ser Tyr Ala Gly
1               5

<210> SEQ ID NO 442
<211> LENGTH: 5
<212> TYPE: PRT
<213> ORGANISM: Artificial Sequence
<220> FEATURE:
<223> OTHER INFORMATION: Representative linear modulating agent based on
      claudin-7 cell adhesion recognition sequence

<400> SEQUENCE: 442

Gln Met Ser Ser Tyr
1               5

<210> SEQ ID NO 443
<211> LENGTH: 6
<212> TYPE: PRT
<213> ORGANISM: Artificial Sequence
<220> FEATURE:
<223> OTHER INFORMATION: Representative linear modulating agent based on
```

-continued claudin-7 cell adhesion recognition sequence

<400> SEQUENCE: 443

Gln Met Ser Ser Tyr Ala
1 5

<210> SEQ ID NO 444
<211> LENGTH: 7
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 444

Gln Met Ser Ser Tyr Ala Gly
1 5

<210> SEQ ID NO 445
<211> LENGTH: 6
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 445

Trp Gln Met Ser Ser Tyr
1 5

<210> SEQ ID NO 446
<211> LENGTH: 7
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 446

Trp Gln Met Ser Ser Tyr Ala
1 5

<210> SEQ ID NO 447
<211> LENGTH: 8
<212> TYPE: PRT
<213> ORGANISM: Artificial Sequence
<220> FEATURE:
<223> OTHER INFORMATION: Representative linear modulating agent based on claudin-7 cell adhesion recognition sequence

<400> SEQUENCE: 447

Trp Gln Met Ser Ser Tyr Ala Gly
1 5

<210> SEQ ID NO 448
<211> LENGTH: 6
<212> TYPE: PRT
<213> ORGANISM: Artificial Sequence
<220> FEATURE:
<223> OTHER INFORMATION: Representative linear modulating agent based on claudin-8 cell adhesion recognition sequence

<400> SEQUENCE: 448

Val Ser Ala Phe Ile Glu
1 5

<210> SEQ ID NO 449

```
<211> LENGTH: 7
<212> TYPE: PRT
<213> ORGANISM: Artificial Sequence
<220> FEATURE:
<223> OTHER INFORMATION: Representative linear modulating agent based on
      claudin-8 cell adhesion recognition sequence

<400> SEQUENCE: 449

Arg Val Ser Ala Phe Ile Glu
 1               5

<210> SEQ ID NO 450
<211> LENGTH: 8
<212> TYPE: PRT
<213> ORGANISM: Artificial Sequence
<220> FEATURE:
<223> OTHER INFORMATION: Representative linear modulating agent based on
      claudin-8 cell adhesion recognition sequence

<400> SEQUENCE: 450

Trp Arg Val Ser Ala Phe Ile Glu
 1               5

<210> SEQ ID NO 451
<211> LENGTH: 8
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 451

Cys Val Ser Ala Phe Ile Glu Cys
 1               5

<210> SEQ ID NO 452
<211> LENGTH: 9
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 452

Cys Arg Val Ser Ala Phe Ile Glu Cys
 1               5

<210> SEQ ID NO 453
<211> LENGTH: 10
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 453

Cys Trp Arg Val Ser Ala Phe Ile Glu Cys
 1               5                  10

<210> SEQ ID NO 454
<211> LENGTH: 8
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 454
```

-continued

```
Lys Val Ser Ala Phe Ile Glu Asp
 1               5

<210> SEQ ID NO 455
<211> LENGTH: 9
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 455

Lys Arg Val Ser Ala Phe Ile Glu Asp
 1               5

<210> SEQ ID NO 456
<211> LENGTH: 10
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 456

Lys Trp Arg Val Ser Ala Phe Ile Glu Asp
 1               5                   10

<210> SEQ ID NO 457
<211> LENGTH: 8
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 457

Lys Val Ser Ala Phe Ile Glu Glu
 1               5

<210> SEQ ID NO 458
<211> LENGTH: 9
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 458

Lys Arg Val Ser Ala Phe Ile Glu Glu
 1               5

<210> SEQ ID NO 459
<211> LENGTH: 10
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 459

Lys Trp Arg Val Ser Ala Phe Ile Glu Glu
 1               5                   10

<210> SEQ ID NO 460
<211> LENGTH: 8
<212> TYPE: PRT
<213> ORGANISM: Artificial Sequence
<220> FEATURE:
```

-continued

<223> OTHER INFORMATION: Representative cyclic modulating agent based on claudin-8 cell adhesion recognition sequence

<400> SEQUENCE: 460

Asp Val Ser Ala Phe Ile Glu Lys
 1              5

<210> SEQ ID NO 461
<211> LENGTH: 9
<212> TYPE: PRT
<213> ORGANISM: Artificial Sequence
<220> FEATURE:
<223> OTHER INFORMATION: Representative cyclic modulating agent based on claudin-8 cell adhesion recognition sequence

<400> SEQUENCE: 461

Asp Arg Val Ser Ala Phe Ile Glu Lys
 1              5

<210> SEQ ID NO 462
<211> LENGTH: 10
<212> TYPE: PRT
<213> ORGANISM: Artificial Sequence
<220> FEATURE:
<223> OTHER INFORMATION: Representative cyclic modulating agent based on claudin-8 cell adhesion recognition sequence

<400> SEQUENCE: 462

Asp Trp Arg Val Ser Ala Phe Ile Glu Lys
 1              5                   10

<210> SEQ ID NO 463
<211> LENGTH: 8
<212> TYPE: PRT
<213> ORGANISM: Artificial Sequence
<220> FEATURE:
<223> OTHER INFORMATION: Representative cyclic modulating agent based on claudin-8 cell adhesion recognition sequence

<400> SEQUENCE: 463

Glu Val Ser Ala Phe Ile Glu Lys
 1              5

<210> SEQ ID NO 464
<211> LENGTH: 9
<212> TYPE: PRT
<213> ORGANISM: Artificial Sequence
<220> FEATURE:
<223> OTHER INFORMATION: Representative cyclic modulating agent based on claudin-8 cell adhesion recognition sequence

<400> SEQUENCE: 464

Glu Arg Val Ser Ala Phe Ile Glu Lys
 1              5

<210> SEQ ID NO 465
<211> LENGTH: 10
<212> TYPE: PRT
<213> ORGANISM: Artificial Sequence
<220> FEATURE:
<223> OTHER INFORMATION: Representative cyclic modulating agent based on claudin-8 cell adhesion recognition sequence

<400> SEQUENCE: 465

Glu Trp Arg Val Ser Ala Phe Ile Glu Lys
 1              5                   10

```
<210> SEQ ID NO 466
<211> LENGTH: 6
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 466

Val Ser Ala Phe Ile Glu
1               5

<210> SEQ ID NO 467
<211> LENGTH: 7
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 467

Arg Val Ser Ala Phe Ile Glu
1               5

<210> SEQ ID NO 468
<211> LENGTH: 8
<212> TYPE: PRT
<213> ORGANISM: Artificial Sequence
<220> FEATURE:
<223> OTHER INFORMATION: Representative cyclic modulating agent based on
      claudin-8 cell adhesion recognition sequence

<400> SEQUENCE: 468

Trp Arg Val Ser Ala Phe Ile Glu
1               5

<210> SEQ ID NO 469
<211> LENGTH: 30
<212> TYPE: PRT
<213> ORGANISM: Mus musculus

<400> SEQUENCE: 469

Pro Met Trp Arg Val Ser Ala Phe Ile Gly Ser Ser Ile Ile Thr Ala
1               5                   10                  15

Gln Ile Thr Trp Glu Gly Leu Trp Met Asn Cys Val Val Gln
            20                  25                  30

<210> SEQ ID NO 470
<211> LENGTH: 30
<212> TYPE: PRT
<213> ORGANISM: Mus musculus

<400> SEQUENCE: 470

Pro Met Trp Gln Val Thr Ala Phe Leu Asp His Asn Ile Val Thr Ala
1               5                   10                  15

Gln Thr Thr Trp Lys Gly Leu Trp Met Ser Cys Val Val Gln
            20                  25                  30

<210> SEQ ID NO 471
<211> LENGTH: 30
<212> TYPE: PRT
<213> ORGANISM: Homo sapien

<400> SEQUENCE: 471

Pro Met Trp Gln Val Thr Ala Phe Leu Asp His Asn Ile Val Thr Ala
1               5                   10                  15
```

-continued

```
Gln Thr Thr Trp Lys Gly Leu Trp Met Ser Cys Val Val Gln
            20                  25                  30

<210> SEQ ID NO 472
<211> LENGTH: 30
<212> TYPE: PRT
<213> ORGANISM: Mus musculus

<400> SEQUENCE: 472

Pro Met Trp Lys Val Thr Ala Phe Ile Gly Asn Ser Ile Val Val Ala
 1               5                  10                  15

Gln Met Val Trp Glu Gly Leu Trp Met Ser Cys Val Val Gln
            20                  25                  30

<210> SEQ ID NO 473
<211> LENGTH: 30
<212> TYPE: PRT
<213> ORGANISM: Mus musculus

<400> SEQUENCE: 473

Pro Gln Trp Gln Met Ser Ser Tyr Ala Gly Asp Asn Ile Ile Thr Ala
 1               5                  10                  15

Gln Ala Met Tyr Lys Gly Leu Trp Met Glu Cys Val Thr Gln
            20                  25                  30

<210> SEQ ID NO 474
<211> LENGTH: 30
<212> TYPE: PRT
<213> ORGANISM: Mus musculus

<400> SEQUENCE: 474

Pro Gln Trp Arg Val Ser Ala Phe Ile Glu Ser Asn Ile Val Val Phe
 1               5                  10                  15

Glu Asn Arg Trp Glu Gly Leu Trp Met Asn Cys Met Arg His
            20                  25                  30

<210> SEQ ID NO 475
<211> LENGTH: 10
<212> TYPE: PRT
<213> ORGANISM: Artificial Sequence
<220> FEATURE:
<223> OTHER INFORMATION: Representative linear modulating agent based on
      claudin-1 cell adhesion recognition sequence used in Example 5 to
      demonstrate electrical resistance across cell monolayer

<400> SEQUENCE: 475

Trp Lys Ile Tyr Ser Tyr Ala Gly Asp Asn
 1               5                  10

<210> SEQ ID NO 476
<211> LENGTH: 9
<212> TYPE: PRT
<213> ORGANISM: Artificial Sequence
<220> FEATURE:
<223> OTHER INFORMATION: Representative linear modulating agent based on
      claudin-1 cell adhesion recognition sequence

<400> SEQUENCE: 476

Trp Lys Ile Tyr Ser Tyr Ala Gly Asn
 1               5

<210> SEQ ID NO 477
<211> LENGTH: 9
<212> TYPE: PRT
```

```
<213> ORGANISM: Artificial Sequence
<220> FEATURE:
<223> OTHER INFORMATION: Representative cell adhesion recognition
      sequence which is bound by JAM, a member of the immunoglobulin
      supergene family

<400> SEQUENCE: 477

Ser Phe Thr Ile Asp Pro Lys Ser Gly
1               5

<210> SEQ ID NO 478
<211> LENGTH: 10
<212> TYPE: PRT
<213> ORGANISM: Artificial Sequence
<220> FEATURE:
<223> OTHER INFORMATION: Representative occuldin cell adhesion
      recognition sequence

<400> SEQUENCE: 478

Gln Tyr Leu Tyr His Tyr Cys Val Val Asp
1               5                   10

<210> SEQ ID NO 479
<211> LENGTH: 9
<212> TYPE: PRT
<213> ORGANISM: Artificial Sequence
<220> FEATURE:
<223> OTHER INFORMATION: Representative OB-cadherin cell adhesion
      recognition sequence

<400> SEQUENCE: 479

Ile Phe Val Ile Asp Asp Lys Ser Gly
1               5

<210> SEQ ID NO 480
<211> LENGTH: 8
<212> TYPE: PRT
<213> ORGANISM: Unknown
<220> FEATURE:
<221> NAME/KEY: MOD_RES
<222> LOCATION: 3,4,7
<223> OTHER INFORMATION: Where Xaa is an independently selected amino
      acid residue
<220> FEATURE:
<223> OTHER INFORMATION: Claudin-5 CAR Cell Adhesion Recognition
      Sequence

<400> SEQUENCE: 480 rp Gln Xaa Xaa Ala Phe Xaa Asp
1               5
```

COMPOUNDS AND METHODS FOR MODULATING CLAUDIN-MEDIATED FUNCTIONS

CROSS-REFERENCE TO RELATED APPLICATION

This application is a continuation-in-part of U.S. application Ser. No. 09/185,908, filed Nov. 3, 1998.

TECHNICAL FIELD

The present invention relates generally to methods for regulating claudin-mediated processes, and more particularly to the use of modulating agents comprising a claudin cell adhesion recognition sequence and/or an antibody that specifically recognizes such a sequence for inhibiting functions such as cell adhesion and the formation of tissue permeability barriers.

BACKGROUND OF THE INVENTION

Cell adhesion is a complex process that is important for maintaining tissue integrity and generating physical and permeability barriers within the body. All tissues are divided into discrete compartments, each of which is composed of a specific cell type that adheres to similar cell types. Such adhesion triggers the formation of intercellular junctions (i.e., readily definable contact sites on the surfaces of adjacent cells that are adhering to one another), also known as tight junctions, gap junctions, spot desmosomes and belt desmosomes. The formation of such junctions gives rise to physical and permeability barriers that restrict the free passage of cells and other biological substances from one tissue compartment to another. For example, the blood vessels of all tissues are composed of endothelial cells. In order for components in the blood to enter a given tissue compartment, they must first pass from the lumen of a blood vessel through the barrier formed by the endothelial cells of that vessel. Similarly, in order for substances to enter the body via the gut, the substances must first pass through a barrier formed by the epithelial cells of that tissue. To enter the blood via the skin, both epithelial and endothelial cell layers must be crossed.

Cell adhesion is mediated by specific cell surface adhesion molecules (CAMs). There are many different families of CAMs, including the immunoglobulin, integrin, selectin and cadherin superfamilies, and each cell type expresses a unique combination of these molecules. Cadherins are a rapidly expanding family of calcium-dependent CAMs (Munro et al., In: *Cell Adhesion and Invasion in Cancer Metastasis*, P. Brodt, ed., pp. 17–34, R G Landes Co., Austin Tex., 1996). The cadherins (abbreviated CADs) are membrane glycoproteins that generally promote cell adhesion through homophilic interactions (a CAD on the surface of one cell binds to an identical CAD on the surface of another cell). Cadherins have been shown to regulate epithelial, endothelial, neural and cancer cell adhesion, with different CADs expressed on different cell types. For example, N (neural)-cadherin is predominantly expressed by neural cells, endothelial cells and a variety of cancer cell types. E (epitlielial)-cadherin is predominantly expressed by epithelial cells. VE (vascular endothelial)-cadherirn is predominantly expressed by endothelial cells. Other CADs are P (placental)-cadherin. which is found in human skin, and R (retinal)-cadherin. A detailed discussion of the cadherins is provided in Munro S B et al. 1996, In: *Cell Adhesion and Invasion in Cancer Metastasis*, P. Brodt, ed., pp.17–34 (R G Landes Company, Austin Tex.) and Lampugnani and Dejana, *Curr. Opin. Cell Biol.* 9:674–682, 1997.

CAD-mediated cell adhesion triggers a cascade of events that lead to the formation of intercellular junctions, and ultimately to the establishment of permeability barriers between tissue compartments. The intercellular junction that is directly responsible for the creation of permeability barriers that prevent the diffusion of solutes through paracellular spaces is known as the tight junction, or zonula occludens (Anderson and van Itallie, *Am. J. Physiol.* 269:G467-G475, 1995; Lampugnani and Dejana, *Curr. Opin. Cell Biol.* 9:674–682, 1997).

The transmembrane component of tight junctions that has been the most studied is occludin (Furuse et al., *J. Cell Biol.* 123:1777–1788, 1993; Furuse et al., *J. Cell Sci.* 109:429–435, 1996). This protein appears to be expressed by all endothelial cell types, as well as by most epithelial cell types. Occludin is an integral membrane protein that is composed of two extracellular domains, four hydrophobic domains that transverse the plasma membrane, and three cytoplasmic domains, and the structures of all known mammalian occludins are similar (Ando-Akatsuka et al., *J. Biol. Chem.* 133:43–47, 1996). Occludin is believed to be directly involved in cell adhesion and the formation of tight junctions (Furuse et al., *J. Cell Sci.* 109:429–435, 1996; Chen et al., *J. Cell Biol.* 138:891–899, 1997). It has been proposed that occludin promotes cell adhesion through homophilic interactions (an occludin on the surface of one cell binds to an identical occludin on the surface of another cell). A detailed discussion of occludin structure and function is provided by Lampugnani and Dejana, *Curr. Opin. Cell Biol.* 9:674–682, 1997.

More recently, a second family of tight junction components has been identified. Claudins are transmembrane proteins that appear to be directly involved in cell adhesion and the formation of tight junctions (Furuse et al., *J. Cell Biology* 141:1539–1550, 1998; Morita et al., *Proc. Natl. Acad. Sci. USA* 96:511–516, 1999). Other previously described proteins that appear to be members of the claudin family include RVP-1 (Briehl and Miesfeld, *Molecular Endocrinology* 5:1381–1388, 1991; Katahira et al., *J. Biological Chemistry* 272:26652–26656, 1997), the *Clostridium perfringens* enterotoxin receptor (CPE-R; see Katahira et al., *J. Cell Biology* 136:1239–1247, 1997; Katahira et al., *J. Biological Chemistry* 272:26652–26656, 1997) and TMVCF (transmembrane protein deleted in Velo-cardio-facial syndrome; Sirotkin et al., *Genomics* 42:245–51, 1997).

Based on hydrophobicity analysis, all claudins appear to be approximately 22 kD and contain four hydrophobic domains that transverse the plasma membrane. It has been proposed that claudins promote cell adhesion through homophilic interactions (a claudin on the surface of one cell binds to an identical claudin on the surface of another cell) or heterophilic interactions, possibly with occludin.

Although cell adhesion is required for certain normal physiological functions, there are situations in which the level of cell adhesion is undesirable. For example, many pathologies (such as autoimmune diseases and inflammatory diseases) involve abnormal cellular adhesion. Cell adhesion may also play a role in graft rejection. In such circumstances, modulation of cell adhesion may be desirable.

In addition, permeability barriers arising from cell adhesion create difficulties for the delivery of drugs to specific tissues and tumors within the body. For example, skin patches are a convenient tool for administering drugs through the skin. However, the use of skin patches has been limited to small, hydrophobic molecules because of the epithelial and endothelial cell barriers. Similarly, endothelial cells render the blood capillaries largely impermeable to drugs, and the blood/brain barrier has hampered the targeting of drugs to the central nervous system. In addition, many solid tumors develop internal barriers that limit the delivery of anti-tumor drugs and antibodies to inner cells.

Attempts to facilitate the passage of drugs across such barriers generally rely on specific receptors or carrier proteins that transport molecules across barriers in vivo. However, such methods are often inefficient, due to low endogenous transport rates or to the poor functioning of a carrier protein with drugs. While improved efficiency has been achieved using a variety of chemical agents that disrupt cell adhesion, such agents are typically associated with undesirable side-effects, may require invasive procedures for administration and may result in irreversible effects.

Accordingly, there is a need in the art for compounds that modulate cell adhesion and improve drug delivery across permeability barriers without such disadvantages. The present invention fulfills this need and further provides other related advantages.

SUMMARY OF THE INVENTION

The present invention provides compounds and methods for modulating claudin-mediated cell adhesion and the formation of permeability barriers. Within certain aspects, the present invention provides cell adhesion modulating agents that inhibit or enhance claudin-mediated cell adhesion. Certain modulating agents (a) comprise a claudin CAR sequence; and (b) contain 3–16 amino acid residues linked by peptide bonds. Other modulating agents (a) comprise at least five or seven consecutive amino acid residues of a claudin CAR sequence having the formula:

Trp-Lys/Arg/Gln-Aaa-Baa-Ser/Ala-Tyr/Phe-Caa-
Gly/Asp/Glu    (SEQ ID NO:1)

wherein Aaa, Baa and Caa indicate independently selected amino acid residues; Lys/Arg/Gln is an amino acid that is lysine, arginine or glutamine; Ser/Ala is an amino acid that is serine or alanine; Tyr/Phe is an amino acid that is tyrosine or phenylalanine; and Gly/Asp/Glu is an amino acid that is glycine, aspartic acid or glutamic acid; and (b) contain no more than 50 consecutive amino acid residues present within the claudin. Still other modulating agents (a) comprise at least eight consecutive amino acid residues of a claudin CAR sequence having the above formula; and (b) contain no more than 50 consecutive amino acid residues present within the claudin.

Within certain embodiments, a modulating agent as described above comprises a claudin CAR sequence that is present within a cyclic peptide. The cyclic peptide may have the formula:

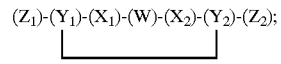

wherein W is a tetrapeptide selected from the group consisting of IYSY (SEQ ID NO:2), TSSY (SEQ ID NO:3), VTAF (SEQ ID NO:4), VSAF (SEQ ID NO:5) and MSSY (SEQ ID NO:386); wherein $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds. In certain embodiments, $Y_1$ comprises an N-acetyl group and/or $Y_2$ comprises a C-terminal amide group. $Y_1$ and $Y_2$ may be covalently linked via any suitable bond, including a disulfide bond, an amide bond or a thioether bond.

The present invention further provides, within other aspects, polynucleotides encoding a modulating agent as provided above, expression vectors comprising such a polynucleotide, and host cells transformed or transfected with such an expression vector.

Within further aspects, the present invention provides modulating agents that comprise an antibody or antigen-binding fragment thereof that specifically binds to a claudin CAR sequence and modulates a claudin-mediated function, wherein the claudin CAR sequence has the formula:

Trp-Lys/Arg/Gln-Aaa-Baa-Ser/Ala-Tyr/Phe-Caa-
Gly/Asp/Glu    (SEQ ID NO:1)

wherein Aaa, Baa and Caa indicate independently selected amino acid residues; Lys/Arg/Gln is an amino acid that is lysine, arginine or glutamine; Ser/Ala is an amino acid that is serine or alanine; Tyr/Phe is an amino acid that is tyrosine or phenylalanine; and Gly/Asp/Glu is an amino acid that is glycine, aspartic acid or glutamic acid.

The present invention further provides modulating agents comprising a mimetic of a claudin CAR sequence that comprises at least three or five consecutive amino acid residues of a claudin CAR sequence having the formula Trp-Lys/Arg/Gln-Aaa-Baa-Ser/Ala-Tyr/Phe-Caa-
Gly/Asp/Glu    (SEQ ID NO:1)

wherein Aaa, Baa and Caa indicate independently selected amino acid residues; Lys/Arg/Gln is an amino acid that is lysine, arginine or glutamine; Ser/Ala is an amino acid that is serine or alanine; Tyr/Phe is an amino acid that is tyrosine or phenylalanine; and Gly/Asp/Glu is an amino acid that is glycine, aspartic acid or glutamic acid; and wherein the mimetic is capable of modulating a claudin-mediated function.

Within other aspects, modulating agents as described above may be linked to one or more of a drug, a detectable marker, a targeting agent and/or a support material. Alternatively, or in addition, modulating agents as described above may further comprise one or more of: (a) a cell adhesion recognition sequence that is bound by an adhesion molecule other than a claudin, wherein the cell adhesion recognition sequence is separated from any claudin CAR sequence(s) by a linker; and/or (b) an antibody or antigen-binding fragment thereof that specifically binds to a cell adhesion recognition sequence bound by an adhesion molecule other than a claudin. Such adhesion molecules may be selected from the group consisting of integrins, cadherins, occludin, N-CAM, JAM, PE-CAM, desmogleins, desmocollins, fibronectin, laminin and other extracellular matrix proteins.

Within certain specific aspects, a modulating agent may comprise one or more claudin-1 CAR sequences selected from the group consisting of: IYSY (SEQ ID NO:2), IYSYA (SEQ ID NO:27), IYSYAG (SEQ ID NO:28), KIYSY (SEQ ID NO:29), KIYSYA (SEQ ID NO:30), KIYSYAG (SEQ ID NO:31), WKIYSY (SEQ ID NO:32), WKIYSYA (SEQ ID NO:33) and WKIYSYAG (SEQ ID NO:34). Such CAR sequences may be present within a cyclic peptide, such as:

CIYSYC (SEQ ID NO:59), CIYSYAC (SEQ ID NO:60), CIYSYAGC (SEQ ID NO:61), CKIYSYC (SEQ ID NO:62), CKIYSYAC (SEQ ID NO:63), CKIYSYAGC (SEQ ID NO:64), CWKIYSYC (SEQ ID NO:65), CWKIYSYAC (SEQ ID NO:66), CWKIYSYAGC (SEQ ID NO:67), KIYSYD (SEQ ID NO:68), KIYSYAD (SEQ ID NO:69), KIYSYAGD (SEQ ID NO:70), KKIYSYD (SEQ ID NO:71), KKIYSYAD (SEQ ID NO:72), KKIYSYAGD (SEQ ID NO:73), KWKIYSYD (SEQ ID NO:74), KWKIYSYAD (SEQ ID NO:75), KWKIYSYAGD (SEQ ID NO:76), KIYSYE (SEQ ID NO:77), KIYSYAE (SEQ ID NO:78), KIYSYAGE (SEQ ID NO:79), KKIYSYE (SEQ ID NO:80), KKIYSYAE (SEQ ID NO:81), KKIYSYAGE (SEQ ID NO:82), KWKIYSYE (SEQ ID NO:83), KWKIYSYAE (SEQ ID NO:84), KWKIYSYAGE (SEQ ID NO:85), DIYSYK (SEQ ID NO:86), DIYSYAK (SEQ ID NO:87), DIYSYAGK (SEQ ID NO:88), DKIYSYK (SEQ ID NO:89), DKIYSYAK (SEQ ID NO:90), DKIYSYAGK (SEQ ID NO:91), DWKIYSYK (SEQ ID NO:92), DWKIYSYAK (SEQ ID NO:93), DWKIYSYAGK (SEQ ID NO:94), EIYSYK (SEQ ID NO:95), EIYSYAK (SEQ ID NO:96), EIYSYAGK (SEQ ID NO:97), EKIYSYK (SEQ ID NO:98), EKIYSYAK (SEQ ID NO:99), EKIYSYAGK (SEQ ID NO:100), EWKIYSYK (SEQ ID NO:101), EWKIYSYAK (SEQ ID NO:102), EWKIYSYAGK (SEQ ID NO:103), IYSYA (SEQ ID NO:104), IYSYAG (SEQ ID NO:105), KIYSY (SEQ ID NO:106), KIYSYAG (SEQ ID NO:107), WKIYSY (SEQ ID NO:108), WKIYSYA (SEQ ID NO:109) or WKIYSYAG (SEQ ID NO:110).

Within other aspects, a modulating agent may comprise an antibody or antigen-binding fragment thereof that specifically binds to the claudin-1 CAR sequence WKIYSYAG (SEQ ID NO:34).

Within further aspects, a modulating agent as described above may comprise one or more claudin-2 CAR sequences selected from the group consisting of: TSSY (SEQ ID NO:3), TSSYV (SEQ ID NO:35), TSSYVG (SEQ ID NO:36), RTSSY (SEQ ID NO:37), RTSSYV (SEQ ID NO:38), RTSSYVG (SEQ ID NO:39), WRTSSY (SEQ ID NO:40), WRTSSYV (SEQ ID NO:41) and WRTSSYVG (SEQ ID NO:42). Such CAR sequences may be present within a cyclic peptide, such as: CTSSYC (SEQ ID NO:111), CTSSYVC (SEQ ID NO:112), CTSSYVGC (SEQ ID NO:113), CRTSSYC (SEQ ID NO:114), CRTSSYVC (SEQ ID NO:115), CRTSSYVGC (SEQ ID NO:116), CWRTSSYC (SEQ ID NO:117), CWRTSSYVC (SEQ ID NO:118), CWRTSSYVGC (SEQ ID NO:119), KTSSYD (SEQ ID NO:120), KTSSYVD (SEQ ID NO:121), KTSSYVGD (SEQ ID NO:122), KRTSSYD (SEQ ID NO:123), KRTSSYVD (SEQ ID NO:124), KRTSSYVGD (SEQ ID NO:125), KWRTSSYD (SEQ ID NO:126), KWRTSSYVD (SEQ ID NO:127), KWRTSSYVGD (SEQ ID NO:128), KTSSYE (SEQ ID NO:129), KTSSYVE (SEQ ID NO:130), KTSSYVGE (SEQ ID NO:131), KRTSSYE (SEQ ID NO:132), KRTSSYVE (SEQ ID NO:133), KRTSSYVGE (SEQ ID NO:134), KWRTSSYE (SEQ ID NO:135), KWRTSSYVE (SEQ ID NO:136), KWRTSSYVGE (SEQ ID NO:137), DTSSYK (SEQ ID NO:138), DTSSYVK (SEQ ID NO:139), DTSSYVGK (SEQ ID NO:140), DRTSSYK (SEQ ID NO:141), DRTSSYVK (SEQ ID NO:142), DRTSSYVGK (SEQ ID NO:143), DWRTSSYK (SEQ ID NO:144), DWRTSSYVK (SEQ ID NO:145), DWRTSSYVGK (SEQ ID NO:146), ETSSYK (SEQ ID NO:147), ETSSYVK (SEQ ID NO:148), ETSSYVGK (SEQ ID NO:149), ERTSSYK (SEQ ID NO:150), ERTSSYVK (SEQ ID NO:151), ERTSSYVGK (SEQ ID NO:152), EWRTSSYK (SEQ ID NO:153), EWRTSSYVK (SEQ ID NO:154), EWRTSSYVGK (SEQ ID NO:155), TSSYV (SEQ ID NO:156), TSSYVG (SEQ ID NO:157), RTSSY (SEQ ID NO:158), RTSSYV (SEQ ID NO:159), RTSSYVG (SEQ ID NO:160), WRTSSY (SEQ ID NO:161), WRTSSYV (SEQ ID NO:162) and WRTSSYVG (SEQ ID NO:163).

Within other aspects, a modulating agent may comprise an antibody or antigen-binding fragment thereof that specifically binds to the claudin-2 CAR sequence WRTSSYVG (SEQ ID NO:42).

Within further aspects, a modulating agent comprises one or more claudin-3 CAR sequences selected from the group consisting of: VSAF (SEQ ID NO:5), VSAFI (SEQ ID NO:51), VSAFIG (SEQ ID NO:52), RVSAF (SEQ ID NO:53), RVSAFI (SEQ ID NO:54), RVSAFIG (SEQ ID NO:55), WRVSAF (SEQ ID NO:56), WRVSAFI (SEQ ID NO:57) and WRVSAFIG (SEQ ID NO:58). Such CAR sequences may be present within a cyclic peptide, such as: CVSAFC (SEQ ID NO:217), CVSAFIC (SEQ ID NO:218), CVSAFIGC (SEQ ID NO:219), CRVSAFC (SEQ ID NO:220), CRVSAFIC (SEQ ID NO:221), CRVSAFIGC (SEQ ID NO:222), CWRVSAFC (SEQ ID NO:223), CWRVSAFIC (SEQ ID NO:224), CWRVSAFIGC (SEQ ID NO:225), KVSAFD (SEQ ID NO:226), KVSAFID (SEQ ID NO:227), KVSAFIGD (SEQ ID NO:228), KRVSAFD (SEQ ID NO:229), KRVSAFID (SEQ ID NO:230), KRVSAFIGD (SEQ ID NO:231), KWRVSAFD (SEQ ID NO:232), KWRVSAFID (SEQ ID NO:233), KWRVSAFIGD (SEQ ID NO:234), KVSAFE (SEQ ID NO:235), KVSAFIE (SEQ ID NO:236), KVSAFIGE (SEQ ID NO:237), KRVSAFE (SEQ ID NO:238), KRVSAFIE (SEQ ID NO:239), KRVSAFIGE (SEQ ID NO:240), KWRVSAFE (SEQ ID NO:241), KWRVSAFIE (SEQ ID NO:242), KWRVSAFIGE (SEQ ID NO:243), DVSAFK (SEQ ID NO:244), DVSAFIK (SEQ ID NO:245), DVSAFIGK (SEQ ID NO:246), DRVSAFK (SEQ ID NO:247), DRVSAFIK (SEQ ID NO:248), DRVSAFIGK (SEQ ID NO:249), DWRVSAFK (SEQ ID NO:250), DWRVSAFIK (SEQ ID NO:251), DWRVSAFIGK (SEQ ID NO:252), EVSAFK (SEQ ID NO:253), EVSAFIK (SEQ ID NO:254), EVSAFIGK (SEQ ID NO:255), ERVSAFK (SEQ ID NO:256), ERVSAFIK (SEQ ID NO:257), ERVSAFIGK (SEQ ID NO:258), EWRVSAFK (SEQ ID NO:259), EWRVSAFIK (SEQ ID NO:260), EWRVSAFIGK (SEQ ID NO:261), VSAFI (SEQ ID NO:262), VSAFIG (SEQ ID NO:263), RVSAF (SEQ ID NO:264), RVSAFI (SEQ ID NO:265), RVSAFIG (SEQ ID NO:266), WRVSAF (SEQ ID NO:267), WRVSAFI (SEQ ID NO:268) and WRVSAFIG (SEQ ID NO:269).

Within other aspects, a modulating agent may comprise an antibody or antigen-binding fragment thereof that specifically binds to the claudin-3 CAR sequence WRVSAFIG (SEQ ID NO:58).

Modulating agents may comprise, within other aspects one or more claudin-4 CAR sequences selected from the group consisting of: VTAF (SEQ ID NO:4), VTAFI (SEQ ID NO:43), VTAFIG (SEQ ID NO:44), RVTAF (SEQ ID NO:45), RVTAFI (SEQ ID NO:46), RVTAFIG (SEQ ID NO:47), WRVTAF (SEQ ID NO:48), WRVTAFI (SEQ ID NO:49) and WRVTAFIG (SEQ ID NO:50). Such CAR sequences may be present within a cyclic peptide, such as: CVTAFC (SEQ ID NO:164), CVTAFIC (SEQ ID NO:165), CVTAFIGC (SEQ ID NO:166), CRVTAFC (SEQ ID NO:167), CRVTAFIC (SEQ ID NO:168), CRVTAFIGC (SEQ ID NO:169), CWRVTAFC (SEQ ID NO:170), CWRVTAFIC (SEQ ID NO:171), CWRVTAFIGC (SEQ ID NO:172), KVTAFD (SEQ ID NO:173), KVTAFID (SEQ ID NO:174), KVTAFIGD (SEQ ID NO:175), KRVTAFD (SEQ ID NO:176), KRVTAFID (SEQ ID NO:177), KRVTAFIGD (SEQ ID NO:178), KWRVTAFD (SEQ ID NO:179), KWRVTAFID (SEQ ID NO:180), KWRVTAFIGD (SEQ ID NO:181), KVTAFE (SEQ ID NO:182), KVTAFIE (SEQ ID NO:183), KVTAFIGE (SEQ ID NO:184), KRVTAFE (SEQ ID NO:185), KRVTAFIE (SEQ ID NO:186), KRVTAFIGE (SEQ ID NO:187), KWRVTAFE (SEQ ID NO:188), KWRVTAFIE (SEQ ID NO:189), KWRVTAFIGE (SEQ ID NO:190), DVATFK (SEQ ID NO:191), DVTAFIK (SEQ ID NO:192), DVTAFIGK (SEQ ID NO:193), DRVTAFK (SEQ ID NO:194), DRVTAFIK (SEQ ID NO:195), DRVTAFIGK (SEQ ID NO:196), DWRVTAFK (SEQ ID NO:197), DWRVTAFIK (SEQ ID NO:198), DWRVTAFIGK (SEQ ID NO:199), EVTAFK (SEQ ID NO:200), EVTAFIK (SEQ ID NO:201), EVTAFIGK (SEQ ID NO:202), ERVTAFK (SEQ ID NO:203), ERVTAFIK (SEQ ID NO:204), ERVTAFIGK (SEQ ID NO:205), EWRVTAFK (SEQ ID NO:206), EWRVTAFIK (SEQ ID NO:207), EWRVTAFIGK (SEQ ID NO:208), VTAFI (SEQ ID NO:209), VTAFIG (SEQ ID NO:210), RVTAF (SEQ ID NO:211), RVTAFI (SEQ ID NO:212), RVTAFIG (SEQ ID NO:213), WRVTAF (SEQ ID NO:214), WRVTAFI (SEQ ID NO:215) and WRVTAFIG (SEQ ID NO:216).

Within other aspects, a modulating agent may comprise an antibody or antigen-binding fragment thereof that specifically binds to the claudin-4 CAR sequence WRVTAFIG (SEQ ID NO:50).

Modulating agents may comprise, within other aspects one or more claudin-5 CAR sequences selected from the group consisting of: VTAF (SEQ ID NO:4), VTAFL (SEQ ID NO:270), VTAFLD (SEQ ID NO:271), QVTAF (SEQ ID NO:272), QVTAFL (SEQ ID NO:273), QVTAFLD (SEQ ID NO:274), WQVTAF (SEQ ID NO:275), WQVTAFL (SEQ ID NO:276) and WQVTAFLD (SEQ ID NO:277). Such CAR sequences may be present within a cyclic peptide, such as: CVTAFC (SEQ ID NO:164), CVTAFLC (SEQ ID NO:278), CVTAFLDC (SEQ ID NO:279), CQVTAFC (SEQ ID NO:280), CQVTAFLC (SEQ ID NO:281), CQVTAFLDC (SEQ ID NO:282), CWQVTAFC (SEQ ID NO:283), CWQVTAFLC (SEQ ID NO:284), CWQVTAFLDC (SEQ ID NO:285), KVTAFD (SEQ ID NO:286), KVTAFLD (SEQ ID NO:287), KVTAFLDD (SEQ ID NO:288), KQVTAFD (SEQ ID NO:289), KQVTAFLD (SEQ ID NO:290), KQVTAFLDD (SEQ ID NO:291), KWQVTAFD (SEQ ID NO:292), KWQVTAFLD (SEQ ID NO:293), KWQVTAFLDD (SEQ ID NO:294), KVTAFE (SEQ ID NO:182), KVTAFLE (SEQ ID NO:295), KVTAFLDE (SEQ ID NO:296), KQVTAFE (SEQ ID NO:297), KQVTAFLE (SEQ ID NO:298), KQVTAFLDE (SEQ ID NO:299), KWQVTAFE (SEQ ID NO:300), KWQVTAFLE (SEQ ID NO:301), KWQVTAFLDE (SEQ ID NO:302), DVATFK (SEQ ID NO:303), DVTAFLK (SEQ ID NO:304), DVTAFLDK (SEQ ID NO:305), DQVTAFK (SEQ ID NO:306), DQVTAFLK (SEQ ID NO:307), DQVTAFLDK (SEQ ID NO:308), DWQVTAFK (SEQ ID NO:309), DWQVTAFLK (SEQ ID NO:310), DWQVTAFLDK (SEQ ID NO:311), EVTAFK (SEQ ID NO:200), EVTAFLK (SEQ ID NO:312), EVTAFLDK (SEQ ID NO:313), EQVTAFK (SEQ ID NO:314), EQVTAFLK (SEQ ID NO:315), EQVTAFLDK (SEQ ID NO:316), EWQVTAFK (SEQ ID NO:317), EWQVTAFLK (SEQ ID NO:318), EWQVTAFLDK (SEQ ID NO:319), VTAFL (SEQ ID NO:320), VTAFLD (SEQ ID NO:321), QVTAF (SEQ ID NO:322), QVTAFL (SEQ ID NO:323), QVTAFLD (SEQ ID NO:324), WQVTAF (SEQ ID NO:325), WQVTAFL (SEQ ID NO:326) and WQVTAFLD (SEQ ID NO:327).

Within other aspects, a modulating agent may comprise an antibody or antigen-binding fragment thereof that specifically binds to the claudin-5 CAR sequence WQVTAFLD (SEQ ID NO:277).

Modulating agents may comprise, within other aspects one or more claudin-6 CAR sequences selected from the group consisting of: VTAF (SEQ ID NO:4), VTAFI (SEQ ID NO:328), VTAFIG (SEQ ID NO:329), KVTAF (SEQ ID NO:330), KVTAFI (SEQ ID NO:331), KVTAFIG (SEQ ID NO:332), WKVTAF (SEQ ID NO:333), WKVTAFI (SEQ ID NO:334) and WKVTAFIG (SEQ ID NO:335). Such CAR sequences may be present within a cyclic peptide, such as: CVTAFC (SEQ ID NO:164), CVTAFIC (SEQ ID NO:336), CVTAFIGC (SEQ ID NO:337), CKVTAFC (SEQ ID NO:338), CKVTAFIC (SEQ ID NO:339), CKVTAFIGC (SEQ ID NO:340), CWKVTAFC (SEQ ID NO:341), CWKVTAFIC (SEQ ID NO:342), CWKVTAFIGC (SEQ ID NO:343), KVTAFD (SEQ ID NO:344), KVTAFID (SEQ ID NO:345), KVTAFIGD (SEQ ID NO:346), KKVTAFD (SEQ ID NO:347), KKVTAFID (SEQ ID NO:348), KKVTAFIGD (SEQ ID NO:349), KWKVTAFD (SEQ ID NO:350), KWKVTAFID (SEQ ID NO:351), KWKVTAFIGD (SEQ ID NO:352), KVTAFE (SEQ ID NQ:182), KVTAFIE (SEQ ID NO:353), KVTAFIGE (SEQ ID NO:354), KKVTAFE (SEQ ID NO:355), KKVTAFIE (SEQ ID NO:356), KKVTAFIGE (SEQ ID NO:357), KWKVTAFE (SEQ ID NO:358), KWKVTAFIE (SEQ ID NO:359), KWKVTAFIGE (SEQ ID NO:360), DVATFK (SEQ ID NO:361), DVTAFIK (SEQ ID NO:362), DVTAFIGK (SEQ ID NO:363), DKVTAFK (SEQ ID NO:364), DKVTAFIK (SEQ ID NO:365), DKVTAFIGK (SEQ ID NO:366), DWKVTAFK (SEQ ID NO:367), DWKVTAFIK (SEQ ID NO:368), DWKVTAFIGK (SEQ ID NO:369), EVTAFK (SEQ ID NO:200), EVTAFIK (SEQ ID NO:370), EVTAFIGK (SEQ ID NO:371), EKVTAFK (SEQ ID NO:372), EKVTAFIK (SEQ ID NO:373), EKVTAFIGK (SEQ ID NO:374), EWKVTAFK (SEQ ID NO:375), EWKVTAFIK (SEQ ID NO:376), EWKVTAFIGK (SEQ ID NO:377), VTAFI (SEQ ID NO:378), VTAFIG (SEQ ID NO:379), KVTAF (SEQ ID NO:380), KVTAFI (SEQ ID NO:381), KVTAFIG (SEQ ID NO:382), WKVTAF (SEQ ID NO:383), WKVTAFI (SEQ ID NO:384) and WKVTAFIG (SEQ ID NO:385).

Within other aspects, a modulating agent may comprise an antibody or antigen-binding fragment thereof that specifically binds to the claudin-6 CAR sequence WKVTAFIG (SEQ ID NO:335).

Within further aspects, a modulating agent as described above may comprise one or more claudin-7 CAR sequences selected from the group consisting of: MSSY (SEQ ID NO:386), MSSYA (SEQ ID NO:387), MSSYAG (SEQ ID NO:388), QMSSY (SEQ ID NO:389), QMSSYA (SEQ ID NO:390), QMSSYAG (SEQ ID NO:391), WQMSSY (SEQ ID NO:392), WQMSSYA (SEQ ID NO:393) and WQMSSYAG (SEQ ID NO:394). Such CAR sequences may be present within a cyclic peptide, such as: CMSSYC (SEQ ID NO:395), CMSSYAC (SEQ ID NO:396), CMSSYAGC (SEQ ID NO:397), CQMSSYC (SEQ ID NO:398), CQMSSYAC (SEQ ID NO:399), CQMSSYAGC (SEQ ID NO:400), CWQMSSYC (SEQ ID NO:401), CWQMSSYAC (SEQ ID NO:402), CWQMSSYAGC (SEQ ID NO:403), KMSSYD (SEQ ID NO:404), KMSSYAD (SEQ ID NO:405), KMSSYAGD (SEQ ID NO:406), KQMSSYD (SEQ ID NO:407), KQMSSYAD (SEQ ID NO:408), KQMSSYAGD (SEQ ID NO:409), KWQMSSYD (SEQ ID NO:410), KWQMSSYAD (SEQ ID NO:411), KWQMSSYAGD (SEQ ID NO:412), KMSSYE (SEQ ID NO:413), KMSSYAE (SEQ ID NO:414), KMSSYAGE (SEQ ID NO:415), KQMSSYE (SEQ ID NO:416), KQMSSYAE (SEQ ID NO:417), KQMSSYAGE (SEQ ID NO:418), KWQMSSYE (SEQ ID NO:419), KWQMSSYAE (SEQ ID NO:420), KWQMSSYAGE (SEQ ID NO:421), DMSSYK (SEQ ID NO:422), DMSSYAK (SEQ ID NO:423), DMSSYAGK (SEQ ID NO:424), DQMSSYK (SEQ ID NO:425), DQMSSYAK (SEQ ID NO:426), DQMSSYAGK (SEQ ID NO:427), DWQMSSYK (SEQ ID NO:428), DWQMSSYAK (SEQ ID NO:429), DWQSSYAGK (SEQ ID NO:430), EMSSYK (SEQ ID NO:431), EMSSYAK (SEQ ID NO:432), EMSSYAGK (SEQ ID NO:433), EQMSSYK (SEQ ID NO:434), EQMSSYAK (SEQ ID NO:435), EQMSSYAGK (SEQ ID NO:436), EWQMSSYK (SEQ ID NO:437), EWQMSSYAK (SEQ ID NO:438), EWQMSSYAGK (SEQ ID NO:439), MSSYA (SEQ ID NO:440), MSSYAG (SEQ ID NO:441), QMSSY (SEQ ID NO:442), QMSSYA (SEQ ID NO:443), QMSSYAG (SEQ ID NO:444), WQMSSY (SEQ ID NO:445), WQMSSYA (SEQ ID NO:446) and WQMSSYAG (SEQ ID NO:447).

Within other aspects, a modulating agent may comprise an antibody or antigen-binding fragment thereof that specifically binds to the claudin-7 CAR sequence WQMSSYAG (SEQ ID NO:394).

Within further aspects, a modulating agent comprises one or more claudin-8 CAR sequences selected from the group consisting of: VSAF (SEQ ID NO:5), VSAFI (SEQ ID NO:51), VSAFIE (SEQ ID NO:448), RVSAF (SEQ ID NO:53), RVSAFI (SEQ ID NO:54), RVSAFIE (SEQ ID NO:449), WRVSAF (SEQ ID NO:56), WRVSAFI (SEQ ID NO:57) and WRVSAFIE (SEQ ID NO:450). Such CAR sequences may be present within a cyclic peptide, such as: CVSAFC (SEQ ID NO:217), CVSAFIC (SEQ ID NO:218), CVSAFIEC (SEQ ID NO:451), CRVSAFC (SEQ ID NO:220), CRVSAFIC (SEQ ID NO:221), CRVSAFIEC (SEQ ID NO:452), CWRVSAFC (SEQ ID NO:223), CWRVSAFIC (SEQ ID NO:224), CWRVSAFIEC (SEQ ID NO:453), KVSAFD (SEQ ID NO:226), KVSAFID (SEQ ID NO:227), KVSAFIED (SEQ ID NO:454), KRVSAFD (SEQ ID NO:229), KRVSAFID (SEQ ID NO:230), KRVSAFIED (SEQ ID NO:455), KWRVSAFD (SEQ ID NO:232), KWRVSAFID (SEQ ID NO:233), KWRVSAFIED (SEQ ID NO:456), KVSAFE (SEQ ID NO:235), KVSAFIE (SEQ ID NO:236), KVSAFIEE (SEQ ID NO:457), KRVSAFE (SEQ ID NO:238), KRVSAFIE (SEQ ID NO:239), KRVSAFIEE (SEQ ID NO:458), KWRVSAFE (SEQ ID NO:241), KWRVSAFIE (SEQ ID NO:242), KWRVSAFIEE (SEQ ID NO:459), DVSAFK (SEQ ID NO:244), DVSAFIK (SEQ ID NO:245), DVSAFIEK (SEQ ID NO:460), DRVSAFK (SEQ ID NO:247), DRVSAFIK (SEQ ID NO:248), DRVSAFIEK (SEQ ID NO:461), DWRVSAFK (SEQ ID NO:250), DWRVSAFIK (SEQ ID NO:251), DWRVSAFIEK (SEQ ID NO:462), EVSAFK (SEQ ID NO:253), EVSAFIK (SEQ ID NO:254), EVSAFIEK (SEQ ID NO:463), ERVSAFK (SEQ ID NO:256), ERVSAFIK (SEQ ID NO:257), ERVSAFIEK (SEQ ID NO:464), EWRVSAFK (SEQ ID NO:259), EWRVSAFIK (SEQ ID NO:260), EWRVSAFIEK (SEQ ID NO:465), VSAFI (SEQ ID NO:262), VSAFIE (SEQ ID NO:466), RVSAF (SEQ ID NO:264), RVSAFI (SEQ ID NO:265), RVSAFIE (SEQ ID NO:467), WRVSAF (SEQ ID NO:267), WRVSAFI (SEQ ID NO:268) and WRVSAFIE (SEQ ID NO:468).

Within other aspects, a modulating agent may comprise an antibody or antigen-binding fragment thereof that specifically binds to the claudin-8 CAR sequence WRVSAFIE (SEQ ID NO:450).

The present invention further provides pharmaceutical compositions comprising a cell adhesion modulating agent as described above, in combination with a pharmaceutically acceptable carrier. Such compositions may further comprise a drug. In addition, or alternatively, such compositions may further comprise one or more of: (a) a peptide comprising a cell adhesion recognition sequence that is bound by an adhesion molecule other than a claudin; and/or (b) an antibody or antigen-binding fragment thereof that specifically binds to a cell adhesion recognition sequence bound by an adhesion molecule other than a claudin.

Within further aspects, methods are provided for modulating cell adhesion, comprising contacting a claudin-expressing cell with a cell adhesion modulating agent as described above.

Within one such aspect, the present invention provides methods for increasing vasopermeability in a mammal, comprising administering to a mammal a cell adhesion modulating agent as provided above, wherein the modulating agent inhibits claudin-mediated cell adhesion.

Within another aspect, methods are provided for reducing unwanted cellular adhesion in a mammal, comprising administering to a mammal a cell adhesion modulating agent as provided above, wherein the modulating agent inhibits claudin-mediated cell adhesion.

In yet another aspect, the present invention provides methods for enhancing the delivery of a drug through the skin of a mammal, comprising contacting epithelial cells of a mammal with a cell adhesion modulating agent as provided above and a drug, wherein the modulating agent inhibits claudin-mediated cell adhesion, and wherein the step of contacting is performed under conditions and for a time sufficient to allow passage of the drug across the epithelial cells.

The present invention further provides methods for enhancing the delivery of a drug to a tumor in a mammal, comprising administering to a mammal a cell adhesion modulating agent as provided above and a drug, wherein the modulating agent inhibits claudin-mediated cell adhesion.

Within further aspects, the present invention provides methods for treating cancer in a mammal, comprising administering to a mammal a cell adhesion modulating agent as provided above, wherein the modulating agent inhibits claudin-mediated cell adhesion.

The present invention further provides methods for inhibiting angiogenesis in a mammal, comprising administering to a mammal a cell adhesion modulating agent as provided above, wherein the modulating agent inhibits claudin-mediated cell adhesion.

Within further aspects, the present invention provides methods for enhancing drug delivery to the central nervous system of a mammal, comprising administering to a mammal a cell adhesion modulating agent as provided above, wherein the modulating agent inhibits claudin-mediated cell adhesion.

The present invention further provides methods for enhancing wound healing in a mammal, comprising contacting a wound in a mammal with a cell adhesion modulating agent as provided above, wherein the modulating agent enhances claudin-mediated cell adhesion.

Within a related aspect, the present invention provides methods for enhancing adhesion of foreign tissue implanted within a mammal, comprising contacting a site of implantation of foreign tissue in a mammal with a cell adhesion modulating agent as provided above, wherein the modulating agent enhances claudin-mediated cell adhesion.

The present invention further provides methods for inducing apoptosis in a claudin-expressing cell, comprising contacting a claudin-expressing cell with a cell adhesion modulating agent as provided above, wherein the modulating agent inhibits claudin-mediated cell adhesion.

The present invention further provides methods for identifying an agent capable of modulating claudin-mediated cell adhesion. One such method comprises the steps of (a) culturing cells that express a claudin in the presence and absence of a candidate agent, under conditions and for a time sufficient to allow cell adhesion; and (b) visually evaluating the extent of cell adhesion among the cells.

Within another embodiment, such methods may comprise the steps of: (a) culturing normal rat kidney cells in the presence and absence of a candidate agent, under conditions and for a time sufficient to allow cell adhesion; and (b) comparing the level of cell surface claudin and E-cadherin for cells cultured in the presence of candidate agent to the level for cells cultured in the absence of candidate agent.

Within a further embodiment, such methods may comprise the steps of: (a) culturing human aortic endothelial cells in the presence and absence of a candidate agent, under conditions and for a time sufficient to allow cell adhesion; and (b) comparing the level of cell surface claudin and N-cadherin for cells cultured in the presence of candidate agent to the level for cells cultured in the absence of candidate agent.

Within yet another embodiment, such methods comprise the steps of: (a) contacting an antibody that binds to a modulating agent comprising a claudin CAR sequence with a test compound; and (b) detecting the level of antibody that binds to the test compound.

The present invention further provides methods for detecting the presence of claudin-expressing cells in a sample, comprising: (a) contacting a sample with an antibody that binds to a claudin comprising a claudin CAR sequence under conditions and for a time sufficient to allow formation of an antibody-claudin complex; and (b) detecting the level of antibody-claudin complex, and therefrom detecting the presence of claudin-expressing cells in the sample.

Within further aspects, the present invention provides kits for detecting the presence of claudin-expressing cells in a sample, comprising: (a) an antibody that binds to a modulating agent comprising a claudin CAR sequence; and (b) a detection reagent.

The present invention further provides, within other aspects, kits for enhancing transdermal drug delivery, comprising: (a) a skin patch; and (b) a cell adhesion modulating agent, wherein the modulating agent comprises a claudin CAR sequence, and wherein the modulating agent inhibits claudin-mediated cell adhesion.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 1 provides the amino acid sequences of extracellular domain 1 of representative mammalian claudins, as indicated. The extracellular domains were predicted by hydrophobicity analysis using the Kyte-Doolittle algorithm (Kyte and Doolittle, *J. Molecular Biology* 157:105–132, 1982), from mouse claudin-1 (SEQ ID NO:6), mouse claudin-2 (SEQ ID NO:7), mouse claudin-3 (SEQ ID NO:469); human claudin-3 (SEQ ID NO:11), rat claudin-3 (SEQ ID NO:12), mouse claudin-4 (SEQ ID NO:9), human claudin-4 (SEQ ID NO:8), African green Monkey claudin-4 (SEQ ID NO:10), mouse claudin-5 (SEQ ID NO:470), human claudin-5 (SEQ ID NO:471), mouse claudin-6 (SEQ ID NO:472), mouse claudin-7 (SEQ ID NO:473) and mouse claudin-8 (SEQ ID NO:474). Sequences were compared using a Clustal W protein sequence alignment. Amino acids are represented by their IUPAC amino acid codes, where X is any amino acid and - represents a gap. The consensus sequence (SEQ ID NO:13) is shown in italics, and amino acids capitalized within the consensus represent identity. The claudin family cell adhesion recognition region is shown in bold.

DETAILED DESCRIPTION OF THE INVENTION

Figure 2A:
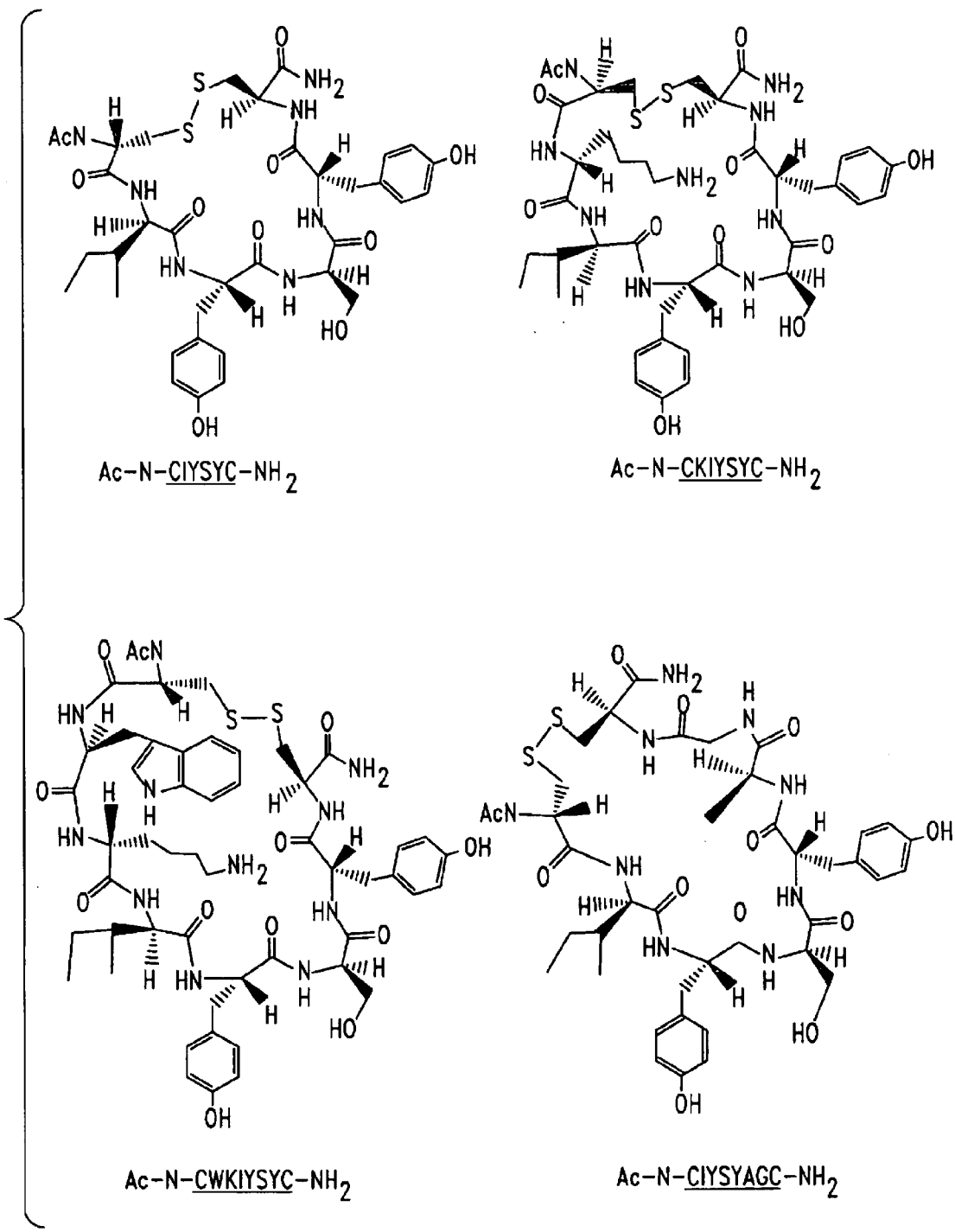
FIGS. 2A and 2B provide the structures of representative cyclic peptide modulating agents (SEQ ID NOS: 59–62, 65, 111, 164, 217).

As noted above, the present invention provides cell adhesion modulating agents comprising peptides that are capable of modulating claudin-mediated processes, such as cell adhesion. The present invention is based on the identification of previously unknown cell adhesion recognition (CAR) sequences present in claudins. A modulating agent may generally comprise one or more claudin CAR sequences (or analogues or mimetics thereof), with or without one or more additional CAR sequences, as described below. Peptide CAR sequences may be present within a linear or cyclic peptide. Alternatively, or in addition, a modulating agent may comprise a polynucleotide encoding a peptide comprising one or more claudin CAR sequences and/or a modulating agent may comprise a substance (such as an antibody or antigen-binding fragment thereof) that specifically binds to a claudin CAR sequence.

In general, to modulate claudin-mediated cell adhesion, a claudin-expressing cell is contacted with a cell adhesion modulating agent (also referred to herein as a "modulating agent") either in vivo or in vitro. Claudin-expressing cells may be readily identified using any of a variety of techniques well known in the art (such as, for example, hybridization, PCR or immunohistochemical techniques), and include endothelial and epithelial cells, as well as cancer cells, such as carcinoma cells. Within certain aspects, the methods provided herein inhibit a claudin-mediated function. Such methods include, for example, methods for treating diseases or other conditions characterized by undesirable cell adhesion or for facilitating drug delivery to a specific tissue or tumor. Certain methods may inhibit cell adhesion (e.g., cancer cell adhesion), as well as cancer invasion and metastasis. Alternatively, a modulating agent may, such as when linked to a matrix or to another modulating agent via a linker, be used to enhance a claudin-mediated function, such as cell adhesion. Such conjugates may be used, for example, to facilitate wound healing or the adhesion of implants.

Cell Adhesion Modulating Agents

The term "cell adhesion modulating agent," as used herein, refers to a molecule comprising at least one of the following components:

(a) a linear or cyclic peptide sequence that is at least 50% identical to a claudin CAR sequence (i.e., a claudin CAR sequence or an analogue thereof that retains at least 50% identity);

(b) a mimetic (e.g., peptidomimetic or small molecule mimic) of a claudin CAR sequence;

(c) a substance such as an antibody or antigen-binding fragment thereof that specifically binds a claudin CAR sequence; and/or (d) a polynucleotide encoding a polypeptide that comprises a claudin CAR sequence or analogue thereof.

A modulating agent may consist entirely of one or more of the above elements, or may additionally comprise further peptide and/or non-peptide regions. Additional peptide regions may be derived from a claudin (preferably an extracellular domain that comprises a CAR sequence) and/or may be heterologous. Within certain preferred embodiments, a modulating agent contains no more than 85 consecutive amino acid residues, and preferably no more than 50 consecutive amino acid residues, present within a claudin.

A modulating agent is further capable of modulating a function mediated by a claudin. Such activity may generally be assessed using, for example, representative assays provided herein. Certain modulating agents inhibit an interaction between claudin molecules and/or between a claudin and a different adhesion molecule. For functions (e.g., cell adhesion) that are inhibited by a full length, soluble claudin, such a modulating agent may inhibit the function with an activity that is not substantially diminished relative to the full length claudin (i.e., the modulating agent inhibits the function at least as well as soluble claudin, when contacted with cells that express the claudin). For example, a modulating agent may be as effective as soluble claudin in preventing and/or disrupting adhesion of claudin-expressing cells. Alternatively, to enhance adhesion of claudin-expressing cells, a modulating agent may comprise an antibody or antigen-binding fragment thereof and/or multiple peptides or mimetics linked to a support material. Such modulating agents may function as a biological glue to bind claudin-expressing cells, and should result in a detectable enhancement of cell adhesion (preferably an enhancement that is at least as great as that observed for immobilized claudin or antibody directed against the claudin).

The term "claudin," as used herein, refers to an integral membrane protein with a molecular weight of approximately 22 kD, which contains two extracellular domains and four transmembrane domains (as determined by hydrophobicity analysis), and which displays at least 30% sequence identity to a member of the claudin family specifically recited herein. Claudins include claudin-1 and claudin-2 (Furuse et al., *J. Cell Biology* 141:1539–1550, 1998), which show 38% sequence identity and are present in tight junctions. Other proteins that are considered members of the claudin family are claudin-3 (also known as RVP-1; Morita et al., *Proc. Natl. Acad. Sci. USA* 96:511–516, 1999; Briehl and Miesfeld, *Molecular Endocrinology* 5:1381–1388, 1991; Katahira et al., *J. Biological Chemistry* 272:26652–26656, 1997), claudin-4 (also known as the *Clostridium perfringens* enterotoxin receptor (CPE-R); see Morita et al., *Proc. Natl. Acad. Sci. USA* 96:511–516, 1999; Katahira et al., *J. Cell Biology* 136:1239–1247, 1997; Katahira et al., *J. Biological Chemistry* 272:26652–26656, 1997) and TMVCF (transmembrane protein deleted in Velo-cardio-facial syndrome, also known as claudin-5; Morita et al., *Proc. Natl. Acad. Sci. USA* 96:511–516, 1999; Sirotkin et al. *Genomics* 42:245–51, 1997), as well as claudins-6, -7, -8 (Morita et al., *Proc. Natl. Acad Sci. USA* 96:511–516, 1999), all of which have sequences that are 40–60% identical to claudin-1. The sequence of the first extracellular domain of each of these proteins is shown in FIG. 1. All of these proteins, as well as homologues from other species, are considered claudins within the context of the present invention, and all contain a claudin CAR sequence, as described herein.

A claudin CAR sequence, as used herein, is an amino acid sequence that is present in a naturally occurring claudin and that is capable of detectably modulating a claudin-mediated function, such as cell adhesion, as described herein. In other words, contacting a claudin-expressing cell with a peptide comprising a CAR sequence results in a detectable change in a claudin-mediated function using at least one of the representative assays provided herein. CAR sequences may be of any length, but generally comprise at least three amino acid residues, preferably 4–16 amino acid residues, and more preferably 5–8 amino acid residues. A peptide modulating agent may comprise any number of amino acid residues, but preferred agents comprise 3–50 residues, preferably 4–16 residues. Within certain embodiments, a peptide modulating agent preferably comprises an N-acetyl group (i.e., the amino group present on the amino terminal residue of the peptide is acetylated). It has been found, within the context of the present invention, that the presence of such an acetyl group may enhance peptide modulating activity for certain applications.

Claudin CAR sequences are generally physically located within the claudin molecule in or near the binding site of an adhesion molecule (i.e., within 10 amino acids, and preferably within 5 amino acids). The location of a binding site may generally be determined using well known techniques, such as evaluating the ability of a portion of the claudin to bind to the same claudin or to another adhesion molecule. Any standard binding assay may be employed for such an evaluation. Recognition of a CAR sequence by the claudin or other adhesion molecule results in a measurable effect on an adhesion molecule function, such as cell adhesion. Peptides comprising a CAR sequence generally inhibit such a function unless linked, as described herein, to form an enhancer of adhesion molecule function.

It has been found, within the context of the present invention, that certain claudin CAR sequences share the consensus sequence:

Trp-Lys/Arg/Gln-Aaa-Baa-Ser/Ala-Tyr/Phe-Caa-Gly/Asp/Glu     (SEQ ID NO:1).

Within the consensus sequence, Aaa, Baa and Caa indicate independently selected amino acid residues; Lys/Arg/Gln is an amino acid that is lysine, arginine or glutamine; Ser/Ala is an amino acid that is serine or alanine; Tyr/Phe is an amino acid that is tyrosine or phenylalanine; and Gly/Asp/Glu is an amino acid that is glycine, aspartic acid or glutamic acid. Representative claudin CAR sequences are provided within Table I. CAR sequences specifically provided herein further include portions of such representative CAR sequences, as well as longer polypeptides that comprise at least a portion of such sequences. Additional claudin CAR sequences may be identified based on sequence homology to the claudin CAR sequences provided herein, and based on the ability of a peptide comprising such a sequence to modulate a claudin-mediated function within a representative assay described herein. Within certain embodiments, a modulating agent comprises at least three consecutive residues, preferably at least five consecutive residues and more preferably at least seven consecutive residues, of a claudin CAR sequence that satisfies the above consensus sequence.

TABLE I

Representative Claudin CAR Sequences

| Claudin | CAR Sequence |
| --- | --- |
| Mouse claudin-1 | WKIYSYAG (SEQ ID NO:34) |
| Mouse claudin-2 | WRTSSYVG (SEQ ID NO:42) |
| Mouse claudin-3 | WRVSAFIG (SEQ ID NO:58) |
| Human claudin-3 | WRVSAFIG (SEQ ID NO:58) |
| Rat claudin-3 | WRVSAFIG (SEQ ID NO:58) |
| Human claudin-4 | WRVTAFIG (SEQ ID NO:50) |
| Mouse claudin-4 | WRVTAFIG (SEQ ID NO:50) |
| C. aethiops claudin-4 | WRVTAFIG (SEQ ID NO:50) |
| Mouse claudin-5 | WQVTAFLD (SEQ ID NO:277) |
| Human claudin-5 | WQVTAFLD (SEQ ID NO:277) |
| Mouse claudin-6 | WKVTAFIG (SEQ ID NO:335) |
| Mouse claudin-7 | WQMSSYAG (SEQ ID NO:394) |
| Mouse claudin 8 | WRVSAFIE (SEQ ID NO:450) |
| CONSENSUS | WkxxafxG (SEQ ID NO:1) q  sy d r   e |

Certain preferred claudin CAR sequences comprise 3–8 amino acid residues of a sequence provided in Table I. For example, a CAR sequence may comprise 3, 4 or 5 residues of an eight-amino acid sequence in Table I. Certain preferred CAR sequences comprise at least the sequence IYSY (SEQ ID NO:2), TSSY (SEQ ID NO:3), VTAF (SEQ ID NO:4), MSSY (SEQ ID NO:386) or VSAF (SEQ ID NO:5). A CAR sequence may further comprise one or more amino acids that flank the sequences provided in Table I, such that the CAR sequence is nine or more amino acids in length.

Representative claudin-1 CAR sequences include IYSY (SEQ ID NO:2), IYSYA (SEQ ID NO:27), KIYSY (SEQ ID NO:29), IYSYAG (SEQ ID NO:28), KIYSYA (SEQ ID NO:30), WKIYSY (SEQ ID NO:32), KIYSYAG (SEQ ID NO:31), WKIYSYA (SEQ ID NO:33) and WKIYSYAG (SEQ ID NO:34). Linear peptides having such sequences may be modified at the N- and/or C-termini, as in the peptide N-Ac-WKIYSYAG-NH$_2$ (SEQ ID NO:34).

Representative claudin-2 CAR sequences include TSSY (SEQ ID NO:3), TSSYV (SEQ ID NO:35), RTSSY (SEQ ID NO:37), TSSYVG (SEQ ID NO:36), RTSSYV (SEQ ID NO:38), WRTSSY (SEQ ID NO:40), RTSSYVG (SEQ ID NO:39), WRTSSYV (SEQ ID NO:41), WRTSSYVG (SEQ ID NO:42). Linear peptides having such sequences may be modified at the N- and/or C-termini, as in the peptide N-Ac-WRTSSYVG-NH$_2$ (SEQ ID NO:42).

Representative claudin-3 CAR sequences include VSAF (SEQ ID NO:4), VSAFI (SEQ ID NO:51), VSAFIG (SEQ ID NO:52), RVSAF (SEQ ID NO:53), RVSAFI (SEQ ID NO:54), RVSAFIG (SEQ ID NO:55), WRVSAF (SEQ ID NO:56), WRVSAFI (SEQ ID NO:57) and WRVSAFIG (SEQ ID NO:58). Linear peptides having such sequences may be modified at the N- and/or C-termini, as in the peptide N-Ac-WRVSAFIG-NH$_2$ (SEQ ID NO:58).

Representative claudin-4 CAR sequences include VTAF (SEQ ID NO:4), VTAFI (SEQ ID NO:43), VTAFIG (SEQ ID NO:44), RVTAF (SEQ ID NO:45), RVTAFI (SEQ ID NO:46), RVTAFIG (SEQ ID NO:47), WRVTAF (SEQ ID NO:48), WRVTAFI (SEQ ID NO:49) and WRVTAFIG (SEQ ID NO:50). Linear peptides having such sequences may be modified at the N- and/or C-termini, as in the peptide N-Ac-WRVTAFIG-NH$_2$ (SEQ ID NO:50).

Representative claudin-5 CAR sequences include VTAF (SEQ ID NO:4), VTAFL (SEQ ID NO:270), VTAFLD (SEQ ID NO:271), QVTAF (SEQ ID NO:272), QVTAFL (SEQ ID NO:273), QVTAFLD (SEQ ID NO:274), WQVTAF (SEQ ID NO:275), WQVTAFL (SEQ ID NO:276) and WQVTAFLD (SEQ ID NO:277). Linear peptides having such sequences may be modified at the N- and/or C-termini, as in the peptide N-Ac-WQVTAFLD-NH$_2$ (SEQ ID NO:277).

Representative claudin-6 CAR sequences include VTAF (SEQ ID NO:4), VTAFI (SEQ ID NO:328), VTAFIG (SEQ ID NO:329), KVTAF (SEQ ID NO:330), KVTAFI (SEQ ID NO:331), KVTAFIG (SEQ ID NO:332), WKVTAF (SEQ ID NO:333), WKVTAFI (SEQ ID NO:334) and WKVTAFIG (SEQ ID NO:335). Linear peptides having such sequences may be modified at the N- and/or C-termini, as in the peptide N-Ac-WKVTAFIG-NH$_2$ (SEQ ID NO:335).

Representative claudin-7 CAR sequences include MSSY (SEQ ID NO:386), MSSYA (SEQ ID NO:387), MSSYAG (SEQ ID NO:388), QMSSY (SEQ ID NO:389), QMSSYA (SEQ ID NO:390), QMSSYAG (SEQ ID NO:391), WQMSSY (SEQ ID NO:392), WQMSSYA (SEQ ID NO:393) and WQMSSYAG (SEQ ID NO:394). Linear peptides having such sequences may be modified at the N- and/or C-termini, as in the peptide N-Ac-WQMSSYAG-NH$_2$ (SEQ ID NO:394).

Representative claudin-8 CAR sequences include VSAF (SEQ ID NO:5), VSAFI (SEQ ID NO:51), VSAFIE (SEQ ID NO:448), RVSAF (SEQ ID NO:53), RVSAFI (SEQ ID NO:54), RVSAFIE (SEQ ID NO:449), WRVSAF (SEQ ID NO:56), WRVSAFI (SEQ ID NO:57) and WRVSAFIE (SEQ ID NO:450). Linear peptides having such sequences may be modified at the N- and/or C-termini, as in the peptide N-Ac-WRVSAFIE-NH$_2$ (SEQ ID NO:450).

Those of ordinary skill in the art will recognize that similar peptide sequences may be designed to modulate a function mediated by other claudins, following identification of a CAR sequence as described herein.

Certain of the peptide sequences provided above may modulate a function mediated by multiple claudins. In general, peptides comprising a greater number of consecutive residues derived from a particular claudin have a greater specificity for that claudin. In addition, further flanking sequences may be included to enhance specificity. Such flanking sequences may be identified based on the sequences provided in FIG. 1, or based on published sequences. To achieve specificity (i.e., modulation of a particular claudin function that is enhanced relative to the modulation of a function mediated by a different claudin), the addition of 2 to 5 flanking residues (preferably at least one residue on either side of the CAR sequence) is generally sufficient.

As noted above, certain preferred modulating agents comprise a peptide (containing a claudin CAR sequence or an analogue thereof) in which at least one terminal amino acid residue is modified (e.g., the N-terminal amino group is modified by, for example, acetylation or alkoxybenzylation and/or an amide or ester is formed at the C-terminus). It has been found, within the context of the present invention, that the addition of at least one such group to a linear or cyclic peptide modulating agent may improve the ability of the agent to modulate a claudin-mediated function. Certain preferred modulating agents contain modifications at the N- and C-terminal residues, such as N-Ac-WKIYSYAG-NH$_2$ (SEQ ID NO:34) or N-Ac-WKIYSYAGN-NH$_2$ (SEQ ID NO:476), which modulates claudin-1 mediated functions. Other CAR sequences provided herein are also preferably modified by the addition of one or more terminal groups.

The present invention further contemplates claudin CAR sequences from other organisms. Such CAR sequences may be identified based upon sequence similarity to the sequences provided herein, and the ability to modulate a claudin-mediated function such as may be confirmed as described herein.

As noted above, modulating agents as described herein may comprise an analogue or mimetic of a claudin CAR sequence. An analogue generally retains at least 50% identity to a native claudin CAR sequence, and modulates a claudin-mediated function as described herein. Such analogues preferably contain at least three residues of, and more preferably at least five residues of, a claudin CAR sequence. An analogue may contain any of a variety of amino acid substitutions, additions, deletions and/or modifications (e.g., side chain modifications). Preferred amino acid substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. The critical determining feature of a claudin CAR sequence analogue is the ability to modulate a claudin-mediated function, which may be evaluated using the representative assays provided herein.

A mimetic is a non-peptidyl compound that is conformationally similar to a claudin CAR sequence, such that it modulates a claudin-mediated function as described below. Such mimetics may be designed based on techniques that evaluate the three dimensional structure of the peptide. For example, Nuclear Magnetic Resonance spectroscopy (NMR) and computational techniques may be used to determine the conformation of a claudin CAR sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate the lowest energy conformation for the claudin CAR sequence. This information can then be used to design mimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Mimetics may be synthesized where one or more of the amide linkages has been replaced by isosteres, substituents or groups which have the same size or volume such as —CH$_2$NH—, —CSNH—, —CH$_2$S—, —CH═CH—, —CH$_2$CH$_2$—, —CONMe— and others. These backbone amide linkages can also be part of a ring structure (e.g., lactam). Mimetics may be designed where one or more of the side chain functionalities of the claudin CAR sequence are replaced by groups that do not necessarily have the same size or volume, but have similar chemical and/or physical properties which produce similar biological responses. Other mimetics may be small molecule mimics, which may be readily identified from small molecule libraries, based on the three-dimensional structure of the CAR sequence. It should be understood that, within embodiments described below, an analogue or mimetic may be substituted for a claudin CAR sequence.

Modulating agents, or peptide portions thereof, may be linear or cyclic peptides. The term "cyclic peptide," as used herein, refers to a peptide or salt thereof that comprises (1) an intramolecular covalent bond between two non-adjacent residues, forming a peptide ring and (2) at least one claudin CAR sequence or an analogue thereof present within the peptide ring. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. Any of the above claudin CAR sequences, or an analogue or mimetic thereof, may be incorporated into a cyclic peptide, with or without one or more other adhesion molecule CAR sequences. Additional adhesion molecule CAR sequences are described in greater detail below.

The size of a cyclic peptide ring generally ranges from 5 to about 15 residues, preferably from 5 to 10 residues. Additional residue(s) may be present on the N-terminal and/or C-terminal side of a claudin CAR sequence, and may be derived from sequences that flank a CAR sequence, with or without amino acid substitutions and/or other modifications. Alternatively, additional residues present on one or both sides of the CAR sequence(s) may be unrelated to an endogenous sequence (e.g., residues that facilitate cyclization, purification or other manipulation and/or residues having a targeting or other function).

Within certain embodiments, a modulating agent may comprise a cyclic peptide that contains a claudin CAR sequence as provided in Table I (or a portion of such a CAR sequence). Certain cyclic peptides have the formula:

$$(Z_1)\text{-}(Y_1)\text{-}(X_1)\text{-}(W)\text{-}(X_2)\text{-}(Y_2)\text{-}(Z_2);$$

Within this formula, W is a tetrapeptide selected from the group consisting of IYSY (SEQ ID NO:2), TSSY (SEQ ID NO:3), VTAF (SEQ ID NO:4), MSSY (SEQ ID NO:386) and VSAF (SEQ ID NO:5); $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; $Y_1$ and $Y_2$ are independently selected from the group consisting of amino acid residues, and wherein a covalent bond is formed between residues $Y_1$ and $Y_2$; and $Z_1$ and $Z_2$ are optional, and if present, are independently selected from the group consisting of amino acid residues and combinations thereof in which the residues are linked by peptide bonds.

Cyclic peptides may comprise any of the above CAR sequence(s). Such cyclic peptides may be used as modulating agents without modification, or may be incorporated into a modulating agent. For example, a cyclic peptide may comprise any of the above claudin-1 CAR sequences. Representative cyclic peptides include CIYSYC (SEQ ID NO:59), CIYSYAC (SEQ ID NO:60), CIYSYAGC (SEQ ID NO:61), CKIYSYC (SEQ ID NO:62), CKIYSYAC (SEQ ID NO:63), CKIYSYAGC (SEQ ID NO:64), CWKIYSYC (SEQ ID NO:65), CWKIYSYAC (SEQ ID NO:66), CWKIYSYAGC (SEQ ID NO:67), KIYSYD (SEQ ID NO:68), KIYSYAD (SEQ ID NO:69), KIYSYAGD (SEQ ID NO:70), KKIYSYD (SEQ ID NO:71), KKIYSYAD (SEQ ID NO:72), KKIYSYAGD (SEQ ID NO:73), KWKIYSYD (SEQ ID NO:74), KWKIYSYAD (SEQ ID NO:75), KWKIYSYAGD (SEQ ID NO:76), KIYSYE (SEQ ID NO:77), KIYSYAE (SEQ ID NO:78), KIYSYAGE (SEQ ID NO:79), KKIYSYE (SEQ ID NO:80), KKIYSYAE (SEQ ID NO:81), KKIYSYAGE (SEQ ID NO:82), KWKIYSYE (SEQ ID NO:83), KWKIYSYAE (SEQ ID NO:84), KWKIYSYAGE (SEQ ID NO:85), DIYSYK (SEQ ID NO:86), DIYSYAK (SEQ ID NO:87), DIYSYAGK (SEQ ID NO:88), DKIYSYK (SEQ ID NO:89), DKIYSYAK (SEQ ID NO:90), DKIYSYAGK (SEQ ID NO:91), DWKIYSYK (SEQ ID NO:92), DWKIYSYAK (SEQ ID NO:93), DWKIYSYAGK (SEQ ID NO:94), EIYSYK (SEQ ID NO:95), EIYSYAK (SEQ ID NO:96), EIYSYAGK (SEQ ID NO:97), EKIYSYK (SEQ ID NO:98), EKIYSYAK (SEQ ID NO:99), EKIYSYAGK (SEQ ID NO:100), EWKIYSYK (SEQ ID NO:101), EWKIYSYAK (SEQ ID NO:102), EWKIYSYAGK (SEQ ID NO:103), IYSYA (SEQ ID NO:104), IYSYAG (SEQ ID NO:105), KIYSY (SEQ ID NO:106), KIYSYAG (SEQ ID NO:107), WKIYSY (SEQ ID NO:108), WKIYSYA (SEQ ID NO:109) or WKIYSYAG (SEQ ID NO:110). Within the context of the present invention, underlined sequences are cyclized using any suitable method, as described herein.

Similarly, cyclic peptides may comprise any of the above claudin-2 CAR sequences. Representative cyclic peptides include: CTSSYC (SEQ ID NO:111), CTSSYVC (SEQ ID NO:112), CTSSYVGC (SEQ ID NO:113), CRTSSYC (SEQ ID NO:114), CRTSSYVC (SEQ ID NO:115), CRTSSYVGC (SEQ ID NO:116), CWRTSSYC (SEQ ID NO:117), CWRTSSYVC (SEQ ID NO:118), CWRTSSYVGC (SEQ ID NO:119), KTSSYD (SEQ ID NO:120), KTSSYVD (SEQ ID NO:121), KTSSYVGD (SEQ ID NO:122), KRTSSYD (SEQ ID NO:123), KRTSSYVD (SEQ ID NO:124); KRTSSYVGD (SEQ ID NO:125), KWRTSSYD (SEQ ID NO:126), KWRTSSYVD (SEQ ID NO:127), KWRTSSYVGD (SEQ ID NO:128), KTSSYE (SEQ ID NO:129), KTSSYVE (SEQ ID NO:130), KTSSYVGE (SEQ ID NO:131), KRTSSYE (SEQ ID NO:132), KRTSSYVE (SEQ ID NO:133), KRTSSYVGE (SEQ ID NO:134), KWRTSSYE (SEQ ID NO:135), KWRTSSYVE (SEQ ID NO:136), KWRTSSYVGE (SEQ ID NO:137), DTSSYK (SEQ ID NO:138), DTSSYVK (SEQ ID NO:139), DTSSYVGK (SEQ ID NO:140), DRTSSYK (SEQ ID NO:141), DRTSSYVK (SEQ ID NO:142), DRTSSYVGK (SEQ ID NO:143), DWRTSSYK (SEQ ID NO:144), DWRTSSYVK (SEQ ID NO:145), DWRTSSYVGK (SEQ ID NO:146), ETSSYK (SEQ ID NO:147), ETSSYVK (SEQ ID NO:148), ETSSYVGK (SEQ ID NO:149), ERTSSYK (SEQ ID NO:150), ERTSSYVK (SEQ ID NO:151), ERTSSYVGK (SEQ ID NO:152), EWRTSSYK (SEQ ID NO:153), EWRTSSYVK (SEQ ID NO:154), EWRTSSYVGK (SEQ ID NO:155), TSSYV (SEQ ID NO:156), TSSYVG (SEQ ID NO:157), RTSSY (SEQ ID NO:158), RTSSYV (SEQ ID NO:159), RTSSYVG (SEQ ID NO:160), WRTSSY (SEQ ID NO:161), WRTSSYV (SEQ ID NO:162) and WRTSSYVG (SEQ ID NO:163).

Representative cyclic peptides comprising a claudin-3 CAR sequence include: CVSAFC (SEQ ID NO:217), CVSAFIC (SEQ ID NO:218), CVSAFIGC (SEQ ID NO:219), CRVSAFC (SEQ ID NO:220), CRVSAFIC (SEQ ID NO:221), CRVSAFIGC (SEQ ID NO:222), CWRVSAFC (SEQ ID NO:223), CWRVSAFIC (SEQ ID NO:224),CWRVSAFIGC (SEQ ID NO:225), KVSAFD (SEQ ID NO:226), KVSAFID (SEQ ID NO:227), KVSAFIGD (SEQ ID NO:228), KRVSAFD (SEQ ID NO:229), KRVSAFID (SEQ ID NO:230), KRVSAFIGD (SEQ ID NO:231), KWRVSAFD (SEQ ID NO:232), KWRVSAFID (SEQ ID NO:233), KWRVSAFIGD (SEQ ID NO:234), KVSAFE (SEQ ID NO:235), KVSAFIE (SEQ ID NO:236), KVSAFIGE (SEQ ID NO:237), KRVSAFE (SEQ ID NO:238), KRVSAFIE (SEQ ID NO:239), KRVSAFIGE (SEQ ID NO:240), KWRVSAFE (SEQ ID NO:241), KWRVSAFIE (SEQ ID NO:242), KWRVSAFIGE (SEQ ID NO:243), DVSAFK (SEQ ID NO:244), DVSAFIK (SEQ ID NO:245), DVSAFIGK (SEQ ID NO:246), DRVSAFK (SEQ ID NO:247), DRVSAFIK (SEQ ID NO:248), DRVSAFIGK (SEQ ID NO:249), DWRVSAFK (SEQ ID NO:250), DWRVSAFIK (SEQ ID NO:251), DWRVSAFIGK (SEQ ID NO:252), EVSAFK (SEQ ID NO:253), EVSAFIK (SEQ ID NO:254), EVSAFIGK (SEQ ID NO:255), ERVSAFK (SEQ ID NO:256), ERVSAFIK (SEQ ID NO:257), ERVSAFIGK (SEQ ID NO:258), EWRVSAFK (SEQ ID NO:259), EWRVSAFIK (SEQ ID NO:260), EWRVSAFIGK (SEQ ID NO:261), VSAFI (SEQ ID NO:262), VSAFIG (SEQ ID NO:263), RVSAF (SEQ ID NO:264), RVSAFI (SEQ ID NO:265), RVSAFIG (SEQ ID NO:266), WRVSAF (SEQ ID NO:267), WRVSAFI (SEQ ID NO:268) and WRVSAFIG (SEQ ID NO:269).

Any claudin-4 CAR sequence(s) may be formulated into a cyclic peptide. Representative cyclic peptides include: CVTAFC (SEQ ID NO:164), CVTAFIC (SEQ ID NO:165), CVTAFIGC (SEQ ID NO:166), CRVTAFC (SEQ ID NO:167), CRVTAFIC (SEQ ID NO:168), CRVTAFIGC (SEQ ID NO:169), CWRVTAFC (SEQ ID NO:170), CWRVTAFIC (SEQ ID NO:171), CWRVTAFIGC (SEQ ID NO:172), KVTAFD (SEQ ID NO:173), KVTAFID (SEQ ID NO:174), KVTAFIGD (SEQ ID NO:175), KRVTAFD (SEQ ID NO:176), KRVTAFID (SEQ ID NO:177), KRVTAFIGD (SEQ ID NO:178), KWRVTAFD (SEQ ID NO:179), KWRVTAFID (SEQ ID NO:180), KWRVTAFIGD (SEQ ID NO:181), KVTAFE (SEQ ID NO:182), KVTAFIE (SEQ ID NO:183), KVTAFIGE (SEQ ID NO:184), KRVTAFE (SEQ ID NO:185), KRVTAFIE (SEQ ID NO:186), KRVTAFIGE (SEQ ID NO:187), KWRVTAFE (SEQ ID NO:188), KWRVTAFIE (SEQ ID NO:189), KWRVTAFIGE (SEQ ID NO:190), DVATFK (SEQ ID NO:191), DVTAFIK (SEQ ID NO:192), DVTAFIGK (SEQ ID NO:193), DRVTAFK (SEQ ID NO:194), DRVTAFIK (SEQ ID NO:195), DRVTAFIGK (SEQ ID NO:196), DWRVTAFK (SEQ ID NO:197), DWRVTAFIK (SEQ ID NO:198), DWRVTAFIGK (SEQ ID NO:199), EVTAFK (SEQ ID NO:200), EVTAFIK (SEQ ID NO:201), EVTAFIGK (SEQ ID NO:202), ERVTAFK (SEQ ID NO:203), ERVTAFIK (SEQ ID NO:204), ERVTAFIGK (SEQ ID NO:205), EWRVTAFK (SEQ ID NO:206), EWRVTAFIK (SEQ ID NO:207), EWRVTAFIGK (SEQ ID NO:208), VTAFI (SEQ ID NO:209), VTAFIG (SEQ ID NO:210), RVTAF (SEQ ID NO:211), RVTAFI (SEQ ID NO:212), RVTAFIG (SEQ ID NO:213), WRVTAF (SEQ ID NO:214), WRVTAFI (SEQ ID NO:215) and WRVTAFIG (SEQ ID NO:216).

Representative cyclic peptides comprising a claudin-5 CAR sequence include: CVTAFC (SEQ ID NO:164), CVTAFLC (SEQ ID NO:278), CVTAFLDC (SEQ ID NO:279), CQVTAFC (SEQ ID NO:280), CQVTAFLC (SEQ ID NO:281), CQVTAFLDC (SEQ ID NO:282), CWQVTAFC (SEQ ID NO:283), CWQVTAFLC (SEQ ID NO:284), CWQVTAFLDC (SEQ ID NO:285), KVTAFD (SEQ ID NO:286), KVTAFLD (SEQ ID NO:287), KVTAFLDD (SEQ ID NO:288), KQVTAFD (SEQ ID NO:289), KQVTAFLD (SEQ ID NO:290), KQVTAFLDD (SEQ ID NO:291), KWQVTAFD (SEQ ID NO:292), KWQVTAFLD (SEQ ID NO:293), KWQVTAFLDD (SEQ ID NO:294), KVTAFE (SEQ ID NO:182), KVTAFLE (SEQ ID NO:295), KVTAFLDE (SEQ ID NO:296), KQVTAFE (SEQ ID NO:297), KQVTAFLE (SEQ ID NO:298), KQVTAFLDE (SEQ ID NO:299), KWQVTAFE (SEQ ID NO:300), KWQVTAFLE (SEQ ID NO:301), KWQVTAFLDE (SEQ ID NO:302), DVATFK (SEQ ID NO:303), DVTAFLK (SEQ ID NO:304), DVTAFLDK (SEQ ID NO:305), DQVTAFK (SEQ ID NO:306), DQVTAFLK (SEQ ID NO:307), DQVTAFLDK (SEQ ID NO:308), DWQVTAFK (SEQ ID NO:309), DWQVTAFLK (SEQ ID NO:310), DWQVTAFLDK (SEQ ID NO:311), EVTAFK (SEQ ID NO:200), EVTAFLK (SEQ ID NO:312), EVTAFLDK (SEQ ID NO:313), EQVTAFK (SEQ ID NO:314), EQVTAFLK (SEQ ID NO:315), EQVTAFLDK (SEQ ID NO:316), EWQVTAFK (SEQ ID NO:317), EWQVTAFLK (SEQ ID NO:318), EWQVTAFLDK (SEQ ID NO:319), VTAFL (SEQ ID NO:320), VTAFLD (SEQ ID NO:321), QVTAF (SEQ ID NO:322), QVTAFL (SEQ ID NO:323), QVTAFLD (SEQ ID NO:324), WQVTAF (SEQ ID NO:325), WQVTAFL (SEQ ID NO:326) and WQVTAFLD (SEQ ID NO:327).

Representative cyclic peptides comprising a claudin-6 CAR sequence include: CVTAFC (SEQ ID NO:164), CVTAFIC (SEQ ID NO:336), CVTAFIGC (SEQ ID NO:337), CKVTAFC (SEQ ID NO:338), CKVTAFIC (SEQ ID NO:339), CKVTAFIGC (SEQ ID NO:340), CWKVTAFC (SEQ ID NO:341), CWKVTAFIC (SEQ ID NO:342), CWKVTAFIGC (SEQ ID NO:343), KVTAFD (SEQ ID NO:344), KVTAFID (SEQ ID NO:345), KVTAFIGD (SEQ ID NO:346), KKVTAFD (SEQ ID NO:347), KKVTAFID (SEQ ID NO:348), KKVTAFIGD (SEQ ID NO:349), KWKVTAFD (SEQ ID NO:350), KWKVTAFID (SEQ ID NO:351), KWKVTAFIGD (SEQ ID NO:352), KVTAFE (SEQ ID NO:182), KVTAFIE (SEQ ID NO:353), KVTAFIGE (SEQ ID NO:354), KKVTAFE (SEQ ID NO:355), KKVTAFIE (SEQ ID NO:356), KKVTAFIGE (SEQ ID NO:357), KWKVTAFE (SEQ ID NO:358), KWKVTAFIE (SEQ ID NO:359), KWKVTAFIGE (SEQ ID NO:360), DVATFK (SEQ ID NO:361), DVTAFIK (SEQ ID NO:362), DVTAFIGK (SEQ ID NO:363), DKVTAFK (SEQ ID NO:364), DKVTAFIK (SEQ ID NO:365), DKVTAFIGK (SEQ ID NO:366), DWKVTAFK (SEQ ID NO:367), DWKVTAFIK (SEQ ID NO:368), DWKVTAFIGK (SEQ ID NO:369), EVTAFK (SEQ ID NO:200), EVTAFIK (SEQ ID NO:370), EVTAFIGK (SEQ ID NO:371), EKVTAFK (SEQ ID NO:372), EKVTAFIK (SEQ ID NO:373), EKVTAFIGK (SEQ ID NO:374), EWKVTAFK (SEQ ID NO:375), EWKVTAFIK (SEQ ID NO:376), EWKVTAFIGK (SEQ ID NO:377), VTAFI (SEQ ID NO:378), VTAFIG (SEQ ID NO:379), KVTAF (SEQ ID NO:380), KVTAFI (SEQ ID NO:381), KVTAFIG (SEQ ID NO:382), WKVTAF (SEQ ID NO:383), WKVTAFI (SEQ ID NO:384) and WKVTAFIG (SEQ ID NO:385).

Representative cyclic peptides comprising a claudin-7 CAR sequence include: CMSSYC (SEQ ID NO:395), CMSSYAC (SEQ ID NO:396), CMSSYAGC (SEQ ID NO:397), CQMSSYC (SEQ ID NO:398), CQMSSYAC (SEQ ID NO:399), CQMSSYAGC (SEQ ID NO:400), CWQMSSYC (SEQ ID NO:401), CWQMSSYAC (SEQ ID NO:402), CWQMSSYAGC (SEQ ID NO:403), KMSSYD (SEQ ID NO:404), KMSSYAD (SEQ ID NO:405), KMSSYAGD (SEQ ID NO:406), KQMSSYD (SEQ ID NO:407), KQMSSYAD (SEQ ID NO:408), KQMSSYAGD (SEQ ID NO:409), KWQMSSYD (SEQ ID NO:410), KWQMSSYAD (SEQ ID NO:411), KWQMSSYAGD (SEQ ID NO:412), KMSSYE (SEQ ID NO:413), KMSSYAE (SEQ ID NO:414), KMSSYAGE (SEQ ID NO:415), KQMSSYE (SEQ ID NO:416), KQMSSYAE (SEQ ID NO:417), KQMSSYAGE (SEQ ID NO:418), KWQMSSYE (SEQ ID NO:419), KWQMSSYAE (SEQ ID NO:420), KWQMSSYAGE (SEQ ID NO:421), DMSSYK (SEQ ID NO:422), DMSSYAK (SEQ ID NO:423), DMSSYAGK (SEQ ID NO:424), DQMSSYK (SEQ ID NO:425), DQMSSYAK (SEQ ID NO:426), DQMSSYAGK (SEQ ID NO:427), DWQMSSYK (SEQ ID NO:428), DWQMSSYAK (SEQ ID NO:429), DWQMSSYAGK (SEQ ID NO:430), EMSSYK (SEQ ID NO:431), EMSSYAK (SEQ ID NO:432), EMSSYAGK (SEQ ID NO:433), EQMSSYK (SEQ ID NO:434), EQMSSYAK (SEQ ID NO:435), EQMSSYAGK (SEQ ID NO:436), EWQMSSYK (SEQ ID NO:437), EWQMSSYAK (SEQ ID NO:438), EWQMSSYAGK (SEQ ID NO:439), MSSYA (SEQ ID NO:440), MSSYAG (SEQ ID NO:441), QMSSY (SEQ ID NO:442), QMSSYA (SEQ ID NO:443), QMSSYAG (SEQ ID NO:444), WQMSSY (SEQ ID NO:445), WQMSSYA (SEQ ID NO:446) and WQMSSYAG (SEQ ID NO:447).

Representative cyclic peptides comprising a claudin-8 CAR sequence include: CVSAFC (SEQ ID NO:217), CVSAFIC (SEQ ID NO:218), CVSAFIEC (SEQ ID NO:451), CRVSAFC (SEQ ID NO:220), CRVSAFIC (SEQ ID NO:221), CRVSAFIEC (SEQ ID NO:452), CWRVSAFC (SEQ ID NO:223), CWRVSAFIC (SEQ ID NO:224), CWRVSAFIEC (SEQ ID NO:453), KVSAFD (SEQ ID NO:226), KVSAFID (SEQ ID NO:227), KVSAFIED (SEQ ID NO:454), KRVSAFD (SEQ ID NO:229), KRVSAFID (SEQ ID NO:230), KRVSAFIED (SEQ ID NO:455), KWRVSAFD (SEQ ID NO:232), KWRVSAFID (SEQ ID NO:233), KWRVSAFIED (SEQ ID NO:456), KVSAFE (SEQ ID NO:235), KVSAFIE (SEQ ID NO:236), KVSAFIEE (SEQ ID NO:457), KRVSAFE (SEQ ID NO:238), KRVSAFIE (SEQ ID NO:239), KRVSAFIEE (SEQ ID NO:458), KWRVSAFE (SEQ ID NO:241), KWRVSAFIE (SEQ ID NO:242), KWRVSAFIEE (SEQ ID NO:459), DVSAFK (SEQ ID NO:244), DVSAFIK (SEQ ID NO:245), DVSAFIEK (SEQ ID NO:460), DRVSAFK (SEQ ID NO:247), DRVSAFIK (SEQ ID NO:248), DRVSAFIEK (SEQ ID NO:461), DWRVSAFK (SEQ ID NO:250), DWRVSAFIK (SEQ ID NO:251), DWRVSAFIEK (SEQ ID NO:462), EVSAFK (SEQ ID NO:253), EVSAFIK (SEQ ID NO:254), EVSAFIEK (SEQ ID NO:463), ERVSAFK (SEQ ID NO:256), ERVSAFIK (SEQ ID NO:257), ERVSAFIEK (SEQ ID NO:464), EWRVSAFK (SEQ ID NO:259), EWRVSAFIK (SEQ ID NO:260), EWRVSAFIEK (SEQ ID NO:465), VSAFI (SEQ ID NO:262), VSAFIE (SEQ ID NO:466), RVSAF (SEQ ID NO:264), RVSAFI (SEQ ID NO:265), RVSAFIE (SEQ ID NO:467), WRVSAF (SEQ ID NO:267), WRVSAFI (SEQ ID NO:268) and WRVSAFIE (SEQ ID NO:468).

Figure 2B:
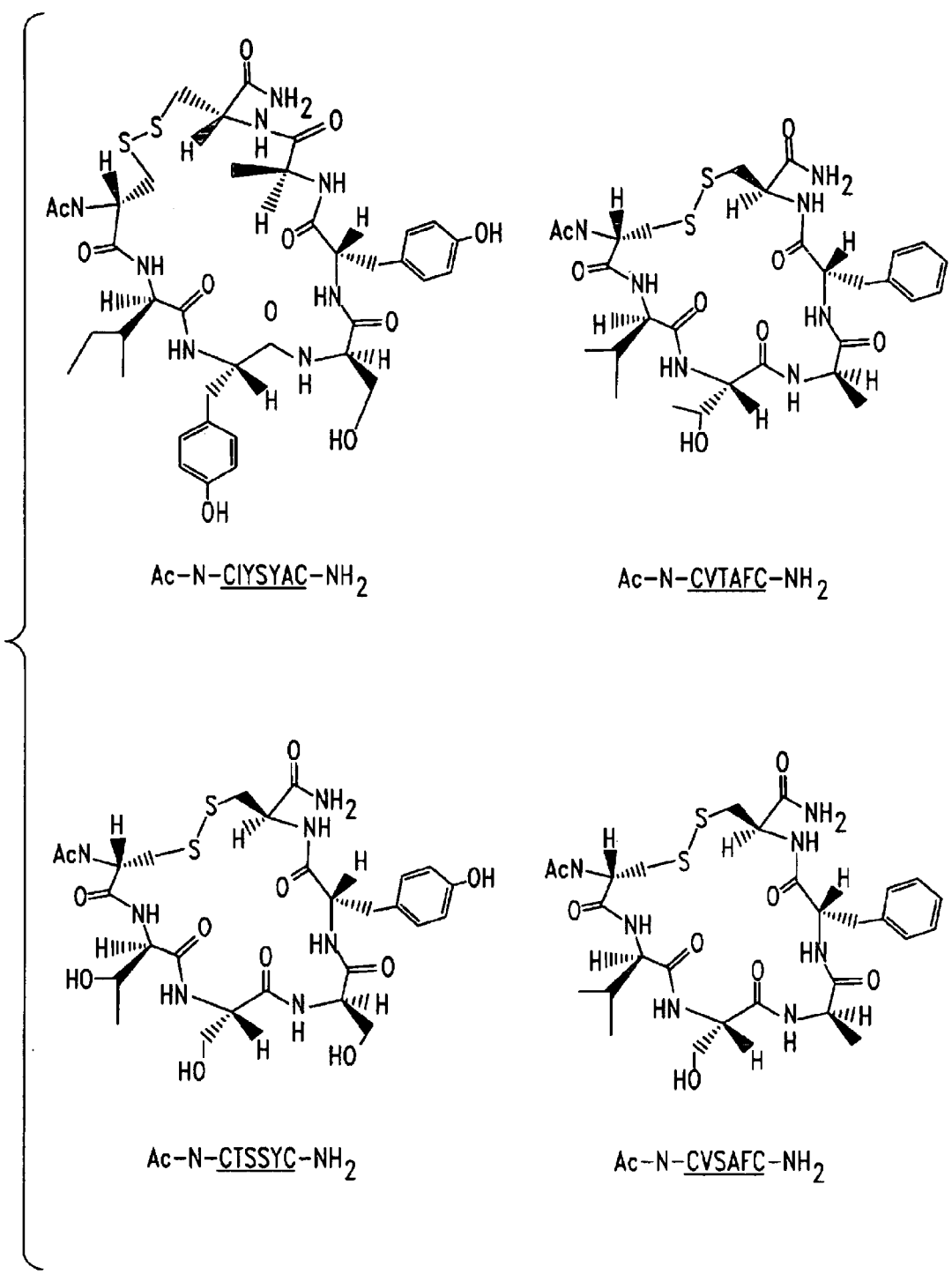

Within certain embodiments, as discussed below, cyclic peptides that contain small CAR sequences (e.g., four residues without significant flanking sequences) are preferred for modulating claudin-mediated functions. Such peptides may contain an N-acetyl group and a C-amide group (e.g., the 6-residue ring N-Ac-CIYSYC-NH$_2$ (SEQ ID NO:59) or N-Ac-KIYSYD-NH$_2$ (SEQ ID NO:68), for modulating claudin-1 mediated functions). Small cyclic peptides may generally be used to specifically modulate adhesion of cancer and/or other cell types by topical administration or by systemic administration, with or without linking a targeting agent to the peptide, as discussed below. Certain representative cyclic peptides comprising a claudin CAR sequence are shown in FIGS. 2A and 2B. Within other preferred embodiments, a cyclic peptide may contain sequences that flank the claudin CAR sequence on one or both sides, which may result in increased potency. Suitable flanking sequences include, but are not limited to, an endogenous sequence present in a naturally occurring claudin. To facilitate the preparation of cyclic peptides having increased potency, nuclear magnetic resonance (NMR) and computational techniques may be used to determine the conformation of a peptide that confers increased potency, as described above.

Within embodiments in which inhibition of a claudin interaction is desired, a modulating agent may contain one claudin CAR sequence, or multiple CAR sequences that are adjacent to one another (i.e., without intervening sequences) or in close proximity (i.e., separated by peptide and/or non-peptide linkers to give a distance between the claudin CAR sequences that ranges from about 0.1 to 400 nm). For example, a modulating agent with adjacent IYSY (SEQ ID NO:2) sequences may comprise the peptide IYSYIYSY (SEQ ID NO:14). A representative modulating agent with IYSY (SEQ ID NO:2) sequences in close proximity may comprise the sequence KIYSYKIYSYKIYSY (SEQ ID NO:15). A linker may be any molecule (including peptide and/or non-peptide sequences) that does not contain a CAR sequence and that can be covalently linked to at least two peptide sequences. Using a linker, CAR sequence-containing peptides and other peptide or protein sequences may be joined end-to-end (i.e., the linker may be covalently attached to the carboxyl or amino group of each peptide sequence), and/or via side chains. One linker that can be used for such purposes is (H$_2$N(CH$_2$)$_n$CO$_2$H), or derivatives thereof, where n ranges from 1 to 4. Other linkers that may be used will be apparent to those of ordinary skill in the art. Peptide and non-peptide linkers may generally be incorporated into a modulating agent using any appropriate method known in the art.

Within embodiments in which enhancement of cell adhesion mediated by a claudin is desired, a modulating agent may contain multiple claudin CAR sequences, or antibodies that specifically bind to such sequences, joined by linkers as described above. For enhancers of claudin function, the linker distance should generally be 400–10,000 nm. One linker that can be used for such purposes is (H$_2$N(CH$_2$)$_n$CO$_2$H)$_m$, or derivatives thereof, where n ranges from 1 to 10 and m ranges from 1 to 4000. For example, if glycine (H$_2$NCH$_2$CO$_2$H) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Enhancement of cell adhesion may also be achieved by attachment of multiple modulating agents to a support material, as discussed further below.

A modulating agent as described herein may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the claudin CAR sequence(s) and/or each other. Such modulating agents may generally be used within methods in which it is desirable to simultaneously disrupt cell adhesion mediated by multiple adhesion molecules. For cyclic peptides, additional CAR sequences may be present within the cyclic peptide ring, within a separate cyclic peptide component of the modulating agent and/or in a non-cyclic portion of the modulating agent. Antibodies and antigen-binding fragments thereof are typically present in a non-cyclic portion of the modulating agent.

As used herein, an "adhesion molecule" is any molecule that mediates cell adhesion via a receptor on the cell's surface. Adhesion molecules include cell adhesion proteins (e.g., classical cadherins, other members of the cadherin gene superfamily that are not classical cadherins (such as atypical cadherins (e.g., VE-cadherin and PB-cadherin), desmogleins (Dsg) and desmocollins (Dsc)); integrins; occludin; and members of the immunoglobulin supergene family, such as N-CAM, JAM and PECAM). Preferred CAR sequences for inclusion within a modulating agent include His-Ala-Val (HAV), which is bound by classical cadherins (Munro S B et al., 1996, In: *Cell Adhesion and Invasion in Cancer Metastasis,* P. Brodt, ed., pp. 17–34 (R G Landes Company, Austin Tex.); Arg-Gly-Asp (RGD), which is bound by integrins (see Cardarelli et al., *J. Biol. Chem.* 267:23159–64, 1992); KYSFNYDGSE (SEQ ID NO:16), which is bound by N-CAM; SFTIDPKSG (SEQ ID NO:477) or DPK, which is bound by JAM, the occludin CAR sequence LYHY (SEQ ID NO:17); and/or one or more nonclassical cadherin CAR sequences, such as the VE-cadherin CAR sequence DAE, the Dsc CAR sequences IEK, VER and IER, or the Dsg CAR sequences INQ, INR and LNK.

Using linkers, claudin CAR sequence-containing peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure may comprise a claudin CAR sequence and an occludin CAR sequence. Alternatively, a branched structure may comprise three different CAR sequences, such as RGD, a claudin CAR sequence and HAV. Within another embodiment, modulating agents having a branched structure comprise a claudin CAR sequence, along with one or more of HAV, RGD, LYHY (SEQ ID NO:17), DAE, DPK, IEK, VER, IER, INQ, INR and/or LNK.

Other combinations of CAR sequences are also possible. Linkers preferably produce a distance between CAR sequences between 0.1 to 10,000 nm, more preferably about 0.1–400 nm. A separation distance between recognition sites may generally be determined according to the desired function of the modulating agent, as discussed above.

The total number of CAR sequences (including claudin CAR sequence(s)), with or without other CAR sequences derived from one or more adhesion molecules) present within a modulating agent may range from 1 to a large number, such as 100, preferably from 1 to 10, and more preferably from 1 to 5. Peptide modulating agents comprising multiple CAR sequences typically contain from 6 to about 1000 amino acid residues, preferably from 6 to 50 residues. When non-peptide linkers are employed, each CAR sequence of the modulating agent is present within a peptide that generally ranges in size from 4 to 50 residues in length, preferably from 4 to 25 residues, more preferably from 4 to 16 residues and still more preferably from 4 to 15 residues.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations, and the corresponding D-amino acids are designated by a lower case one letter symbol.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe$ (CN)$_6$ can be usede to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike I$_2$ and K$_3$Fe(CN)$_6$, is a mild oxidizing agent which does not cause oxidative side reactions of the nucleophilic amino acids mentioned above. DMSO is miscible with H$_2$O at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the underlined portion is cyclized, N-acetyl groups are indicated by N-Ac and C-terminal amide groups are represented by —NH$_2$:

N-Ac-<u>Cys-Ile-Tyr-Ser-Tyr-Cys</u>-NH$_2$ (SEQ ID NO:59)  i)

H-<u>Cys-Ile-Tyr-Ser-Tyr-Cys</u>-OH (SEQ ID NO:59)  ii)

N-Ac-<u>Cys-Trp-Lys-Ile-Tyr-Ser-Tyr-Cys</u>-NH$_2$ (SEQ ID NO:65)  iii)

H-<u>Cys-Trp-Lys-Ile-Tyr-Ser-Tyr-Cys</u>-OH (SEQ ID NO:65)  iv)

N-Ac-<u>Cys-Lys-Ile-Tyr-Ser-Tyr-Cys</u>-NH, (SEQ ID NO:62)  v)

H-<u>Cys-Lys-Ile-Tyr-Ser-Tyr-Cys</u>-OH (SEQ ID NO:62)  vi)

N-Ac-<u>Cys-Ile-Tyr-Ser-Tyr-Pen</u>-NH$_2$ (SEQ ID NO:18)  vii)

N-Ac-<u>Tmc-Ile-Tyr-Ser-Tyr-Cys</u>-NH$_2$ (SEQ ID NO:19)  viii)

N-Ac-<u>Pmc-Ile-Tyr-Ser-Tyr-Cys</u>-NH$_2$ (SEQ ID NO:20)  ix)

N-Ac-<u>Mpr-Ile-Tyr-Ser-Tyr-Cys</u>-NH$_2$ (SEQ ID NO:21)  x)

N-Ac-<u>Pmp-Ile-Tyr-Ser-Tyr-Cys</u>-NH$_2$ (SEQ ID NO:22)  xi)

It will be readily apparent to those of ordinary skill in the art that, within each of these representative formulas, any of the above thiol-containing residues may be employed in place of one or both of the thiol-containing residues recited.

Within another embodiment, cyclization may be achieved by amide bond formation. For example, a peptide bond may be formed between terminal functional groups (i.e., the amino and carboxy termini of a linear peptide prior to cyclization), as in <u>KIYSY</u> (SEQ ID NO:106). Within another such embodiment, the cyclic peptide comprises a D-amino acid (e.g., <u>yIYSY</u>; SEQ ID NO:23). Alternatively, cyclization may be accomplished by linking one terminus and a residue side chain or using two side chains, as in <u>KIYSYD</u> (SEQ ID NO:68), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment; a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i.

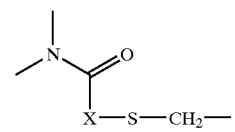

X = (CH$_2$)$_4$
= CH$_2$

= 

ii.

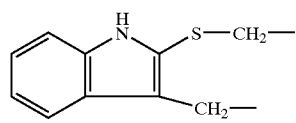

Cyclization may also be achieved using $\delta_1,\delta_1$-Ditryptophan (i.e., Ac-Trp-Gly-Gly-Trp-OMe) (SEQ ID NO:24), as shown below:

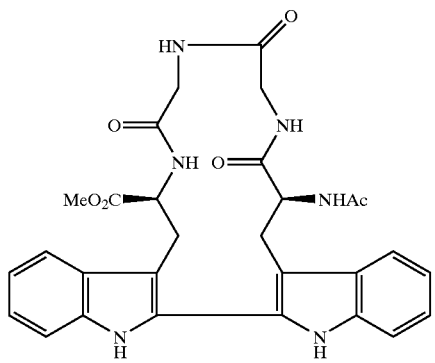

Representative structures of cyclic peptides are provided in FIGS. 2A and 2B. The structures and formulas recited herein are provided solely for the purpose of illustration, and are not intended to limit the scope of the cyclic peptides described herein.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous claudin or other adhesion molecule. Such sequences may be prepared based on known cDNA or genomic sequences, or from sequences isolated by screening an appropriate library with probes designed based on known claudin sequences. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous claudin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, polynucleotides may also function as modulating agents. In general, such polynucleotides should be formulated to permit expression of a polypeptide modulating agent following administration to a mammal. Such formulations are particularly useful for therapeutic purposes, as described below. Those of ordinary skill in the art will appreciate that there are many ways to achieve expression of a polynucleotide within a mammal, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transfected cells) and/or a targeting moiety, such as a gene that encodes a ligand for a receptor on a specific target cell, to render the vector target specific. Targeting may also be accomplished using an antibody, by methods known to those of ordinary skill in the art. Other formulations for polynucleotides for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

As noted above, instead of (or in addition to) a claudin CAR sequence, a modulating agent may comprise an antibody, or antigen-binding fragment thereof, that specifically binds to a claudin CAR sequence. As used herein, an antibody, or antigen-binding fragment thereof, is said to "specifically bind" to a claudin CAR sequence (with or without flanking amino acids) if it reacts at a detectable level with a peptide containing that sequence, and does not react detectably with peptides containing a different CAR sequence or a sequence in which the order of amino acid residues in the claudin CAR sequence and/or flanking sequence is altered. Such antibody binding properties may be assessed using an ELISA, as described by Newton et al., *Develop. Dynamics* 197:1–13, 1993.

Polyclonal and monoclonal antibodies may be raised against a claudin CAR sequence using conventional techniques. See, e.g, Harlow and Lane, *Antibodies: A Laboratory Manual,* Cold Spring Harbor Laboratory, 1988. In one such technique, an immunogen comprising the claudin CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for the claudin CAR sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target claudin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

As noted above, modulating agents as described herein are capable of modulating claudin-mediated cell adhesion. The ability of an agent to modulate cell adhesion may generally be evaluated in vitro by assaying the effect on endothelial and/or epithelial cell adhesion or cells transfected with claudin cDNA, such as L cells (Furuse et al. *J Cell Biol.* 143:391–401, 1998), using, for example, any of a variety of immunostaining protocols and/or plating assays. In general, a modulating agent is an inhibitor of cell adhesion if contact of the test cells with the modulating agent results in a discernible disruption of cell adhesion using one or more representative assays provided herein. Modulating agents that enhance cell adhesion (e.g., agents comprising multiple claudin CAR sequences and/or linked to a support molecule or material) are considered to be modulators of cell adhesion if they are capable of promoting cell adhesion, as judged by plating assays to assess either endothelial or epithelial cell adhesion to a modulating agent attached to a support material, such as tissue culture plastic.

An initial screen for the ability to modulate one or more claudin-mediated functions may be performed by evaluating the ability of a modulating agent to bind to a claudin using any binding assay known to those of ordinary skill in the art. For example, a Pharmacia Biosensor machine may be used, as discussed in Jonsson et al., *Biotechniques* 11:520–27, 1991. For example, a modulating agent may comprise a CAR sequence that binds to a claudin. A specific example of a technology that measures the interaction of peptides with molecules can be found in Williams et al., *J. Biol. Chem.* 272, 22349–22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 μg/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with claudin derivatized to biotin. Any non-specifically bound protein is removed.

To determine binding, test analytes (e.g., peptides containing the claudin CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to a claudin at a detectable level within such as assay. The level of binding is preferably at least that observed for the full length claudin under similar conditions.

The ability of an agent to modulate cell adhesion may generally be evaluated in vivo by assessing the effect on vascular permeability utilizing the Miles assay (McClure et al., *J. Pharmacological & Toxicological Methods* 32:49–52, 1994). Briefly, a candidate modulating agent may be dissolved in phosphate buffered saline (PBS) at a concentration of 100 μg/ml. Adult rats may be given 100 μl subdermal injections of each peptide solution into their shaved backs, followed 15 minutes later by a single 250 μl injection of 1% Evans blue dissolved in PBS into their tail veins. The subdermal injection sites may be visually monitored for the appearance of blue dye. Once the dye appears (about 15 minutes after injection), each subdermal injection site may be excised, weighed, and placed in 1 ml dimethylformamide for 24 hours to extract the dye. The optical density of the dye extracts may then be determined at 620 nm. In general, the injection of 0.1 ml of modulating agent (at a concentration of 0.1 mg/ml) into the backs of rats causes an increase of dye accumulation at the injection sites of at least 50%, as compared to dye accumulation at sites into which PBS has been injected.

The effect of a modulating agent on endothelial cell adhesion may generally be evaluated using immunolocalization techniques. Human aortic endothelial cells (HAEC) may be cultured on fibronectin-coated coverslips (fibronectin may be obtained from Sigma, St. Louis, Mo.) according to the procedures of Jaffe et al., *J. Clin. Invest.* 52:2745–2756, 1973. Briefly, human endothelial cells may be maintained in EGM (endothelial cell growth medium; Clonetics, San Diego, Calif.) and used for experiments at passage 4. Confluent cultures of HAEC may be exposed to either a candidate modulating agent (final concentration 100 μg/ml EGM), or EGM alone for 1 hour. The cells are then be fixed for 30 minutes at 4° C. in 95% ethanol, followed by fixation in acetone for 1 minute at 4° C. (Furuse et al., *J. Cell Biol.* 123:1777–1788, 1993). After fixation, the cells may be probed with either mouse anti-VE-cadherin antibodies (Hemeris, Sassenage, France; diluted 1:250 in 0.1% dried skim milk powder dissolved in PBS), or anti-claudin antibodies (prepared as described by Morita et al., *Proc. Natl. Acad. Sci. USA* 96:511–516, 1999) diluted in 0.1% dried skim milk powder dissolved in PBS) for 1 hour at 37° C. The cells may then be washed with 0.1% dried skim milk powder dissolved in PBS (three washes, 5 minutes/wash), and probed with secondary antibodies (donkey anti-mouse Cy3, or donkey anti-rabbit Cy5 diluted 1:250 in 0.1% dried skim milk powder dissolved in PBS; Jackson Immunoresearch Laboratories Inc., Westgrove, Pa.) for 1 hour at 37° C. The cells may then be washed again with in 0.1% dried skim milk powder dissolved in PBS and mounted in a solution composed of 50% glycerol and 50% PBS to which phenylenediamine (Sigma, St. Louis, Mo.) has been added to a final concentration of 1 mg/ml. The sample may then be analyzed using a Bio-Rad MRC 1000 confocal microscope with Laser Sharp software version 2.1T (Bio-Rad, Hercules, Calif.). In general, 0.1 mg/ml of modulating agent results in the appearance of intercellular gaps within the monolayer cultures and a decrease of at least 50% in the surface expression of claudin and VE-cadherin, as compared to monolayer cultures that were not exposed to the modulating agent.

Within certain cell adhesion assays, the addition of a modulating agent to cells that express claudin results in disruption of cell adhesion. A "claudin-expressing cell," as used herein, may be any type of cell that expresses claudin on the cell surface at a detectable level, using standard techniques such as immunocytochemical protocols (e.g, Blaschuk and Farookhi, *Dev. Biol.* 136:564–567, 1989). Claudin-expressing cells include endothelial, epithelial and/or or cancer cells. For example, such cells may be plated under standard conditions that, in the absence of modulating agent, permit cell adhesion. In the presence of modulating agent (e.g, 100 μg/mL), disruption of cell adhesion may be determined visually within 24 hours, by observing retraction of the cells from one another.

Within another such assay, the effect of a modulating agent on normal rat kidney (NRK) cells may be evaluated. According to a representative procedure, NRK cells (ATCC #1571-CRL) may be plated at 10–20,000 cells per 35 mm tissue culture flasks containing DMEM with 10% FCS and sub-cultured periodically (Laird et al., *J. Cell Biol.* 131:1193–1203, 1995). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 0.1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of anti-claudin antibody and mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse Cy3 and donkey anti-rabbit Cy5 (Jackson Immunoresearch Laboratories Inc., Westgrove, Pa.) for 1 hour at 37° C. Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts claudin-mediated cell adhesion may assume a non-polygonal and elongated morphology (i.e., a fibroblast-like shape) within 48 hours of treatment with 0.1 mg/mL of modulating agent. Gaps appear in confluent cultures of such cells. In addition, 0.1 mg/mL of such a modulating agent reproducibly induces a readily apparent reduction in cell surface staining of claudin and E-cadherin, as judged by immunofluorescence microscopy (Laird et al., *J. Cell Biol.* 131:1193–1203, 1995), preferably at least 75% within 48 hours.

A third cell adhesion assay involves evaluating the effect of a modulating agent on permeability of adherent endothelial cell monolayers. The effects of a modulating agent on the permeability of endothelial cell monolayers may be assessed utilizing the protocols of Ehringer et al., *J. Cell Physiol.* 167:562–569, 1996. HAEC can be seeded onto inserts in 24-well plates (Becton-Dickenson, Franklin Lake, N.J.) and cultured in EGM. Confluent cell monolayers may be exposed to either modulating agent (final concentration 100 μg/ml EGM), or EGM alone for 1 hour. The inserts may then be transferred to 24-chamber plates (Becton-Dickenson) for permeability assays. Perfusate (0.5% bovine serum albumin, fraction V (Sigma) dissolved in 15 mM HEPES, pH 7.4) and FITC-Dextran (50 μg/ml HEPES buffer; MW 12 kDa; Sigma) may be added to each well (1 ml/well and 50 μl/well, respectively), and the cells incubated at 37° C. for 30 min. Aliquots of 100 μl may then be removed from the lower chamber and the optical density of the solution determined at a wavelength of 450 nm. In general, the presence of 100 μg/mL modulating agent that enhances the permeability of endothelial cell monolayers results in a statistically significant increase in the amount of marker in the receptor compartment after 1 hour.

Alternatively, cells that do not naturally express a claudin may be used within such assays. Such cells may be stably transfected with a polynucleotide (e.g., a cDNA) encoding a claudin of interest, such that the claudin is expressed on the surface of the cell. Transfection of cells for use in cell adhesion assays may be performed using standard techniques and published claudin sequences. Expression of the claudin may be confirmed by assessing adhesion of the transfected cells, in conjunction with immunocytochemical techniques using antibodies directed against the claudin of interest. The stably transfected cells that aggregate, as judged by light microscopy, following transfection express sufficient levels of the claudin. Preferred cells for use in such assays include L cells, which do not detectably adhere in the absence of transfection (Nagafuchi et al., *Nature* 329:341–343, 1987). Following transfection of L cells with a cDNA encoding a claudin, cell adhesion may be observed (Furuse et al *J Cell Biol.* 143:391–401, 1998). Modulating agents that detectably inhibit such aggregation may be used to modulate functions mediated by the claudin. Such assays have been used for numerous nonclassical cadherins, including OB-cadherin (Okazaki et al., *J. Biol. Chem.* 269:12092–98, 1994), cadherin-5 (Breier et al., *Blood* 87:630–641, 1996), cadherin-6 (Mbalaviele et al., *J. Cell. Biol.* 141:1467–1476, 1998), cadherin-8 (Kido et al., *Genomics* 48:186–194, 1998), cadherin-15 (Shimoyama et al., *J. Biol. Chem.* 273:10011–10018, 1998), PB-cadherin (Sugimoto et al., *J. Biol. Chem.* 271:11548–11556, 1996), LI-cadherin (Kreft et al., *J. Cell. Biol.* 136:1109–1121, 1997), protocadherin 42 and 43 (Sano et al., *EMBO J.* 12:2249–2256, 1993) and desmosomal cadherins (Marcozzi et al., *J. Cell. Sci.* 111:495–509, 1998). It will be apparent to those of ordinary skill in the art that assays may be performed in a similar manner for claudins. In general, a modulating agent that is derived from a particular claudin CAR sequence (i.e., comprises such a CAR sequence, or an analog or mimetic thereof, or an antibody that specifically recognizes such a CAR sequence) and that modulates adhesion of a cell that expresses the same claudin is considered to modulate a function mediated by the claudin.

Yet another assay evaluates the effect of a modulating agent on the electrical resistance across a monolayer of cells. For example, Madin Darby canine kidney (MDCK) cells can be exposed to the modulating agent dissolved in medium (e.g., at a final concentration of 0.5 mg/ml for a period of 24 hours). The effect on electrical resistance can be measured using standard techniques. This assay evaluates the effect of a modulating agent on tight junction formation in epithelial cells. In general, the presence of 500 μg/mL modulating agent should result in a statistically significant decrease in electrical resistance after 24 hours.

Modulating Agent Modification and Formulations

A modulating agent as described herein may, but need not, be linked to one or more additional molecules. In particular as discussed below, it may be beneficial for certain applications to link multiple modulating agents (which may, but need not, be identical) to a support material, such as a single molecule (e.g, keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an HAV sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. For example, in receptor-mediated delivery, a modulating agent may be linked to a ligand that recognizes a specific receptor on the surface of a target cell. In certain instances, modulating, agent is released within the cell following cleavage with intracellular enzymes. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, –Fab', Fab and F[v] fragments, which may be produced by conventional methods or by genetic or protein engineering. Linkage is generally covalent and may be achieved by, for example, direct condensation or other reactions, or by way of bi- or multi-functional linkers.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than claudin. Such modulators may generally be prepared as described above, except that one or more non-claudin CAR sequences and/or antibodies thereto are substituted for the claudin CAR sequence. Such compositions are particularly useful for situations in which it is desirable to inhibit cell adhesion mediated by multiple cell adhesion molecules, such as other members of the cadherin gene superfamily (e.g., classical cadherins such as E-cadherin and/or nonclassical cadherins such as VE-cadherin, Dsg and Dsc); integrins; members of the immunoglobulin supergene family, such as N-CAM, JAM and PECAM. Preferred CAR sequences for use within such a modulator include HAV, RGD, DDK, EEY, EAQ (OB-cads), DPK (JAM), DAE (VE-cad), IEK, VER, IER, INQ, INR and/or LNK. Also preferred is the occludin CAR sequence LYHY (SEQ ID NO:17).

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antipsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably from 0.0001% to 0.2% and more preferably from 0.01% to 0.1%. Fluid compositions typically contain an amount of modulating agent ranging from 10 ng/ml to 5 mg/ml, preferably from 10 μg to 2 mg/mL. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of claudin-expressing cells in vitro and/or in vivo, preferably in a mammal such as a human, by contacting the claudin-expressing cell with the modulating agent. As noted above, modulating agents for purposes that involve the disruption of claudin-mediated cell adhesion may comprise a claudin CAR sequence, multiple claudin CAR sequences in close proximity and/or an antibody (or an antigen-binding fragment thereof) that recognizes the claudin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the claudin CAR sequence by linkers. As noted above, such linkers may or may not comprise one or more amino acids. For enhancing cell adhesion, a modulating agent may contain multiple claudin CAR sequences or antibodies (or fragments), preferably separated by linkers, and/or may be linked to a single molecule or to a support material as described above. When it is desirable to also enhance cell adhesion mediated by other adhesion molecules, a modulating agent may additionally comprise one or more CAR sequences bound by such adhesion molecules (and/or antibodies or fragments thereof that bind such sequences), preferably separated from each other and from the claudin CAR sequence by linker.

Certain methods involving the disruption of cell adhesion as described herein have an advantage over prior techniques in that they permit the passage of molecules that are large and/or charged across barriers of claudin-expressing cells. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

The present invention provides, within certain aspects, methods for increasing vasopermeability in a mammal by administering one or more modulating agents or pharmaceutical compositions. Endothelial cell adhesion may be disrupted by linear and cyclic peptides containing a claudin CAR sequence. Within blood vessels, endothelial cell adhesion results in decreased vascular permeability. Accordingly, modulating agents that disrupt claudin-mediated cell adhesion as described herein, can increase vascular permeability and thus may facilitate drug delivery to previously inaccessible tissues, such as the brain. In one particularly preferred embodiment, a modulating agent for use within such methods is capable of disrupting cell adhesion mediated by multiple adhesion molecules. For example, a single branched modulating agent (or multiple agents linked to a single molecule or support material) may disrupt claudin, occludin and cadherin mediated cell adhesion, thereby disrupting tight junctions and adherens junctions. Trifunctional modulating agents comprising a claudin CAR sequence joined to the cadherin CAR sequence HAV, and the occludin CAR sequence LYHY, preferably by a linker, are also preferred. Alternatively, a separate modulator of non-claudin-mediated cell adhesion may be administered in conjunction with the modulating agent(s), either within the same pharmaceutical composition or separately. Preferred antibody modulating agents that may be used in conjunction with the claudin modulating agents include Fab fragments directed against an N-cadherin CAR sequence, such as FHLRAHAVDINGNQV-NH$_2$ (SEQ ID NO:25), an occludin CAR sequence, such as QYLYHYCVVD-NH$_2$ (SEQ ID NO:478), or an OB-cadherin CAR sequence, such as IFVIDDKSG-NH$_2$ (SEQ ID NO:479).

Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. In one particularly preferred embodiment, a modulating agent is capable of disrupting cell adhesion mediated by multiple adhesion molecules. For example, a single branched modulating agent (or multiple agents linked to a single molecule or support material) may disrupt claudin, occludin, classical cadherin, integrin, and nonclassical cadherin (e.g., Dsc and/or Dsg) mediated cell adhesion, thereby disrupting tight junctions, adherens junctions, focal contacts and desmosomes. Multifunctional modulating agents comprising a claudin CAR sequence linked to one or more of the classical cadherin CAR sequence HAV; the sequence RGD, which is bound by integrins; the sequence LYHY, which is bound by occludin, and/or a nonclassical cadherin CAR sequence, such as a Dsc CAR sequence (IEK, VER or IER) and/or a Dsg CAR sequence (INQ, INR or LNK), may be used to disrupt cell adhesion. Alternatively, a separate modulator of non-claudin-mediated cell adhesion may be administered in conjunction with the modulating agent(s), either within the same pharmaceutical composition or separately. Preferred antibody modulating agents that may be used in conjunction with the claudin modulating agents include Fab fragments directed against either an N-cadherin CAR sequence, such as FHLRAHAVDINGNQV-NH$_2$ (SEQ ID NO:25), an E-cadherin CAR sequence, such as LFSHAVSSNG-NH$_2$ (SEQ ID NO:26), an occludin CAR sequence, such as QYLYHYCVVD-NH$_2$ (SEQ ID NO:478), or an OB-cadherin CAR sequence, such as IFVIDDKSG-NH$_2$ (SEQ ID NO:479).

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within certain aspects, methods are provided in which cell adhesion is diminished. In one such aspect, the present invention provides methods for reducing unwanted cellular adhesion in a mammal by administering a modulating agent as described herein. Unwanted cellular adhesion can occur, for example, between tumor cells, between tumor cells and normal cells or between normal cells as a result of surgery, injury, chemotherapy, disease, inflammation or other condition jeopardizing cell viability or function. Certain preferred modulating agents for use within such methods comprise one or more of the claudin CAR sequences provided herein. In one particularly preferred embodiment, a modulating agent is further capable of disrupting cell adhesion mediated by multiple adhesion molecules. Such an agent may comprise, in addition to one or more claudin CAR sequences, CAR sequences such as the classical cadherin CAR sequence HAV sequence, an RGD sequence, which is bound by integrins; and/or the occludin CAR sequence LYHY (SEQ ID NO:17), preferably separated from the claudin CAR sequence via a linker. Alternatively, separate modulators of cell adhesion mediated by other adhesion molecules may be administered in conjunction with the modulating agent(s), either within the same pharmaceutical composition or separately.

Topical administration of the modulating agent(s) is generally preferred, but other means may also be employed. Preferably, a fluid composition for topical administration (comprising, for example, physiological saline) comprises an amount of modulating agent as described above, and more preferably from 10 µg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within another such aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be, delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Within certain embodiments, multifunctional modulating agents comprising a claudin CAR sequence linked to one or more of the classical cadherin CAR sequence HAV; the sequence RGD, which is bound by integrins; and/or a nonclassical cadherin CAR sequence, such as a Dsc CAR sequence (IEK, VER or IER) and/or a Dsg CAR sequence (INQ, INR or LNK), may also be used to disrupt cell adhesion. Alternatively, a separate modulator of non-claudin-mediated cell adhesion may be administered in conjunction with the modulating agent(s), either within the same pharmaceutical composition or separately. Contact may be achieved by direct application of the modulating agent, generally within a composition formulated as a cream or gel, or using any of a variety of skin contact devices for transdermal application (such as those described in European Patent Application No. 566,816 A; U.S. Pat. Nos. 5,613,958; 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often, have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage, if a constant delivery rate of drug is provided without having to rely on their ability to take their medication at specific times of the day. Also patients who simply forget to take their drugs as prescribed are less likely to do so if they merely have to put on a skin patch periodically (e.g., every 3 day). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and ipropanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, the use of modulating agents as described herein to increase skin permeability may also facilitate sampling of the blood compartment by passive diffusion, permitting detection and/or measurement of the levels of specific molecules circulating in the blood. For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

Within a further aspect, methods are provided for enhancing delivery of a drug to a tumor in a mammal, comprising administering a modulating agent in combination with a drug to a tumor-bearing mammal. In one particularly preferred embodiment, a modulating agent is capable of disrupting cell adhesion mediated by multiple adhesion molecules. For example, a single branched modulating agent (or multiple agents linked to a single molecule or support material) may disrupt claudin, occludin, cadherin (classical and/or nonclassical, such as Dsc, Dsg, OB-cadherin and/or VE-cadherin) and integrin mediated cell adhesion, thereby disrupting tight junctions, adherens junctions, and desmosomes. Multifunctional modulating agents comprising the claudin CAR sequence IYSY (SEQ ID NO:2) linked to one or more of the classical cadherin CAR sequence HAV; the sequence RGD, which is bound by integrins; and/or a nonclassical cadherin CAR sequence, such as a Dsc CAR sequence (IEK, VER or IER), a Dsg CAR sequence (INQ, INR or LNK), an occludin CAR sequence (LYHY; SEQ ID NO:17), an OB-cadherin CAR sequence (DDK, EEY or EAQ) and/or the VE-cadherin CAR sequence DAE, may be used to disrupt cell adhesion. Alternatively, a separate modulator of non-claudin-mediated cell adhesion may be administered in conjunction with the modulating agent(s), either within the same pharmaceutical composition or separately. Preferred antibody modulating agents that may be used in conjunction with the claudin modulating agents include Fab fragments directed against either an N-cadherin CAR sequence (such as FHLRAHAVDINGNQV-NH$_2$; SEQ ID NO:25) or an E-cadherin CAR sequence LFSHAVSSNG-NH$_2$ (SEQ ID NO:26), an occludin CAR sequence, such as QYLYHYCVVD-NH$_2$ (SEQ ID NO:478), or an OB-cadherin CAR sequence, such as IFVIDDKSG-NH$_2$ (SEQ ID NO:479).

Preferably, the modulating agent and the drug are formulated within the same composition or drug delivery device prior to administration. In general, a modulating agent may enhance drug delivery to any tumor, and the method of administration may be chosen based on the type of target tumor. For example; injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 1 µg/mL to about 2 mg/mL, and more preferably from about 10 µg/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Cancer tumors are solid masses of cells, growing out of control, which require nourishment via blood vessels. The formation of new capillaries is a prerequisite for tumor growth and the emergence of metastases. Administration of modulating agents as described herein may disrupt the growth of such blood vessels, thereby providing effective therapy for the cancer and/or inhibiting metastasis. Modulating agents may also be used to treat leukemias. In one particularly preferred embodiment, a modulating agent is capable of disrupting cell adhesion mediated by multiple adhesion molecules. For example, a single branched modulating agent (or multiple agents linked to a single molecule or support material) may disrupt claudin, cadherin and integrin mediated cell adhesion, thereby disrupting tight junctions, adherens junctions, focal contacts and desmosomes. Multifunctional modulating agents comprising a claudin CAR sequence linked to one or more of the classical cadherin CAR sequence HAV; the sequence RGD, which is bound by integrins; and/or a nonclassical cadherin CAR sequence, such as a Dsc CAR sequence (IEK, VER and IER), a Dsg CAR sequence (INQ, INR and/or LNK), an OB-cadherin CAR sequence (DDK, EEY or EAQ), an occludin CAR sequence (LYHY; SEQ ID NO:17), and/or the VE-cadherin CAR sequence DAE, may be used to disrupt cell adhesion. Alternatively, a separate modulator of non-claudin-mediated cell adhesion may be administered in conjunction with the modulating agent(s), either within the same pharmaceutical composition or separately. Preferred antibody modulating agents that may be used in conjunction with the claudin modulating agents include Fab fragments directed against either an N-cadherin CAR sequence, such as FHLRAHAVDINGNQV-NH$_2$ (SEQ ID NO:25), an E-cadherin CAR sequence, such as LFSHAVSSNG-NH$_2$ (SEQ ID NO:26), an occludin CAR sequence, such as QYLYHYCVVD-NH$_2$ (SEQ ID NO:478), or an OB-cadherin CAR sequence, such as IFVIDDKSG-NH$_2$ (SEQ ID NO:479).

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

Within a further related aspect, a modulating agent may be used to inhibit angiogenesis (i.e., the growth of blood vessels from pre-existing blood vessels) in a mammal. Inhibition of angiogenesis may be beneficial, for example, in patients afflicted with diseases such as cancer or arthritis. In one particularly preferred embodiment, a modulating agent is capable of disrupting cell adhesion mediated by multiple adhesion molecules. For example, a single branched modulating agent (or multiple agents linked to a single molecule or support material) may disrupt claudin, occludin, classical cadherin, and integrin mediated cell adhesion, thereby disrupting tight junctions, adherens junctions, and focal contacts. Multifunctional modulating agents comprising a claudin CAR sequence linked to one or more of the classical cadherin CAR sequence HAV, the sequence RGD, which is bound by integrins, the OB-cadherin CAR sequence (DDK, EEY or EAQ), the occludin CAR sequence (LYHY; SEQ ID NO:17) and/or the VE-cadherin CAR sequence DAE may be used to disrupt cell adhesion. Alternatively, a separate modulator of non-claudin-mediated cell adhesion may be administered in conjunction with the modulating agent(s), either within the same pharmaceutical composition or separately. Preferred antibody modulating agents that may be used in conjunction with the claudin modulating agents include Fab fragments directed against an N-cadherin CAR sequence, such as FHLRAHAVDINGNQV-NH$_2$ (SEQ ID NO:25), an occludin CAR sequence, such as QYLYHYCVVD-NH$_2$ (SEQ ID NO:478), or an OB-cadherin CAR sequence, such as IFVIDDKSG-NH$_2$ (SEQ ID NO:479).

The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 5 to 50 µg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 50 µg/mesh.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for inducing apoptosis in a claudin-expressing cell. In general, patients afflicted with cancer may benefit from such treatment. In one particularly preferred embodiment, a modulating agent is capable of disrupting cell adhesion mediated by multiple adhesion molecules. For example, a single branched modulating agent (or multiple agents linked to a single molecule or support material) may disrupt claudin, occludin, classical cadherin, and integrin mediated cell adhesion, thereby disrupting tight junctions, adherens junctions, and focal contacts. Multifunctional modulating agents comprising a claudin CAR sequence linked to one or more of the cadherin CAR sequence HAV and/or the sequence RGD, which is bound by integrins, and occludin CAR sequence LYHY (SEQ ID NO:17) may be used to disrupt cell adhesion. Alternatively, a separate modulator of non-claudin-mediated cell adhesion may be administered in conjunction with the modulating agent(s), either within the same pharmaceutical composition or separately. Preferred antibody modulating agents that may be used in conjunction with the claudin modulating agents include Fab fragments directed against either an N-cadherin CAR sequence, such as FHLRAHAVDINGNQV-$NH_2$ (SEQ ID NO:25), or an E-cadherin CAR sequence, such as LFSHAVSSNG-$NH_2$ (SEQ ID NO:26), an occludin CAR sequence, such as QYLYHYCVVD-$NH_2$ (SEQ ID NO:478), or an OB-cadherin CAR sequence, such as IFVIDDKSG-$NH_2$ (SEQ ID NO:479).

Administration of modulating agents to induce apoptosis may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. In one particularly preferred embodiment, a modulating agent is capable of disrupting cell adhesion mediated by multiple adhesion molecules. For example, a single branched modulating agent (or multiple agents linked to a single molecule or support material) may disrupt claudin, occludin and cadherin mediated cell adhesion, thereby disrupting tight junctions and adherens junctions. Multi-functional modulating agents comprising a claudin CAR sequence linked to one or more of the classical cadherin CAR sequence HAV, the occludin CAR sequence LYHY (SEQ ID NO:17), the OB-cadherin CAR sequence (DDK, EEY or EAQ) and/or the VE-cadherin CAR sequence DAE, preferably by way of a linker, are also preferred. Alternatively, a separate modulator of non-claudin-mediated cell adhesion may be administered in conjunction with the modulating agent(s), either within the same pharmaceutical composition or separately. Preferred antibody modulating agents that may be used in conjunction with the claudin modulating agents include Fab fragments directed against the N-cadherin CAR sequence FHLRAHAVDINGNQV-$NH_2$ (SEQ ID NO:25), an occludin CAR sequence, such as QYLYHYCVVD-$NH_2$ (SEQ ID NO:478), or an OB-cadherin CAR sequence, such as IFVIDDKSG-$NH_2$ (SEQ ID NO:479).

In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

In certain other aspects, the present invention provides methods for enhancing adhesion of claudin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising HAV and RGD sequences may be attached to the same matrix, preferably in an alternating pattern). Such matrices may be used in contexts in which it is desirable to enhance adhesion mediated by multiple cell adhesion molecules. Alternatively, the modulating agent itself may comprise multiple claudin CAR sequences or antibodies (or fragments thereof), separated by linkers as described above. Either way, the modulating agent(s) function as a "biological glue" to bind multiple claudin-expressing cells within a variety of contexts.

Within one such aspect, modulating agents comprising multiple claudin CAR sequences and/or multiple modulating agents linked to a single molecule or support material may be used to enhance wound healing and/or reduce scar tissue in a mammal. Modulating agents that are linked to a biocompatible and biodegradable matrix such as cellulose or collagen are particularly preferred. For use within such methods, a modulating agent should have a free amino or hydroxyl group. The modulating agents are generally administered topically to the wound, where they may facilitate closure of the wound and may augment, or even replace, stitches. Similarly, administration of matrix-linked modulating agents may facilitate cell adhesion in skin grafting and prosthetic implants, and may prolong the duration and usefulness of collagen injection. In general, the amount of matrix-linked modulating agent administered to a wound, graft or implant site varies with the severity of the wound and/or the nature of the wound, graft, or implant, but may vary as discussed above. Multi-functional modulating agents comprising the claudin CAR sequence, IYSY (SEQ ID NO:2), the classical cadherin CAR sequence (HAV), the integrin CAR sequence (RGD), the occludin CAR sequence LYHY (SEQ ID NO:17), as well as a nonclassical cadherin CAR sequence, such as the OB-cadherin CAR sequence (DDK, EEY or EAQ), the VE-cadherin CAR sequence DAE and/or one or more of the Dsc and Dsg CAR sequences IEK, VER, IER, INQ, INR and/or LNK, may also be used as potent stimulators of wound healing and/or to reduce scar tissue. Alternatively, one or more separate modulator of cadherin-, integrin-, and/or nonclassical cadherin-mediated cell adhesion may be administered in conjunction with the modulating agent(s), either within the same pharmaceutical composition or separately.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize claudin-expressing cells. For example, dishes or plates coated with one or more modulating agents may be used to immobilize claudin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics. glass and silica.

Other aspects of the present invention provide methods that employ antibodies raised against the modulating agents for diagnostic and assay purposes. Assays typically involve using an antibody to detect the presence or absence of claudin (free or on the surface of a cell), or proteolytic fragment containing the EC1 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g. Harlow and Lane, *Antibodies: A Laboratory Manual,* Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target claudin, or a proteolytic fragment containing the EC1 domain and encompassing the CAR sequence, and remove it from the remainder of the sample. The bound claudin may then be detected using a second antibody or reagent that contains a reporter group. Alternatively, a competitive assay may be utilized, in which the claudin is labeled with a reporter group and allowed to bind to the immobilized antibody after incubation of the antibody with the sample. The extent to which components of the sample inhibit the binding of the labeled claudin to the antibody is indicative of the reactivity of the sample with the immobilized antibody, and as a result, indicative of the level of the claudin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of claudin in a sample is a two-antibody sandwich assay. This assay may be performed by first contacting an antibody that has been immobilized on a solid support, commonly the well of a microtiter plate, with the biological sample, such that the claudin within the sample is allowed to bind to the immobilized antibody (a 30 minute incubation time at room temperature is generally sufficient). Unbound sample is then removed from the immobilized claudin-antibody complexes and a second antibody (containing a reporter group such as an enzyme, dye, radionuclide, luminescent group, fluorescent group or biotin) capable of binding to a different site on the claudin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of claudin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing claudin (or different claudin levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating claudin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate claudin-mediated cell adhesion.

The following examples are offered by way of illustration and not by way of limitation.

EXAMPLE 1

Preparation of Representative Cyclic Peptides

This Example illustrates the solid phase synthesis of representative linear and cyclic peptides as modulating agents.

The peptides are assembled on methylbenzhydrylamine resin (MBHA resin) for the C-terminal amide peptides. The traditional Merrifield resins are used for any C-terminal acid peptides. Bags of a polypropylene mesh material are filled with the resin and soaked in dichloromethane. The resin packets are washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane is added to activate the coupling reaction. The bottle is shaken for one hour to ensure completion of the reaction. The reaction mixture is discarded and the packets washed with DMF. The N-α-Boc is removed by acidolysis using a 55% TFA in dichloromethane for 30 minutes leaving the TFA salt of the α-amino group. The bags are washed and the synthesis completed by repeating the same procedure while substituting for the corresponding amino acid at the coupling step. Acetylation of the N-terminal is performed by reacting the peptide resins with a solution of acetic anhydride in dichloromethane in the presence of diisopropylethylamine. The peptide is then side-chain deprotected and cleaved from the resin at 0° C. with liquid HF in the presence of anisole as a carbocation scavenger.

The crude peptides are purified by reversed-phase high-performance liquid chromatography. Purified linear precursors of the cyclic peptides are solubilized in 75% acetic acid at a concentration of 2–10 mg/mL. A 10% solution of iodine in methanol is added dropwise until a persistent coloration was obtained. A 5% ascorbic acid solution in water is then added to the mixture until discoloration. The disulfide bridge containing compounds are then purified by HPLC and characterized by analytical HPLC and by mass spectral analysis.

EXAMPLE 2

System for Assessing Endothelial Cell Adhesion

This Example illustrates an endothelial cell adhesion assay for evaluating the effects of modulating agents on endothelial cell adhesion.

A. Cell Culture

Human aortic enidothelial cells (HAEC) are cultured on fibronectin (Sigma, St. Louis, Mo.) according to the procedures of Jaffe et al., *J. Clin. Invest.* 52:2745–27561 1973. Cells are maintained in EGM (endothelial cell growth medium; Clonetics, San Diego, Calif.) and used for experiments at passage 4.

B. Claudin and VE-cadherin Immunolocalization Methods

HAEC are cultured on fibronectin-coated coverslips. Confluent cultures of HAEC are exposed to linear peptides (final concentration 100 μg/ml EGM), or EGM alone for 1 hour. The cells are then fixed for 30 minutes at 4° C. in 95% ethanol, followed by fixation in acetone for 1 minute at 4° C. (Furuse et al., *J. Cell Biol.* 123:1777–1788, 1993). After fixation, the cells are allowed to air dry at room temperature. The cells are probed with either mouse anti-VE-cadherin antibodies (Hemeris, Sassenage, France; diluted 1:250 in 0.1% dried skim milk powder dissolved in PBS), or anti-claudin antibodies (prepared as described by Morita et al., *Proc. Natl. Acad. Sci. USA* 96:511–516, 1999, and generally as described in Blaschuk and Farookhi, *Dev. Biol.* 136:564–567, 1989) diluted in 0.1% dried skim milk powder dissolved in PBS) for 1 hour at 37° C. Briefly, a nine amino acid peptide comprising a claudin CAR sequence is linked to KLH and injected into rabbits. The animals are bled, and polyclonal antibodies specific for the CAR sequence are purified from the antisera by affinity chromatography using the peptide coupled to a solid support.

The cells are then washed with 0.1% dried skim milk powder dissolved in PBS (three washes, 5 minutes/wash), and probed with secondary antibodies (donkey anti-mouse Cy3, or donkey anti-rabbit Cy5 diluted 1:250 in 0.1% dried skim milk powder dissolved in PBS; Jackson Immunoresearch Laboratories Inc., Westgrove, Pa.) for 1 hour at 37° C. The cells are washed again with in 0.1% dried skim milk powder dissolved in PBS and mounted in a solution composed of 50% glycerol and 50% PBS to which phenylenediamine (Sigma, St. Louis, Mo.) had been added to a final concentration of 1 mg/ml. The samples are analyzed using a Bio-Rad MRC 1000 confocal microscope with Laser Sharp software version 2.1T (Bio-Rad, Hercules, Calif.). Staining for claudin is assigned the pseudo-color red, whereas VE-cadherin staining is assigned pseudo-color green using Confocal Assistant 4.02 software. The endothelial cells are seen to retract from one another when cultured in the presence of a modulating agent comprising a claudin CAR sequence, indicating that adhesion is decreased between the cells. Furthermore, the cells do not form cobblestone-like monolayers when exposed to such an agent. Surface expression of both VE-cadherin and claudin is greatly reduced in the cells treated with modulating agent, as compared to the VE-cadherin and claudin levels expressed by untreated cells.

EXAMPLE 3

Assay for Evaluating Effect of Representative Modulating Agents on Vasopermeability This Example illustrates a vasopermeability assay for evaluating the effects of modulating agents on endothelial cell permeability in vivo.

A. Miles Assay for Vascular Permeability

The ability of cyclic and linear peptides to increase vascular permeability is assessed utilizing the Miles assay (McClure et al., *J. Pharmacological & Toxicological Meth.* 32:49–521994). The peptides are dissolved in phosphate buffered saline (PBS) at a concentration of 100 μg/ml. Adult rats are given 100 μl subdermal injections of each peptide solution into their shaved backs, followed 15 minutes later by a single 250 μl injection of 1% Evans blue dissolved in PBS into their tail veins. The subdermal injection sites are visually monitored for the appearance of blue dye. Once the dye appears, each subdermal injection site is excised, weighed, and placed in 1 ml dimethylformamide for 24 hours to extract the dye. The optical density of the dye extracts is determined at 620 nm. More blue dye is seen to accumulate at sites where the peptide was injected, as opposed to sites where phosphate buffered saline was injected.

EXAMPLE 4

Assay for Evaluating Effect of Representative Modulating Agents on NRK Cell Adhesion This Example illustrates an assay for evaluating the effects of modulating agents on adhesion of NRK cells.

NRK cells (ATCC #1571-CRL) are plated at 10–20,000 cells per 35 mm tissue culture flasks containing DMEM with 10% FCS and sub-cultured periodically (Laird et al., *J. Cell Biol.* 131:1193–1203, 1995). Cells are harvested and replated in 35 mm tissue culture flasks containing 1 mm coverslips and incubated until 50–65% confluent (24–36 hours). At this time, coverslips are transferred to a 24-well plate, washed once with fresh DMEM and exposed to modulating agent at a concentration of 0.1 mg/mL for 24 hours. Fresh modulating agent is then be added, and the cells left for an additional 24 hours. Cells are fixed with 100% methanol for 10 minutes and then washed three times with PBS. Coverslips are blocked for 1 hour in 2% BSA/PBS and incubated for a further 1 hour in the presence of anti-claudin antibody, as described above, and mouse anti-E-cadherin antibody (Transduction Labs, 1:250 dilution). Primary and secondary antibodies are diluted in 2% BSA/PBS. Following incubation in the primary antibody, coverslips are washed three times for 5 minutes each in PBS and incubated for 1 hour with donkey anti-mouse Cy3 and donkey anti-rabbit Cy5 (Jackson Immunoresearch Laboratories Inc., Westgrove, Pa.) for 1 hour at 37° C. Following further washes in PBS (3×5 min) coverslips are mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts claudin-mediated cell adhesion assume a non-polygonal and elongated morphology (i.e., a fibroblast-like shape) within 48 hours of treatment with 0.1 mg/mL of modulating agent. Gaps appear in confluent cultures of such cells. In addition, 0.1 mg/mL of such a modulating agent reproducibly induces a readily apparent reduction in cell surface staining of claudin and E-cadherin, as judged by immunofluorescence microscopy (Laird et al., *J. Cell Biol.* 131:1193–1203, 1995) within 48 hours.

EXAMPLE 5

Effect of Representative Modulating Agents on Electrical Resistance Across Cell Monolayer This Example illustrates an electrical resistance assay for evaluating the effects of claudin-modulating agents on epithelial cell adhesion.

Madin Darby canine kidney (MDCK) cells were plated in Millicells (Millipore, Bedford, Mass.), at a density of 300,000 cells per Millicell, and cultured in Dulbecco's Modified Eagle Medium (DMEM; Sigma, St. Louis., Mo.) containing 5% fetal calf serum (Sigma, St. Louis, Mo.) until monolayers formed. Monolayers were exposed to the modulating agent dissolved in medium. The electrical resistance was measured using the EVOM device (World Precision Instruments, Sarasota, Fla.). At the time of measurement, fresh medium, with or without the modulating agent, may be added to the Millicells.

Figure 3:
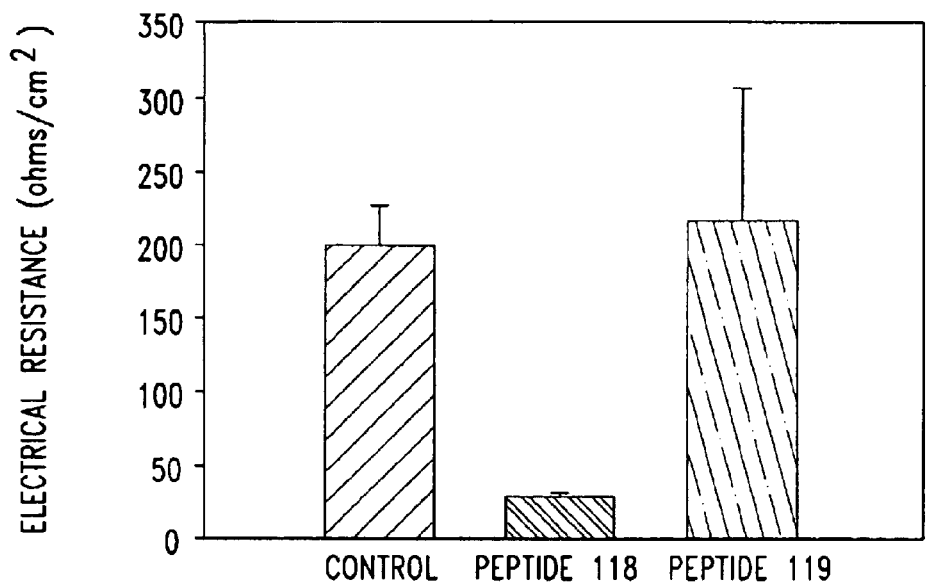
FIG. 3 is a histogram depicting the mean electrical resistance across MDCK cell monolayers cultured for 18 hours in medium alone (Control), medium containing N-Ac-WKIYSYAGDN-NH$_2$ (Peptide 118; SEQ ID NO:475) or H-WKIYSYAGDN-NH$_2$ (Peptide 119; SEQ ID NO:475) at a concentration of 0.5 mg/ml. Duplicate measurements were taken, and error bars represent the standard deviation.

FIG. 3 shows the mean electrical resistance across MDCK cell monolayers cultured for 18 hours in medium alone (Control), medium containing N-Ac-WKIYSYAGDN-$NH_2$ (Peptide 118; SEQ ID NO:475) or H-WKIYSYAGDN-$NH_2$ (Peptide 119; SEQ ID NO:475) at a concentration of 0.5 mg/ml. Duplicate measurements were taken, and error bars represent the standard deviation. Peptide 118 reduced the electrical resistance across the monolayer, while peptide 119 did not change the electrical resistance across the monolayer relative to the control.

Figure 4:
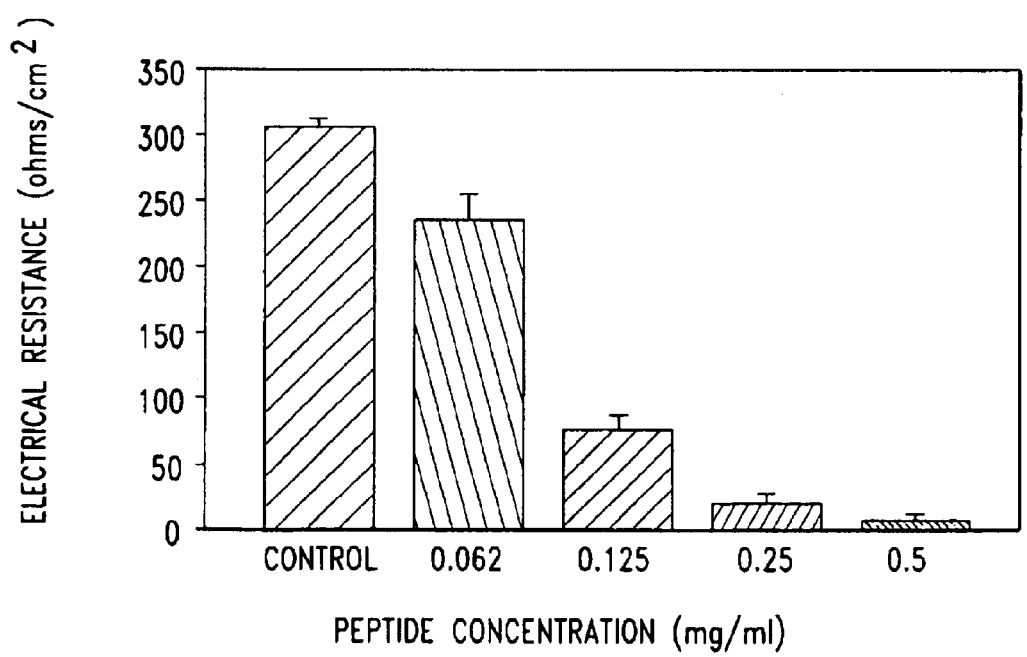
FIG. 4 is a histogram depicting the mean electrical resistance across MDCK cell monolayers cultured for 24 hours in medium alone (Control) or medium containing N-Ac-WKIYSYAGDN-NH$_2$ (Peptide 118; SEQ ID NO:475) at various concentrations.

FIG. 4 shows the mean electrical resistance across MDCK cell monolayers cultured for 24 hours in medium alone (Control) or medium containing N-Ac-WKIYSYAGDN-$NH_2$ (Peptide 118; SEQ ID NO:475) at various concentrations. Peptide 118 reduced the electrical resistance across the monolayer in a dose dependent manner.

These results demonstrate the ability of modulating agents to inhibit the formation of tight junctions in epithelial cells, as well as the effect of the N-Ac group of activity of this particular modulating agent.

From the foregoing, it will be evident that although specific embodiments of the invention have been described herein for the purpose of illustrating the invention, various modifications may be made without deviating from the spirit and scope of the invention. Accordingly, the invention is not limited except as by the appended claims.

What is claimed is:

1. A cell adhesion modulating composition comprising:
   (a) a polypeptide consisting of between 5–50 consecutive amino acids of SEQ ID NO: 471, wherein said polypeptide comprises the formula:

Trp-Gln-Aaa-Baa-Ala-Phe-Caa-Asp     (SEQ ID NO:1)

wherein Aaa, Baa and Caa indicate independently selected amino acid residues.

2. A cell adhesion modulating composition comprising:
   (a) a polypeptide consisting of between 7–50 consecutive amino acids of SEQ ID NO: 471, wherein said polypeptide comprises the formula:

Trp-Gln-Aaa-Baa-Ala-Phe-Caa-Asp     (SEQ ID NO:1)

wherein Aaa, Baa and Caa indicate independently selected amino acid residues.

3. A cell adhesion composition comprising:
   (a) a polypeptide consisting of between 8–50 consecutive amino acids of SEQ ID NO: 471, wherein said polypeptide comprises the formula:

Trp-Gln-Aaa-Baa-Ala-Phe-Caa-Asp     (SEQ ID NO:1)

wherein Aaa, Baa and Caa indicate independently selected amino acid residues.

4. A cell adhesion modulating composition according to any one of claims 1–3, wherein the polypeptide comprises an amino acid sequence selected from the group consisting of: VTAFLD (SEQ ID NO:271), QVTAF (SEQ ID NO:272), QVTAFL (SEQ ID NO:273), QVTAFLD (SEQ ID NO:274), WQVTAF (SEQ ID NO:275), WQVTAFL (SEQ ID NO:276) and WQVTAFLD (SEQ ID NO:277).

5. A cell adhesion modulating composition that comprises a linear peptide consisting of no more than 50 consecutive amino acid residues of SEQ ID NO:471 and comprising the sequence N-Ac-WQVTAFLD-NH$_2$ (SEQ ID NO:50).

* * * * *